US009617299B2

(12) United States Patent
Nonaka et al.

(10) Patent No.: US 9,617,299 B2
(45) Date of Patent: Apr. 11, 2017

(54) METHOD FOR PRODUCING PROTEIN BY PRECIPITATION

(71) Applicant: AJINOMOTO CO., INC., Chuo-ku (JP)

(72) Inventors: Takahiro Nonaka, Kawasaki (JP); Teruhisa Mannen, Kawasaki (JP); Noriko Tsurui, Kawasaki (JP)

(73) Assignee: AJINOMOTO CO., INC., Chou-ku (JP)

( * ) Notice: Subject to any disclaimer, the term of this patent is extended or adjusted under 35 U.S.C. 154(b) by 0 days.

(21) Appl. No.: 15/135,012

(22) Filed: Apr. 21, 2016

(65) Prior Publication Data

US 2016/0222055 A1     Aug. 4, 2016

Related U.S. Application Data

(63) Continuation of application No. 14/539,562, filed on Nov. 12, 2014, now abandoned, which is a continuation of application No. PCT/JP2014/053810, filed on Feb. 18, 2014.

(30) Foreign Application Priority Data

Feb. 18, 2013    (JP) ................................ 2013-029397

(51) Int. Cl.
| | |
|---|---|
| *C12P 21/06* | (2006.01) |
| *C07K 1/30* | (2006.01) |
| *C07K 14/00* | (2006.01) |
| *C07K 14/815* | (2006.01) |
| *C07K 14/32* | (2006.01) |
| *C07K 1/34* | (2006.01) |
| *C07K 1/36* | (2006.01) |
| *C07K 14/34* | (2006.01) |
| *C07K 14/62* | (2006.01) |
| *C07K 14/635* | (2006.01) |

(52) U.S. Cl.
CPC .................. *C07K 1/30* (2013.01); *C07K 1/34* (2013.01); *C07K 1/36* (2013.01); *C07K 14/00* (2013.01); *C07K 14/32* (2013.01); *C07K 14/34* (2013.01); *C07K 14/62* (2013.01); *C07K 14/635* (2013.01); *C07K 14/815* (2013.01); *C07K 2319/00* (2013.01); *C07K 2319/50* (2013.01); *C07K 2319/70* (2013.01)

(58) Field of Classification Search
CPC .................................. C07K 1/30; C07K 14/00
USPC ........................................ 435/68.1; 530/418
See application file for complete search history.

(56) References Cited

U.S. PATENT DOCUMENTS

| 2003/0082746 A1 | 5/2003 | Kikuchi et al. |
|---|---|---|
| 2007/0184525 A1 | 8/2007 | Date et al. |
| 2010/0297729 A1 | 11/2010 | Kikuchi et al. |
| 2014/0220637 A1 | 8/2014 | Tsurui et al. |

FOREIGN PATENT DOCUMENTS

| EP | 1748077 | 1/2007 |
|---|---|---|
| EP | 2 423 217 A1 | 2/2012 |
| JP | 2004-035409 A | 2/2004 |
| JP | 4320769 B2 | 8/2009 |
| WO | 2004/029254 A1 | 4/2004 |
| WO | 2005/103278 A1 | 11/2005 |
| WO | 2008/122089 | 10/2008 |
| WO | 2009/103752 | 8/2009 |
| WO | 2013/062029 A1 | 5/2013 |

OTHER PUBLICATIONS

European Extended Search Report (EESR) issued on Dec. 16, 2015, corresponding European Patent application No. 14751491.3.
Zhaoyang Xiu, et al. "A New Method for the Preparation of Human Parathyroid Hormone 1-34 Peptides" Biotechnology Appl. Biochem. Oct. 2002, vol. 36. pp. 111-117 (Printed in Great Britain) XP-002751631.
International Search Report and Written Opinion issued Apr. 8, 2014 in PCT/JP2014/053810.
Combined Office Action and Search Report issued Nov. 3, 2015 in Chinese Patent Application No. 201480001911.4 (with English language translation).
Michael Groβ, et al., "Formation of amyloid fibrils by peptides derived from the bacterial cold shock protein CspB" Protein Science, vol. 8, 1999, pp. 1350-1357.
N. Hansmeier, et al., "Classification of hyper-variable Corynebacterium glutamicum surface-layer proteins by sequence analyses and atomic force microscopy" J. Biotechnol. 112, GenBank: AAS20306.1, Aug. 4, 2004.
Demain AI, and Vaishnav P., Production of recombinant proteins by microbes and higher organisms. Biotechnol Adv. May-Jun. 2009; 27 (3): 297-306. Epub Jan. 31, 2009. Review.
Omasa T, Onitsuka M, and Kim WD., Cell engineering and cultivation of chinese hamster ovary (CHO) cells. Curr Pharm Biotechnol. Apr. 2010; 11 (3): 233-40. Review.
Mattanovich D, Branduardi P, Dato L, Gasser B, Sauer M, and Porro D., Recombinant protein production in yeasts. Methods Mol Biol. 2012; 824: 329-58. Review.

(Continued)

*Primary Examiner* — Tekchand Saidha
(74) *Attorney, Agent, or Firm* — Oblon, McClelland, Maier & Neustadt, L.L.P.

(57) ABSTRACT

A method of purifying a fusion protein, including: (1) adjusting the pH of an aqueous phase, containing a fusion protein which is a fusion of a protein having a self-assembly capability and a tamet protein, and which aqueous phase has a first pH, to a second pH, to obtain a remaining aqueous phase and a solid fraction containing an amount of the fusion protein; (2) separating the solid fraction from the remaining aqueous phase, to obtain a separated solid fraction; and (3) dissolving the separated solid fraction in a solution having a pH of 12 or lower but higher than the second pH by at least 0.1 pH units, wherein the protein having a self-assembly capability is a cell surface protein.

33 Claims, 17 Drawing Sheets

(56) References Cited

OTHER PUBLICATIONS

Watanabe E, Tsoka S, and Asenjo JA., Selection of chromatographic protein purification operations based on physicochemical properties. Ann N Y Acad Sci. May 2, 1994; 721: 348-64.

Hober S, Nord K, and Linhult M., Protein A chromatography for antibody purification. J Chromatogr B Analyt Technol Biomed Life Sci. Mar. 15, 2007; 848 (1): 40-7. Epub Oct. 9, 2006. Review.

Garcia, F. A. P., Protein precipitation. Recovery Processes Biol. Mater. (1993), 355-67.

A. A. Green: J. Biol. Chern., 95, 47 (1932).

McCord JM, and Fridovich I., Superoxide dismutase. An enzymic function for erythrocuprein (hemocuprein). J Biol Chern. Nov. 25, 1969; 244 (22): 6049-55.

Ingham KC., Protein precipitation with polyethylene glycol. Methods Enzymol. 1984; 104: 351-6.

Cromwell ME, Hilario E, and Jacobson F., Protein aggregation and bioprocessing. AAPS J. Sep. 15, 2006; 8 (3): E572-9.

Mahler HC, Friess W, Grauschopf U, and Kiese S., J Pharm Sci. Sep. 2009; 98 (9): 2909-34. Protein aggregation: pathways, induction factors and analysis.

Hassouneh W, Christensen T, and Chilkoti A., Elastin-like polypeptides as a purification tag for recombinant proteins. Curr Protoc Protein Sci. Aug. 2010; Chapter 6: Unit 6.11.

Proc. Natl. Acad. Sci. USA, 1993, vol. 90, pp. 3334-3338.

Biotechnology Advances, 2002, 20, pp. 321-339.

PNAS, 2002, vol. 99, No. 8, pp. 5355-5360.

Biotechnology and Bioengineering, 2009, vol. 103, No. 2, pp. 241-251.

Smyth DR, Mrozkiewicz MK, McGrath WJ, Listwan P, and Kobe B., Crystal structures of fusion proteins with large-affinity tags. Protein Sci. Jul. 2003; 12 (7): 1313-22.

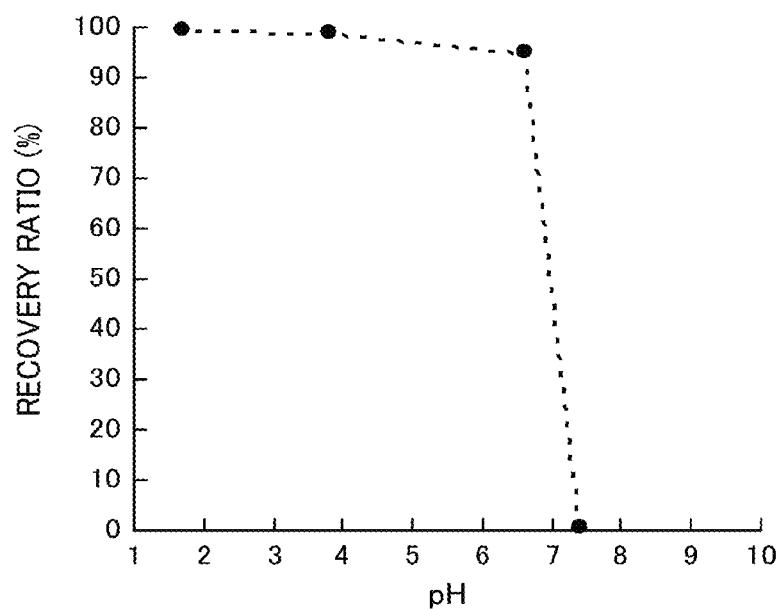

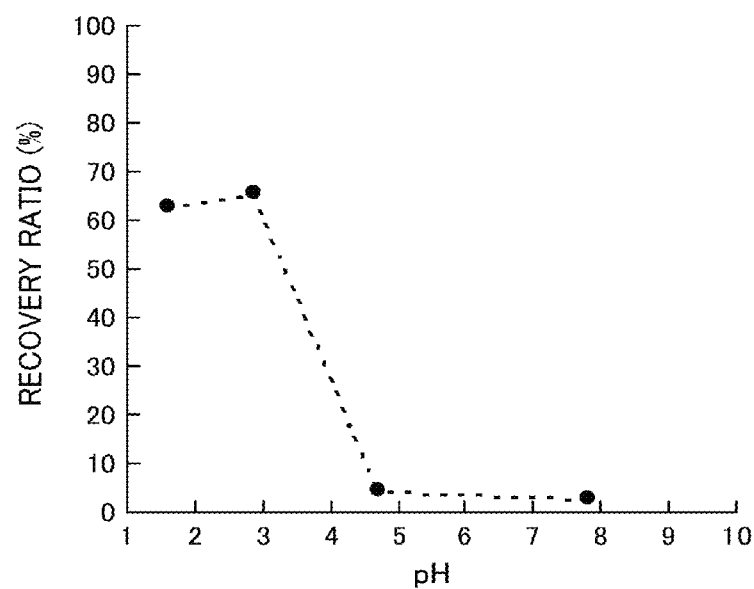

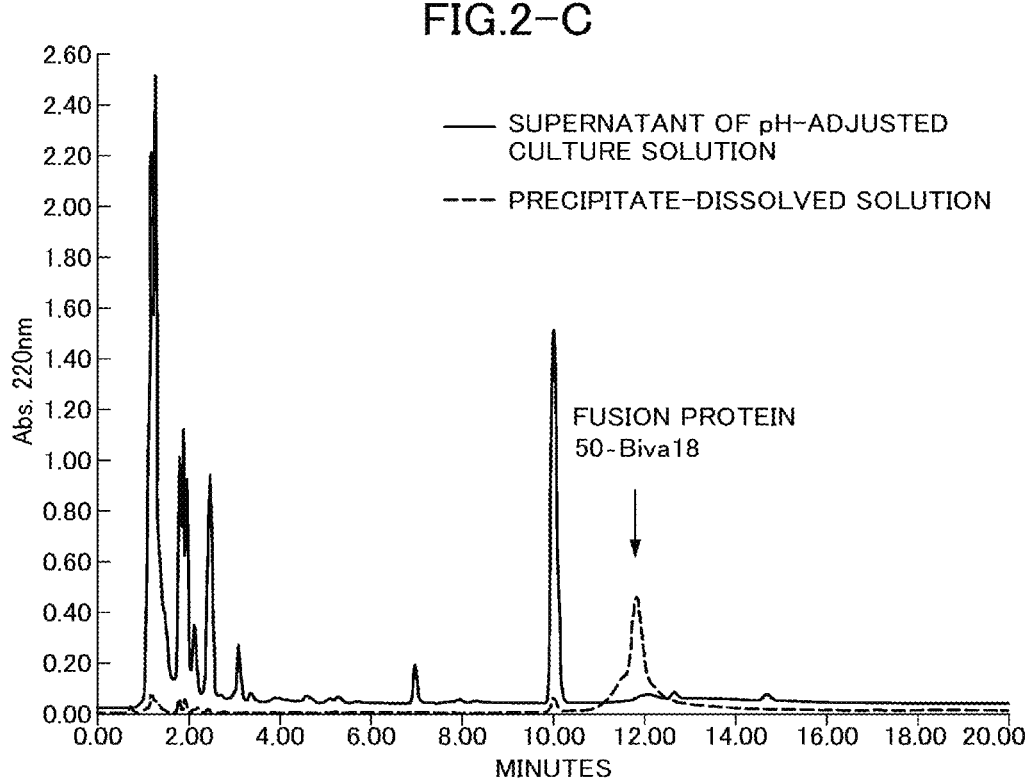
FIG.2-C
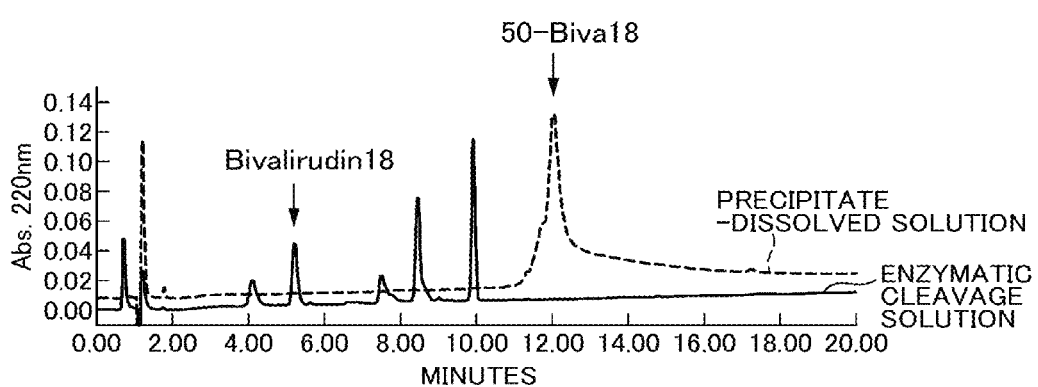
FIG.2-D

FIG.2-E
Elemental Composition: C84 H123 N22 O31
Monoisotopic M/Z: 1935.87191
Total Abundance: 100.00%
| Isotope Number | m/z | Percent Total | Percent Maximum |
|---|---|---|---|
| 0 | 1935.87191 | 32.99 | 95.13 |
| 1 | 1936.87484 | 34.68 | 100.00 |
| 2 | 1937.87760 | 20.14 | 58.07 |
| 3 | 1938.88027 | 8.39 | 24.21 |
| 4 | 1939.88288 | 2.79 | 8.04 |
| 5 | 1940.88544 | 0.78 | 2.25 |
| 6 | 1941.88797 | 0.19 | 0.55 |
| 7 | 1942.89049 | 0.04 | 0.12 |
| 8 | 1943.89298 | 0.01 | 0.02 |
| 9 | 1944.89552 | 0.00 | 0.00 |
| 10 | 1945.89818 | 0.00 | 0.00 |
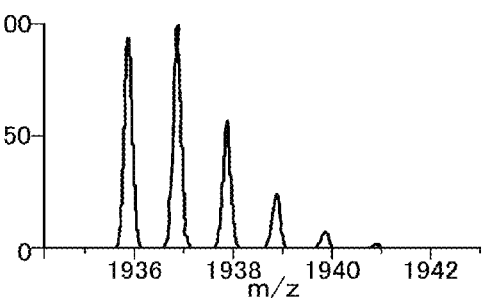
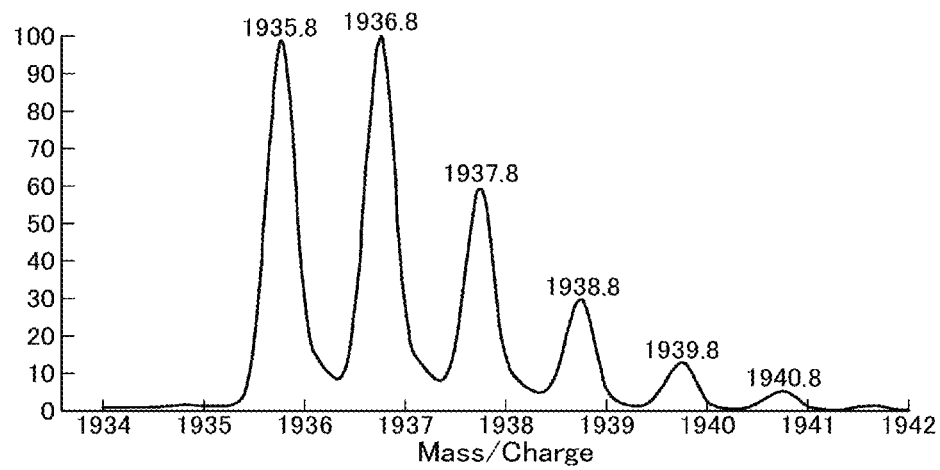
MASS CALCULATED FROM AMINO ACID SEQUENCE OF Biva18, AND MEASURED MASS OF PURIFIED SUBSTANCE OBTAINED IN THIS EXAMPLE FIG.2-F
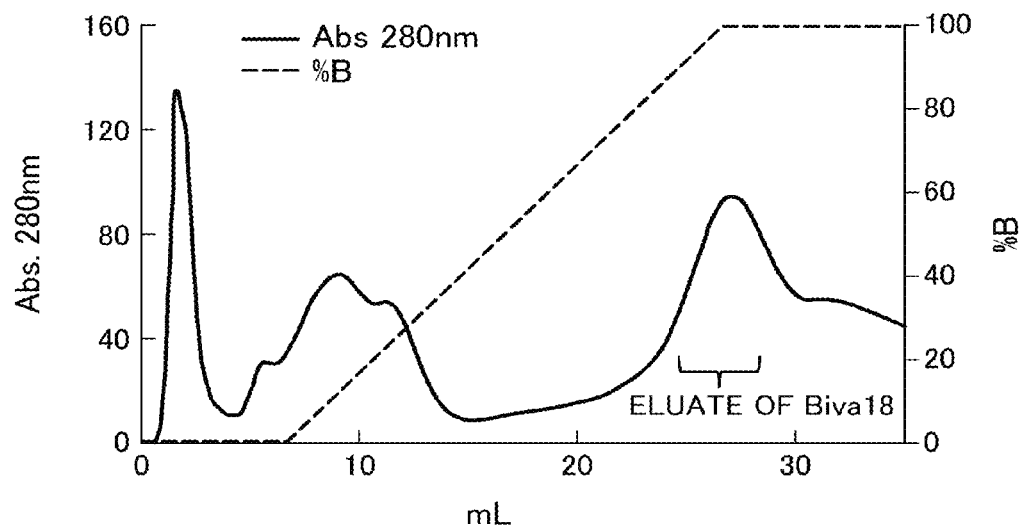
FIG.2-G
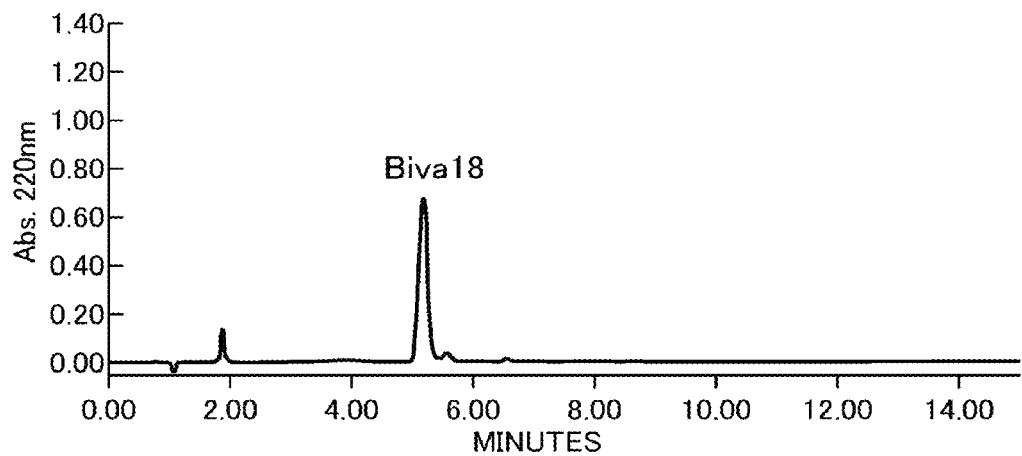

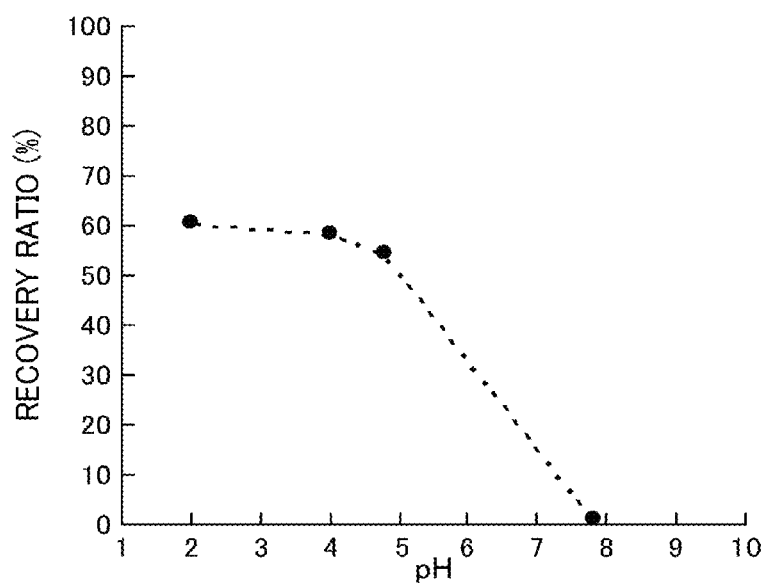

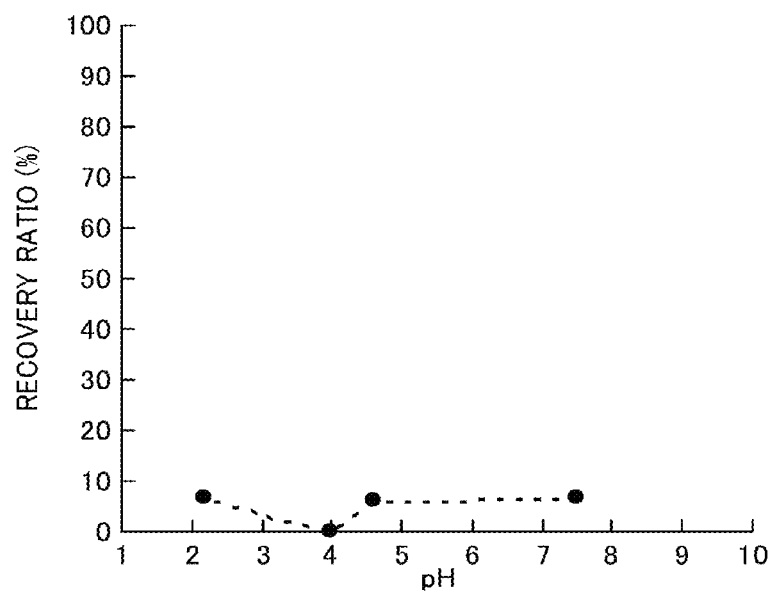
FIG.4-A
FIG.4-B

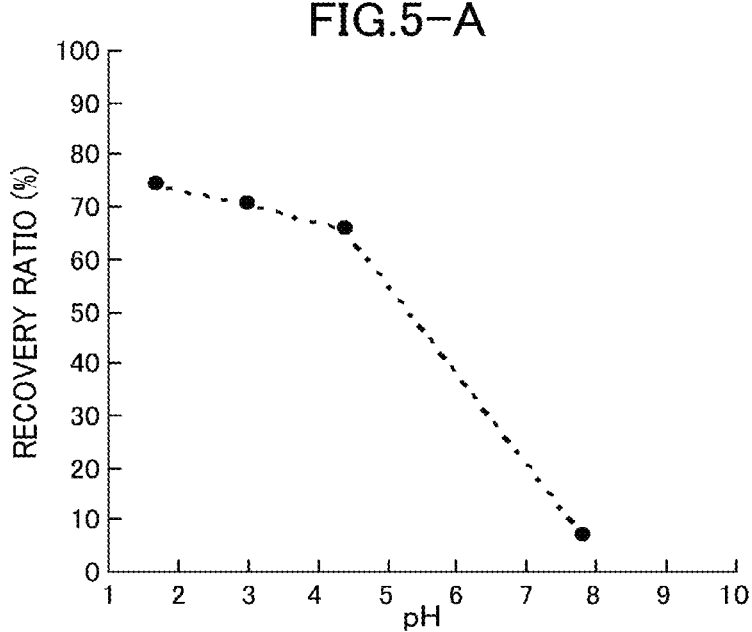
FIG.5-A
FIG.5-B
| pH OF pH-ADJUSTED CULTURE SOLUTION | 7.8 | 4.4 | 3.0 | 1.7 |
|---|---|---|---|---|
| SUPERNATANT OF pH-ADJUSTED CULTURE SOLUTION | | | | |
| PRECIPITATE -DISSOLVED SOLUTION | | | | |
| RECOVERY RATIO (%) | 7 | 66 | 70 | 74 |

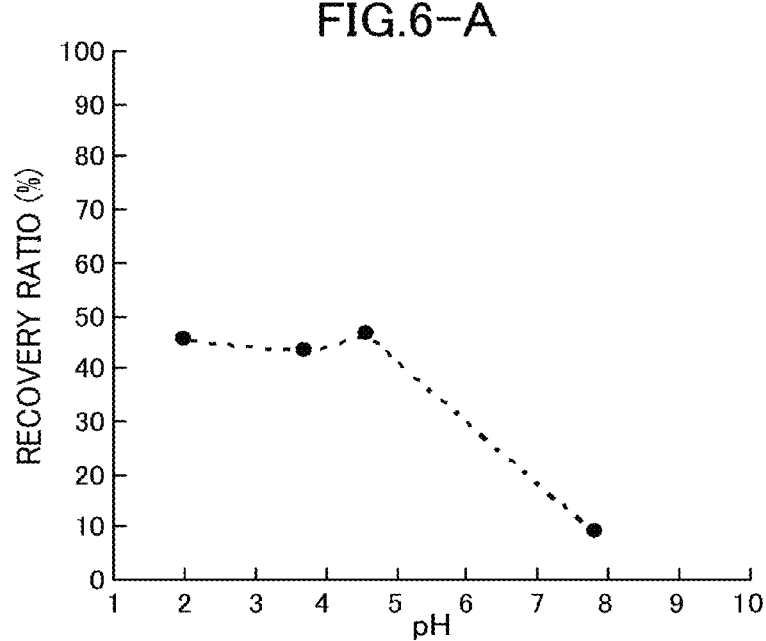

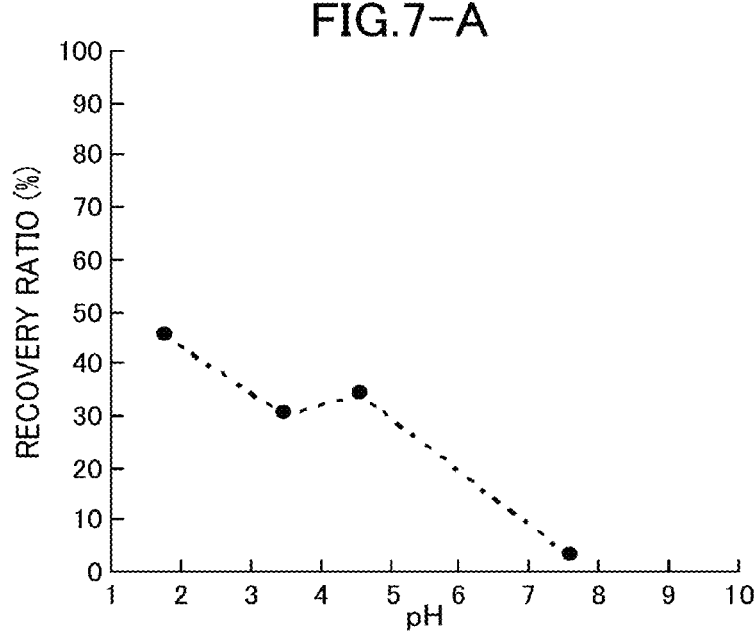

FIG.8-A
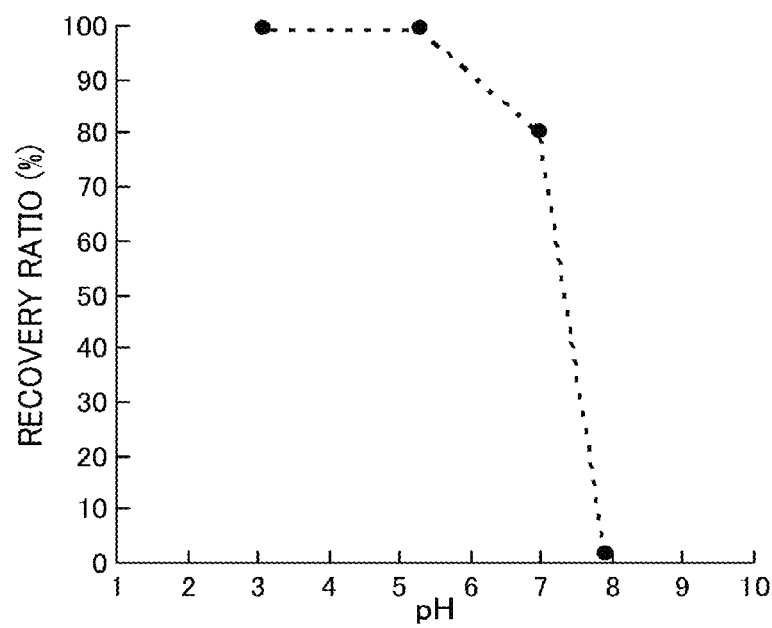
FIG.8-B
| pH OF pH-ADJUSTED CULTURE SOLUTION | 7.9 | 7.0 | 5.3 | 3.1 |
|---|---|---|---|---|
| SUPERNATANT OF pH-ADJUSTED CULTURE SOLUTION | | | | |
| PRECIPITATE -DISSOLVED SOLUTION | | | | |
| RECOVERY RATIO (%) | 2 | 80 | 100 | 99 |

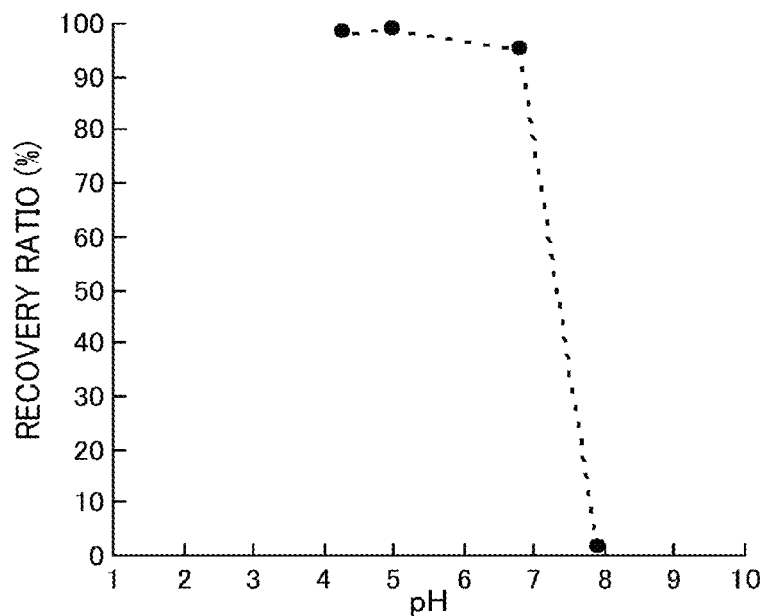

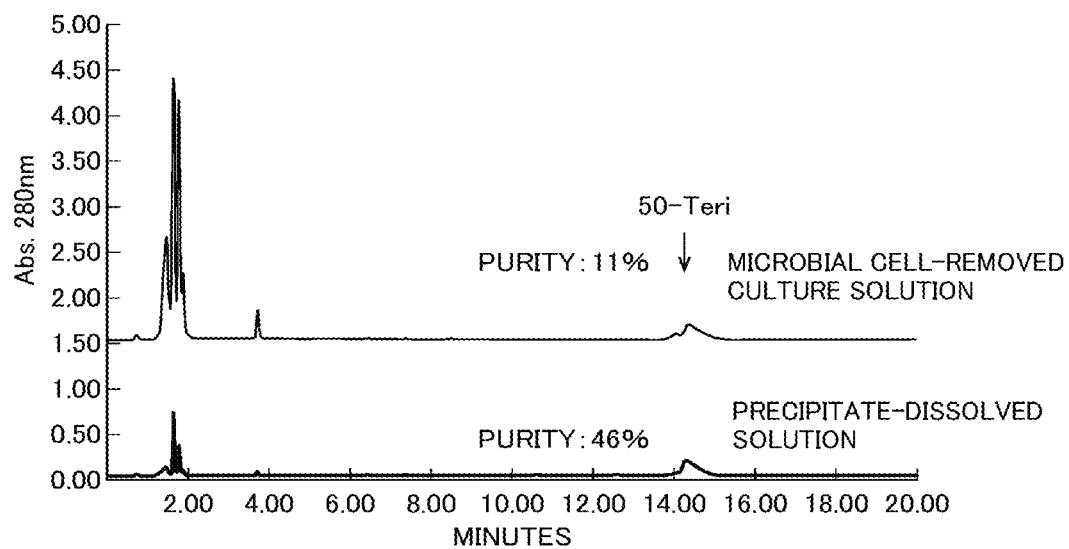
FIG.10-A
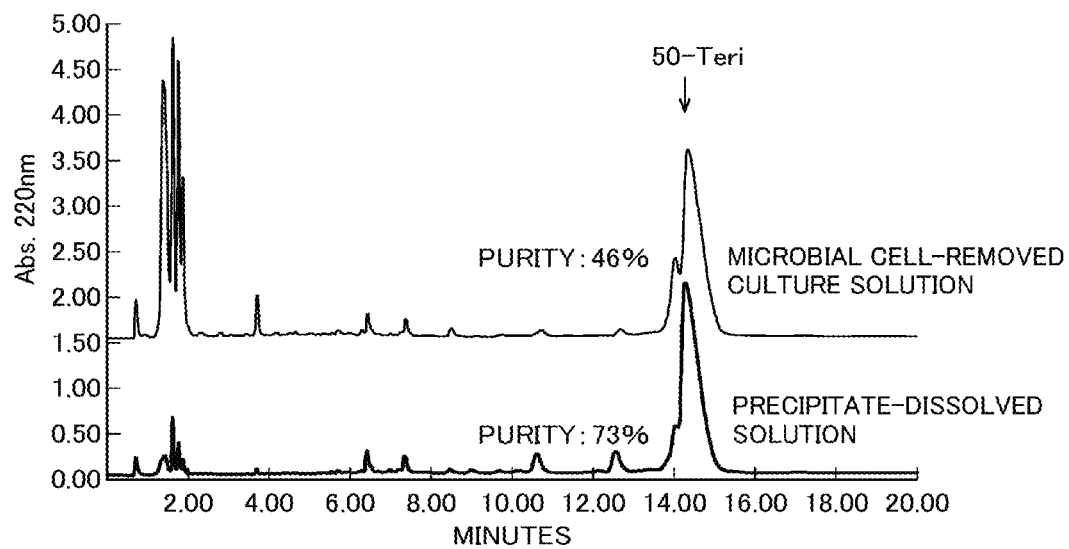
FIG.10-B

METHOD FOR PRODUCING PROTEIN BY PRECIPITATION

CROSS-REFERENCE TO RELATED APPLICATIONS

The present application is a continuation of and claims the benefits of priority to U.S. application Ser. No 14/539.562, filed Nov. 12, 2014, which is a continuation of and claims the benefits of priority to International Application No. PCTIP2014/053810, filed Feb. 18, 2014, which claims the benefits of priority to Japanese Application No. 2013-029397, filed Feb. 18, 2013. The entire contents of these applications are incorporated herein by reference.

TECHNICAL FIELD

The present invention relates to a method for producing a protein by precipitation. More specifically, the present invention relates to methods for producing a fusion protein and a target protein by adjusting a pH of a solution containing the fusion protein made of the target protein and a protein having a self-assembly capability.

BACKGROUND ART

Proteins having a variety of functions are widely utilized for commercial uses such as pharmaceutical products and industrial enzymes, and also for research uses in which proteins are used to elucidate various biological phenomena. Thus, proteins are substances essential in improvements in quality of life and scientific advancements. As means for producing these various proteins in large quantities at a low cost with a high reproducibility, techniques for producing proteins using recombinant organisms and techniques for purifying the proteins have been developed.

The techniques for producing proteins using recombinant organisms utilize animal cells (Non-Patent Literature 1) and microorganisms (Non-Patent Literature 1). The animal cells used include CHO cells (Non-Patent Literature 2), while the microorganisms used include *Escherichia coli*, yeasts (Non-Patent Literature 3), and the like. For example, there is a protein secretory production system using *Corynebacterium glutamicum* (hereinafter may be abbreviated as *C. glutamicum*) as the microorganism (Patent Literature 1).

Main methods for purifying proteins produced by recombinant organisms include a method utilizing properties of a protein itself, and a method by adding a sequence used for purification to a protein and utilizing properties of the added sequence.

The method utilizing properties of a protein itself includes chromatography and liquid-solid separation.

The chromatography uses chromatographic matrixes having various properties. The chromatography utilizes an interaction between a protein and a chromatographic matrix, or the molecular sieving effect of the chromatographic matrix (Non-Patent Literature 4). The interaction between a protein and a chromatographic matrix includes electrostatic interaction, hydrogen bond, hydrophobic interaction, specific interaction, and the like (Non-Patent Literatures 4 and 5).

The liquid-solid separation is a separation method including: insolubilizing (i.e., making solid) a protein in a solubilized state by changing the solution conditions, obtaining a solid component by a simple process such as centrifugation, and bringing the separated solid component into a solubilized state again. Specific examples of the means for insolubilizing the protein include isoelectric point precipitation (Non-Patent Literature 6), salting out (Non-Patent Literature 7), precipitation using an organic solvent (Non-Patent Literature 8), precipitation using a water-soluble polymer (Non-Patent Literature 9), and the like.

The isoelectric point precipitation utilizes a property in which the solubility of a protein becomes lowest at an isoelectric point thereof. The salting out, the precipitation using an organic solvent, and the precipitation using a water-soluble polymer utilize a property in which the solubility of a protein is decreased in the presence of the salt, the organic solvent, or the water-soluble polymer, each of which is at a high concentration. Another insolubilizing means is protein aggregation (Non-Patent Literatures 10 and 11). The protein aggregation may be particularly effective means when it is possible to select conditions for aggregating a protein other than a protein to be purified while leaving the protein to be purified in a solubilized state.

The method by adding a sequence used for purification to a protein and utilizing properties of the added sequence includes a method utilizing properties of the added sequence itself, and a method utilizing an interaction between the added sequence and a substance other than the added sequence.

The method utilizing properties of the added sequence itself includes a method utilizing elastin, which undergoes a phase transition to become insoluble with the temperature change (Non-Patent Literature 12), a method utilizing MISTIC, which forms a soluble assembly with the pH change (Patent Literature 2), and the like.

In the method utilizing an interaction between the added sequence and a substance other than the added sequence, the substance other than the added sequence is often disposed on a chromatographic matrix (Non-Patent Literature 13). The interaction between the added sequence and the substance other than the added sequence includes electrostatic interaction, hydrogen bond, hydrophobic interaction, specific interaction, and the like.

CITATION LIST

Patent Literatures

Patent Literature 1: International Patent Application Publication No. WO2005/103278
Patent Literature 2: European Patent Application Publication No. 2423217

Non-Patent Literature

Non-Patent Literature 1: Demain AL, and Vaishnav P., Production of recombinant proteins by microbes and higher organisms. Biotechnol Adv. 2009 May-June; 27 (3): 297-306. Epub 2009 Jan. 31. Review.
Non-Patent Literature 2: Omasa T, Onitsuka M, and Kim W D., Cell engineering and cultivation of chinese hamster ovary (CHO) cells. Curr Pharm Biotechnol. 2010 April; 11 (3): 233-40. Review.
Non-Patent Literature 3: Mattanovich D, Branduardi P, Dato L, Gasser B, Sauer M, and Porro D., Recombinant protein production in yeasts. Methods Mol Biol. 2012; 824: 329-58. Review.
Non-Patent Literature 4: Watanabe E, Tsoka S, and Asenjo J A., Selection of chromatographic protein purification operations based on physicochemical properties. Ann N Y Acad Sci. 1994 May 2; 721: 348-64.
Non-Patent Literature 5: Hober S, Nord K, and Linhult M., Protein A chromatography for antibody purification.

J Chromatogr B Analyt Technol Biomed Life Sci. 2007 Mar. 15; 848 (1): 40-7. Epub 2006 Oct 9. Review.

Non-Patent Literature 6: Garcia, F. A. P., Protein precipitation. Recovery Processes Biol. Mater. (1993), 355-67.

Non-Patent Literature 7: A. A. Green: J. Biol. Chem., 95, 47 (1932)

Non-Patent Literature 8: McCord JM, and Fridovich I., Superoxide dismutase. An enzymic function for erythrocuprein (hemocuprein). J Biol Chem. 1969 Nov. 25; 244 (22): 6049-55.

Non-Patent Literature 9: Ingham K C., Protein precipitation with polyethylene glycol. Methods Enzymol. 1984; 104: 351-6.

Non-Patent Literature 10: Cromwell ME, Hilario E, and Jacobson F., Protein aggregation and bioprocessing. AAPS J. 2006 Sep 15; (3): E572-9

Non-Patent Literature 11: Mahler HC, Friess W, Grauschopf U, and Kiese S., J Pharm Sci. 2009 September; 98 (9): 2909-34. Protein aggregation: pathways, induction factors and analysis.

Non-Patent Literature 12: Hassouneh W, Christensen T, and Chilkoti A., Elastin-like polypeptides as a purification tag for recombinant proteins. Curr Protoc Protein Sci. 2010 August; Chapter 6: Unit 6.11.

Non-Patent Literature 13: Smyth DR, Mrozkiewicz MK, McGrath WJ, Listwan P, and Kobe B., Crystal structures of fusion proteins with large-affinity tags. Protein Sci. 2003 July; 12 (7): 1313-22.

SUMMARY OF INVENTION

Technical Problems

In the method utilizing properties of a protein itself, a purification process is constructed for each target protein in accordance with properties of the target protein. Hence, it is generally impossible to employ a purification process for a certain protein directly as a purification process for another protein.

On the other hand, the method by adding a sequence used for purification to a protein and utilizing properties of the added sequence can be said to be a widely applicable method, because the same or similar purification process using an added sequence of the same kind can be employed to purify multiple proteins in many cases.

Nevertheless, such a method utilizing properties of an added sequence also has problems: for example, the method utilizing elastin cannot be employed for a target protein that is likely to be inactivated by heat; and the method utilizing MISTIC has difficulty separating an assembly formed.

Solution to Problems

The present inventors have earnestly studied to solve the above-described problems. As a result, the inventors have unexpectedly found out that when a protein having a self-assembly capability is used as a sequence to be added, a fusion protein made of the added sequence and the target protein has such a property that the fusion protein is reversibly changeable between a solubilized state and an insolubilized state in a solution in a pH dependent manner. The present invention has been made based on this finding.

Specifically, the present invention relates to the following [1] to [33].

[1] A method for producing a fusion protein made of a protein having a self-assembly capability and a target protein, comprising the following steps (1) to (4):

(1) preparing a solution containing the fusion protein;

(2) adjusting a pH of the solution obtained in step (1) to such a pH that a recovery ratio calculated according to the following equation is 10% or more, where the recovery ratio (%)=[an amount of the fusion protein in a solution obtained in step (4)/{the amount of the fusion protein in the solution obtained in step (4)+an amount of the fusion protein in a solution after solid separation in step (3)}]×100;

(3) separating a solid from the solution obtained instep (2); and (4) dissolving the solid separated in step (3) into a solution having a pH of 12 or below but higher than the pH of the solution obtained in step (2) by 0.1 or more.

[2] The method according to [1], in which the protein having a self-assembly capability is a cell surface protein.

[3] The method according to [2], in which the cell surface protein is a CspB mature protein or a portion thereof.

[4] The method according to [3], in which the CspB mature protein or the portion thereof is any one of the following (a) and (b):

(a) a protein consisting of an amino acid sequence of SEQ ID NO: 3; and (b) a protein having a homology of 95% or more with the amino acid sequence of SEQ ID NO: 3.

[5] The method according to [3], in which the portion of the CspB mature protein is a sequence consisting of 6 to 250 amino acid residues from the N-terminus of the CspB mature protein.

[6] The method according to [5], in which the portion of the CspB mature protein is a sequence consisting of 6, 17, 50, or 250 amino acid residues from the N-terminus of the CspB mature protein.

[7] The method according to any one of [1] to [6], in which the number of amino acid residues in the target protein is 10 to 1000.

[8] The method according to any one of [1] to [7], in which an amino acid sequence used for an enzymatic cleavage or a chemical cleavage is further incorporated between the protein having a self-assembly capability and the target protein.

[9] The method according to [8], in which the amino acid sequence used for the enzymatic cleavage between the protein having a self-assembly capability and the target protein is a ProTEV protease recognition sequence, a trypsin recognition sequence, or a Factor Xa protease recognition sequence.

[10] The method according to any one of [1] to [9], in which the pH in step (2) is 9 or below.

[11] The method according to any one of [1] to [10], in which the pH is adjusted in step (2) using an acid selected from the group consisting of sulfuric acid, hydrochloric acid, acetic acid, phosphoric acid, and trifluoroacetic acid.

[12] The method according to any one of [1] to [11], in which the separation instep (3) is performed by centrifugation and/or membrane filtration.

[13] The method according to any one of [1] to [12], in which the solution obtained in step (1) is a supernatant of a culture solution of a coryneform bacterium having a gene construct capable of expressing the fusion protein.

[14] The method according to any one of [1] to [13], in which the recovery ratio specified in step (2) is 30% or more.

[15] A method for producing a target protein, comprising the following steps (1) to (5):

(1) preparing a solution containing a fusion protein made of a protein having a self-assembly capability and the target protein, the fusion protein containing an amino acid sequence used for an enzymatic cleavage or a chemical cleavage between the protein having a self-assembly capability and the target protein;

(2) adjusting a pH of the solution obtained in step (1) to such a pH that a recovery ratio calculated according to the following equation is 10% or more, where the recovery ratio (%)=[an amount of the fusion protein in a solution obtained in step (4)/{the amount of the fusion protein in the solution obtained in step (4)+an amount of the fusion protein in a solution after solid separation in step (3)}]×100;

(3) separating a solid from the solution obtained in step (2);

(4) dissolving the solid separated in step (3) into a solution having a pH of 12 or below but higher than the pH of the solution obtained in step (2) by 0.1 or more; and (5) enzymatically or chemically cleaving the fusion protein at a site of the amino acid sequence between the protein having a self-assembly capability and the target protein simultaneously with step (4), during step (4), or after step (4).

[16] The method according to [15], in which the step of cleaving the fusion protein is an enzymatically cleaving step.

[17] The method according to [15], in which the protein having a self-assembly capability is a cell surface protein.

[18] The method according to [17], in which the cell surface protein is a CspB mature protein or a portion thereof.

[19] The method according to [18], in which the CspB mature protein or the portion thereof is any one of the following (a) and (b):
 (a) a protein consisting of an amino acid sequence of SEQ ID NO: 3; and
 (b) a protein having a homology of 95% or more with the amino acid sequence of SEQ ID NO: 3.

[20] The method according to [18], in which the portion of the CspB mature protein is a sequence consisting of 6 to 250 amino acid residues from the N-terminus of the CspB mature protein.

[21] The method according to [20], in which the portion of the CspB mature protein is a sequence consisting of 6, 17, 50, or 250 amino acid residues from the N-terminus of the CspB mature protein.

[22] The method according to any one of [15] to [21], in which the number of amino acid residues in the target protein is 10 to 1000.

[23] The method according to any one of [15] to [22], in which the target protein is teriparatide.

[24] The method according to any one of [15] to [22], in which the target protein is a bivalirudin intermediate represented by SEQ ID NO: 93.

[25] The method according to any one of [15] to [24], in which the amino acid sequence used for the enzymatic cleavage between the protein having a self-assembly capability and the target protein is a ProTEV protease recognition sequence, a trypsin recognition sequence, or a Factor Xa protease recognition sequence.

[26] The method according to any one of [15] to [25], in which the pH in step (2) is 9 or below.

[27] The method according to any one of [15] to [26], in which the pH is adjusted in step (2) using an acid selected from the group consisting of sulfuric acid, hydrochloric acid, acetic acid, phosphoric acid, and trifluoroacetic acid.

[28] The method according to any one of [15] to [27], in which the separation in step (3) is performed by centrifugation and/or membrane filtration.

[29] The method according to any one of [15] to [28], in which the solution obtained in step (1) is a supernatant of a culture solution of a coryneform bacterium having a gene construct capable of expressing the fusion protein.

[30] The method according to any one of [15] to [29], comprising a step of (6) purifying the fusion protein or the target protein after step (4) and/or step (5).

[31] The method according to [30], in which step (6) is performed by column chromatography.

[32] The method according to any one of [15] to [31], in which the recovery ratio specified in step (2) is 30% or more.

[33] A method for forming and separating a solid of a fusion protein made of a protein having a self-assembly capability and a target protein, the method comprising:
 forming the solid by adjusting a pH of a solution containing the fusion protein to 9 or below; and
 then separating the solid.

Advantageous Effects of Invention

As described in Examples later, the present invention makes it possible to obtain a fusion protein containing a target protein or the target protein from a solution containing the fusion protein easily at a high recovery ratio.

BRIEF DESCRIPTION OF DRAWINGS

FIG. 1-A shows the relation between the pH of "pH-adjusted culture solutions" and the recovery ratio of a fusion protein CspB50TEV-Teriparatide (abbreviated as 50-Teri) in Example 1.

FIG. 1-B shows the pH of the "pH-adjusted culture solutions," photographs of band portions of the fusion protein 50-Teri in images of electrophoresis of "supernatants of the pH-adjusted culture solutions" and the corresponding "precipitate-dissolved solutions," and the recovery ratio in Example 1.

FIG. 1-2A shows the relation between the pH of "pH-adjusted culture solutions" and the recovery ratio of a fusion protein 50-Teri in Example 1-2.

FIG. 1-2B shows images of electrophoresis of the "pH-adjusted culture solutions" and the corresponding "precipitate-dissolved solutions," and photographs of extracted band portions of the fusion protein 50-Teri in Example 1-2.

FIG. 1-2C shows chromatograms obtained by subjecting the "supernatant of the pH-adjusted culture solution" having a pH adjusted to 4.9 and the corresponding "precipitate-dissolved solution" to reversed-phase HPLC in Example 1-2.

FIG. 1-2D shows chromatograms obtained by subjecting the "precipitate-dissolved solution," which was prepared from the "pH-adjusted culture solution" having a pH adjusted to 4.9, an "enzymatic cleavage solution," and "standard Teriparatide" to reversed-phase HPLC in Example 1-2.

FIG. 1-2E shows a chart of amass spectrum obtained by subjecting a "purified substance," which was prepared by purifying the "pH-adjusted culture solution" having a pH adjusted to 4.9, and "standard Teriparatide" to mass spectrometry in Example 1-2.

FIG. 2-A shows the relation between the pH of "pH-adjusted culture solutions" and the recovery ratio of a fusion protein CspB50Lys-Bivalirudin18 (abbreviated as 50-Biva18) in Example 2.

FIG. 2-B shows the pH of the "pH-adjusted culture solutions," photographs of band portions of the fusion protein 50-Biva18 in images of electrophoresis of "supernatants of the pH-adjusted culture solutions" and the corresponding "precipitate-dissolved solutions," and the recovery ratio in Example 2.

FIG. 2-C shows chromatograms obtained by subjecting the "supernatant of the pH-adjusted culture solution" having a pH adjusted to 2.9 and the corresponding "precipitate-dissolved solution" to reversed-phase HPLC in Example 2.

FIG. 2-D shows chromatograms obtained by subjecting the "precipitate-dissolved solution," which was prepared from the "pH-adjusted culture solution" having a pH adjusted to 2.9, and an "enzymatic cleavage solution" to reversed-phase HPLC in Example 2.

FIG. 2-E shows a mass (upper left part) calculated from the amino acid sequence of Biva18, a theoretical mass spectrum (upper right part) of the calculated mass and a chart (lower part) of a mass spectrum obtained by subjecting a "purified substance," which was prepared by purifying the "pH-adjusted culture solution" having a pH adjusted to 2.9, to mass spectrometry in Example 2.

FIG. 2-F shows a chromatogram obtained by subjecting an "enzymatic cleavage solution" prepared from the "pH-adjusted culture solution" having a pH adjusted to 2.9 to strong anion exchange resin chromatography in Example 2.

FIG. 2-G shows a chromatogram obtained by subjecting an eluate (around 95% B) to reversed-phase HPLC, the eluate prepared by subjecting the "enzymatic cleavage solution" prepared from the "pH-adjusted culture solution" having a pH adjusted to 2.9 to strong anion exchange resin chromatography in Example 2.

FIG. 3-A shows the relation between the pH of "pH-adjusted culture solutions" and the recovery ratio of a fusion protein CspB50TEV-Proinsulin (abbreviated as 50-PIns) in Example 3.

FIG. 3-B shows the pH of "pH-adjusted culture solutions," photographs of band portions of the fusion protein 50-PIns in images of electrophoresis of "supernatants of the pH-adjusted culture solutions" and the corresponding "precipitate-dissolved solutions," and the recovery ratio in Example 3.

FIG. 4-A shows the relation between the pH of "pH-adjusted culture solutions" and the recovery ratio of proinsulin (abbreviated as PIns) in Comparative Example 1.

FIG. 4-B shows the pH of the "pH-adjusted culture solutions," photographs of band portions of PIns in images of electrophoresis of "supernatants of the pH-adjusted culture solutions" and the corresponding "precipitate-dissolved solutions," and the recovery ratio in Comparative Example 1.

FIG. 5-A shows the relation between the pH of "pH-adjusted culture solutions" and the recovery ratio of a fusion protein CspB250TEV-Proinsulin (abbreviated as 250-PIns) in Example 4.

FIG. 5-B shows the pH of the "pH-adjusted culture solutions," photographs of band portions of the fusion protein 250-PIns in images of electrophoresis of "supernatants of the pH-adjusted culture solutions" and the corresponding "precipitate-dissolved solutions," and the recovery ratio in Example 4.

FIG. 6-A shows the relation between the pH of "pH-adjusted culture solutions" and the recovery ratio of a fusion protein CspB17TEV-Proinsulin (abbreviated as 17-PIns) in Example 5.

FIG. 6-B shows the pH of the "pH-adjusted culture solutions," photographs of band portions of the fusion protein 17-PIns in images of electrophoresis of "supernatants of the pH-adjusted culture solutions" and the corresponding "precipitate-dissolved solutions," and the recovery ratio in Example 5.

FIG. 7-A shows the relation between the pH of "pH-adjusted culture solutions" and the recovery ratio of a fusion protein CspB6TEV-Proinsulin (abbreviated as 6-PIns) in Example 6.

FIG. 7-B shows the pH of the "pH-adjusted culture solution," photographs of band portions of the fusion protein 6-PIns in images of electrophoresis of "supernatants of the pH-adjusted culture solutions" and the corresponding "precipitate-dissolved solutions," and the recovery ratio in Example 6.

FIG. 8-A shows the relation between the pH of "pH-adjusted culture solutions" and the recovery ratio of a fusion protein CspB50TEV-Teriparatide (abbreviated as 50-Teri) in Example 7.

FIG. 8-B shows the pH of the "pH-adjusted culture solutions," photographs of band portions of the fusion protein 50-Teri in images of electrophoresis of "supernatants of the pH-adjusted culture solutions" and the corresponding "precipitate-dissolved solutions," and the recovery ratio in Example 7.

FIG. 9-A shows the relation between the pH of "pH-adjusted culture solutions" and the recovery ratio of a fusion protein CspB50TEV-Teriparatide (abbreviated as 50-Teri) in Example 8.

FIG. 9-B shows the pH of the "pH-adjusted culture solutions," photographs of band portions of the fusion protein 50-Teri in images of electrophoresis of "supernatants of the pH-adjusted culture solutions" and the corresponding "precipitate-dissolved solutions," and the recovery ratio in Example 8.

FIG. 10-A shows chromatograms obtained by subjecting the "microbial cell-removed culture solution" (corresponding to "solution obtained in step (1)") and the "precipitate-dissolved solution" (corresponding to "solution obtained in step (4)") in Example 9 to reversed-phase HPLC (measuring wavelength: 280 nm).

FIG. 10-B shows chromatograms obtained by subjecting the "microbial cell-removed culture solution" (corresponding to "solution obtained in step (1)") and the "precipitate-dissolved solution" (corresponding to "solution obtained in step (4)") in Example 9 to reversed-phase HPLC (measuring wavelength: 220 nm).

DESCRIPTION OF EMBODIMENTS

Figures 1, 2, 2A:
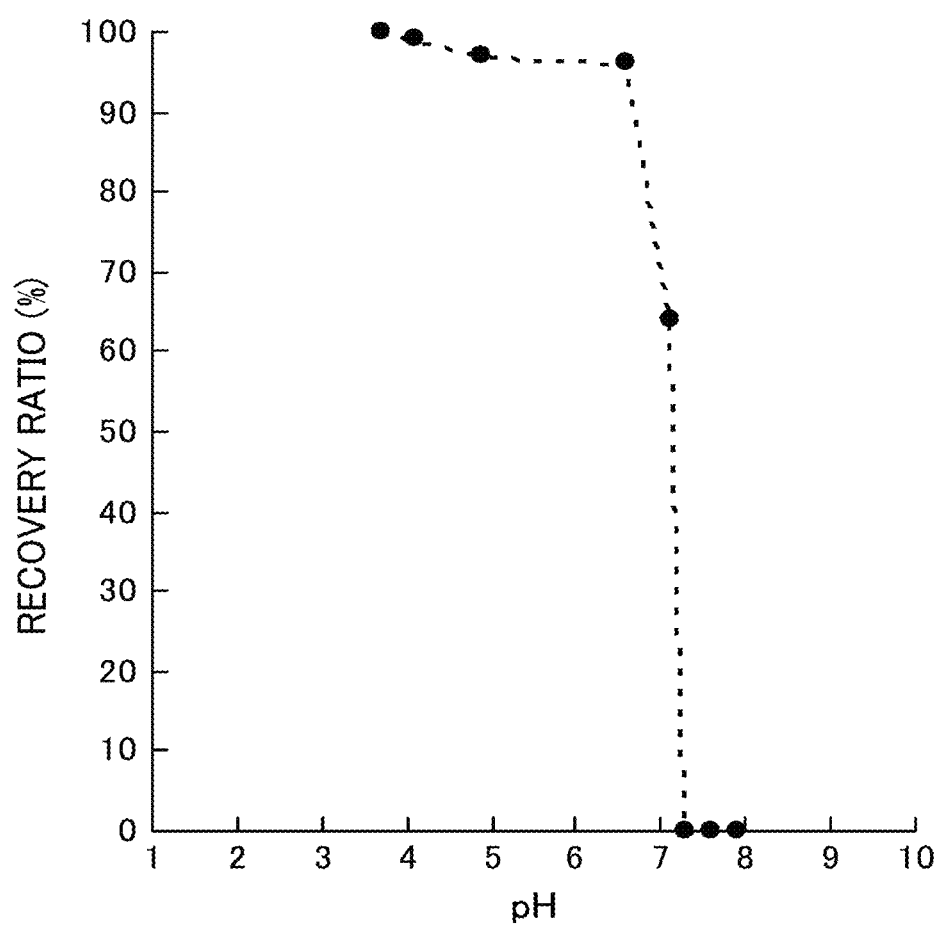

A production method of the present invention is similar to one type of a method by adding a sequence used for purification (hereinafter may also be sometimes referred to as "added sequence") to a protein and utilizing properties of the added sequence, that is, a method utilizing the properties of the added sequence itself. In the present invention, a sequence of a protein having a self-assembly capability is used as the added sequence.

An embodiment of the present invention is a method for producing a fusion protein made of a protein having a self-assembly capability and a target protein, comprising the following steps (1) to (4):

(1) preparing a solution containing the fusion protein;
(2) adjusting a pH of the solution obtained in step (1) to such a pH that a recovery ratio calculated according to the following equation is 10% or more, where the recovery ratio (%)=[an amount of the fusion protein in a solution obtained in step (4)/{the amount of the fusion protein in the solution obtained in step (4)+an amount of the fusion protein in a solution after solid separation in step (3)}]×100;

(3) separating a solid from the solution obtained in step (2); and (4) dissolving the solid separated in step (3) into a solution having a pH of 12 or below but higher than the pH of the solution obtained in step (2) by 0.1 or more.

In step (1) of the production method of the present invention, a solution containing a fusion protein made of a protein having a self-assembly capability and a target protein is prepared.

The "fusion protein" is composed of the "protein having a self-assembly capability" and the "target protein". The "protein having a self-assembly capability" may be located upstream (the N-terminal side) or downstream (the C-terminal side) of the "target protein." Note that, as will be described later, the fusion protein may contain an "amino acid sequence used for a cleavage" between the amino acid sequence of the "protein having a self-assembly capability" and the amino acid sequence of the "target protein."

The "self-assembly capability" refers to an ability of a protein itself to assemble under appropriate environmental conditions to thereby form a physiologically meaningful higher-order structure.

The "protein having a self-assembly capability" may be a full length sequence or a partial sequence, as long as the self-assembly capability is retained.

The size (the number of amino acid residues) of the "protein having a self-assembly capability" is not particularly limited, as long as the self-assembly capability is retained. The number of the amino acid residues is preferably 5 to 1000 amino acids, more preferably 5 to 700 amino acids, and further preferably 5 to 500 amino acids.

The "protein having a self-assembly capability" may be a variant of a naturally-occurring protein, as long as the self-assembly capability is retained. For example, in the amino acid sequence of a naturally-occurring protein, one or more amino acids may be substituted, deleted, inserted, or added. The phrase "one or more" means preferably 1 to 20, more preferably 1 to 10, and further preferably 1 to 5, although the number varies depending on the position of the amino acid residues in the conformation of the protein and the type of the amino acid residues.

The substitution, deletion, insertion, or addition of the amino acid may be a conservative mutation such that the self-assembly capability of the protein is normally maintained. The conservative mutation is typically a conservative substitution. The conservative substitution is a mutation by which: Phe, Trp, and Tyr are substituted for each other in a case where the substitution site is an aromatic amino acid; Leu, Ile, and Val are substituted for each other in a case where the substitution site is a hydrophobic amino acid; Gln and Asn are substituted for each other in a case of a polar amino acid; Lys, Arg, and His are substituted for each other in a case of a basic amino acid; Asp and Glu are substituted for each other in a case of an acidic amino acid; and Ser and Thr are substituted for each other in a case of an amino acid having a hydroxyl group. The substitution regarded as the conservative substitution specifically includes a substitution of Ala with Ser or Thr, a substitution of Arg with Gln, His, or Lys, a substitution of Asn with Glu, Gln, Lys, His, or Asp, a substitution of Asp with Asn, Glu, or Gln, a substitution of Cys with Ser or Ala, a substitution of Gln with Asn, Glu, Lys, His, Asp, or Arg, a substitution of Glu with Gly, Asn, Gln, Lys, or Asp, a substitution of Gly with Pro, a substitution of His with Asn, Lys, Gln, Arg, or Tyr, a substitution of Ile with Leu, Met, Val, or Phe, a substitution of Leu with Ile, Met, Val, or Phe, a substitution of Lys with Asn, Glu, Gln, His, or Arg, a substitution of Met with Ile, Leu, Val, or Phe, a substitution of Phe with Trp, Tyr, Met, Ile, or Leu, a substitution of Ser with Thr or Ala, a substitution of Thr with Ser or Ala, a substitution of Trp with Phe or Tyr, a substitution of Tyr with His, Phe, or Trp, and a substitution of Val with Met, Ile, or Leu. Additionally, the substitution, deletion, insertion, or addition of the amino acid includes those caused in a naturally-occurring variant based on individual differences in a bacterium from which a gene encoding the protein is derived, differences in species, or the like.

The variant of a naturally-occurring protein may have a homology of 95% or more, further preferably 97% or more, and particularly preferably 99% or more, with the entire amino acid sequence of the naturally-occurring protein, as long as the variant has a self-assembly capability. Note that, herein, the "homology" may also mean an "identity".

Moreover, the gene encoding the "protein having a self-assembly capability" may be a DNA hybridizing under stringent conditions with a probe that can be prepared from a known gene sequence, for example, a sequence complementary to all or part of the base sequence, as long as the encoded protein has a self-assembly capability. The "stringent conditions" refer to conditions under which a so-called specific hybrid is formed, but a non-specific hybrid is not formed. Examples thereof include conditions under which DNAs having a high homology with each other, for example DNAs having a homology of 80% or more, preferably 90% or more, more preferably 95% or more, further preferably 97% or more, and particularly preferably 99% or more hybridize with each other, but DNAs having lower homology than these do not hybridize with each other; and conditions under which washing is performed once, preferably two or three times, at a temperature and salt concentrations of ordinal southern hybridization washing conditions, that is, 60° C., 1×SSC, 0.1% SDS, preferably 60° C., 0.1×SSC, 0.1% SDS, and more preferably 68° C., 0.1×SSC, 0.1% SDS.

The probe used in the hybridization may be a part of the sequence complementary to the gene. Such a probe can be produced by PCR using as primers oligonucleotides prepared based on a known gene sequence, and using as a template a DNA fragment containing the base sequences of these. For example, when a DNA fragment of approximately 300 by in length is used as the probe, the hybridization washing conditions include 50° C., 2×SSC, 0.1% SDS.

The gene encoding the "protein having a self-assembly capability" can be used in a naturally-occurring form, or may be modified so as to have optimum codons in accordance with the codon usage in a host to be used.

Specific examples of the "protein having a self-assembly capability" include cell surface proteins, viral envelope proteins, various motor proteins, and the like.

A cell surface protein is a component protein of a cell surface structure, called an S-layer, widely found in bacteria, and is known to self-assemble and forma layered structure under physiological conditions (Ilk N, Egelseer EM, and Sleytr UB. S-layer fusion proteins--construction principles and applications. Curr Opin Biotechnol. 2011 December; 22 (6): 824-31. Epub 2011 Jun 21.).

Specific examples of the cell surface proteins include PS1 and CspB (PS2) derived from a coryneform bacterium *C. glutamicum* (Published Japanese Translation of PCT Internal Application No. (JP-A) Hei 6-502548), SlpA (CspA) derived from *Corynebacterium ammoniagenes* (Japanese Patent Application Publication No. (JP-A) Hei 10-108675), and the like.

Among these, CspB (PS2) (499 amino acid residues) is preferable. Note that CspB is the same as PS2.

CspB is a cell surface protein found in *C. glutamicum* (Peyret J L, Bayan N, Joliff G, Gulik-Krzywicki T, Mathieu L, Schechter E, and Leblon G., Characterization of the cspB gene encoding PS2, an ordered surface-layer protein in *Corynebacterium glutamicum*. Mol Microbiol. 1993 July; 9 (1): 97-109).

As to CspB, it has been found out in various types of *C. glutamicum* that treating the microbial cells with a solution containing a surfactant sodium dodecyl sulfate (SDS) disrupts the self-assembled layered structure, and CspB is extracted into the SDS solution (Hansmeier N, Bartels F W, Ros R, Anselmetti D, Tauch A, Puhler A., and Kalinowski J. Classification of hyper-variable *Corynebacterium glutamicum* surface-layer proteins by sequence analyses and atomic force microscopy. J Biotechnol. 2004 Aug. 26; 112 (1-2): 177-93).

A specific example of CspB includes CspB of *C. glutamicum* ATCC13869. The base sequence of a cspB gene of *C. glutamicum* ATCC13869 is shown in SEQ ID NO: 1, and the amino acid sequence of a CspB protein is shown in SEQ ID NO: 2. In the amino acid sequence shown in SEQ ID NO: 2, amino acid residues at positions 1 to 30 correspond to a signal peptide, and amino acid residues at positions 31 to 499 correspond to a CspB mature protein (hereinafter may also be referred to as either "mature CspB" or "CspB mature protein"). The amino acid sequence of the CspB mature protein of *C. glutamicum* ATCC13869 wherein the 30 amino acid residues of the signal peptide portion are excluded is shown in SEQ ID NO: 3.

```
                                              SEQ ID NO: 3
Gln Glu Thr Asn Pro Thr Phe Asn Ile Asn Asn Gly

Phe Asn Asp Ala Asp Gly Ser Thr Ile Gln Pro Val

Glu Pro Val Asn His Thr Glu Glu Thr Leu Arg Asp

Leu Thr Asp Ser Thr Gly Ala Tyr Leu Glu Glu Phe

Gln Tyr Gly Asn Val Glu Glu Ile Val Glu Ala Tyr

Leu Gln Val Gln Ala Ser Ala Asp Gly Phe Asp Pro

Ser Glu Gln Ala Ala Tyr Glu Ala Phe Glu Ala Ala

Arg Val Arg Ala Ser Gln Glu Leu Ala Ala Ser Ala

Glu Thr Ile Thr Lys Thr Arg Glu Ser Val Ala Tyr

Ala Leu Lys Ala Asp Arg Glu Ala Thr Ala Ala Phe

Glu Ala Tyr Leu Ser Ala Leu Arg Gln Val Ser Val

Ile Asn Asp Leu Ile Ala Asp Ala Asn Ala Lys Asn

Lys Thr Asp Phe Ala Glu Ile Glu Leu Tyr Asp Val

Leu Tyr Thr Asp Ala Asp Ile Ser Gly Asp Ala Pro

Leu Leu Ala Pro Ala Tyr Lys Glu Leu Lys Asp Leu

Gln Ala Glu Val Asp Ala Asp Phe Glu Trp Leu Gly

Glu Phe Ala Ile Asp Asn Asn Glu Asp Asn Tyr Val

Ile Arg Thr His Ile Pro Ala Val Glu Ala Leu Lys

Ala Ala Ile Asp Ser Leu Val Asp Thr Val Glu Pro

Leu Arg Ala Asp Ala Ile Ala Lys Asn Ile Glu Ala

Gln Lys Ser Asp Val Leu Val Pro Gln Leu Phe Leu

Glu Arg Ala Thr Ala Gln Arg Asp Thr Leu Arg Val

Val Glu Ala Ile Phe Ser Thr Ser Ala Arg Tyr Val

Glu Leu Tyr Glu Asn Val Glu Asn Val Asn Val Glu

Asn Lys Thr Leu Arg Gln His Tyr Ser Ser Leu Ile

Pro Asn Leu Phe Ile Ala Ala Val Gly Asn Ile Asn

Glu Leu Asn Asn Ala Asp Gln Ala Ala Arg Glu Leu

Phe Leu Asp Trp Asp Thr Asp Leu Thr Thr Asn Asp

Glu Asp Glu Ala Tyr Tyr Gln Ala Lys Leu Asp Phe

Ala Ile Glu Thr Tyr Ala Lys Ile Leu Ile Asn Gly

Glu Val Trp Gln Glu Pro Leu Ala Tyr Val Gln Asn

Leu Asp Ala Gly Ala Arg Gln Glu Ala Ala Asp Arg

Glu Ala Glu Arg Ala Ala Asp Ala Ala Tyr Arg Ala

Glu Gln Leu Arg Ile Ala Gln Glu Ala Ala Asp Ala

Gln Lys Ala Leu Ala Glu Ala Leu Ala Asn Ala Gly

Asn Asn Asp Asn Gly Gly Asp Asn Ser Ser Asp Asp

Lys Gly Thr Gly Ser Ser Asp Ile Gly Thr Trp Gly

Pro Phe Ala Ala Ile Ala Ala Ile Ile Ala Ala Ile

Ala Ala Ile Phe Pro Phe Leu Ser Gly Ile Val Lys

Phe
```

CspB used in the present invention is preferably a CspB mature protein, more preferably a portion of the CspB mature protein. Particularly, CspB used in the present invention preferably is a sequence consisting of 6 to 250 amino acid residues from the N-terminus of the CspB mature protein from the standpoint of the recovery ratio of the fusion protein. The "sequence consisting of 6 to 250 amino acid residues from the N-terminus" is an amino acid sequence from an amino acid residue at position 1 at the N-terminus to an amino acid residue at any one of positions 6 to 250 (any one of 6th to 250th amino acid residues from the same N-terminus).

For example, in a case where the CspB mature protein is the protein consisting of an amino acid sequence shown in SEQ ID NO: 3, the "sequence consisting of 6 to 250 amino acid residues from the N-terminus" is an amino acid sequence from an amino acid residue at position 1 (the N-terminus) of SEQ ID NO: 3 to an amino acid residue at any one of positions 6 to 250 (any one of 6th to 250th amino acid residues from the same N-terminus).

Further preferably, CspB used in the present invention is a sequence consisting of 6, 17, 50, or 250 amino acid residues from the N-terminus of the CspB mature protein.

It should be noted that the phrase "position X (X is for example 6, 17, 50, or 250)" in an amino acid sequence means the Xth position from the N-terminus in the amino acid sequence, and an amino acid residue at the N-terminus is an amino acid residue at position 1. Namely, the positions of the aforementioned amino acid residues show relative positions, and therefore the positions may change slightly by a deletion, insertion, addition, or the like of an amino acid.

For example, in a case where the CspB mature protein is the protein consisting of an amino acid sequence shown in SEQ ID NO: 3, the "amino acid residue at position 50 from the N-terminus" means an amino acid residue corresponding to one at position 50 in SEQ ID NO: 3. If one amino acid residue is deleted between position 49 and the N-terminus, the 49th amino acid residue from the N-terminus is the "amino acid residue at position 50 from the N-terminus." In addition, if one amino acid residue is inserted between position 50 and the N-terminus, the 51st amino acid residue from the N-terminus is the "amino acid residue at position 50 from the N-terminus."

The nucleic acid sequence of the cspB gene varies, depending on the species to which a coryneform bacterium belongs or the strain thereof. Thus, the cspB gene may be a variant of the nucleic acid sequence, as long as the encoded protein has a self-assembly capability. The variant of the cspB gene includes homologues of the gene. The homologues of the cspB gene can be easily obtained, for example, from a publicly-available database by a BLAST search or a FASTA search using the above-described cspB gene (SEQ ID NO: 1) of *C. glutamicum* ATCC13869 as a query sequence. The homologues of the cspB gene can also be obtained by PCR using a chromosome of the coryneform bacterium as a template, and using as primers oligonucleotides prepared based on these known gene sequences.

The "target protein" includes any naturally-occurring proteins derived from microorganisms, plants, animals, or viruses, and proteins whose amino acid sequences are artificially designed, without particular limitations.

In addition, the "target protein" may be a homologous protein or a heterologous protein in relation to a host producing the protein.

The target protein may be a monomeric protein or a multimeric protein (multimer).

The multimeric protein refers to a protein existing as a multimer composed of two or more subunits. In a multimer, each subunit may be linked to the other(s) by a covalent bond such as a disulfide bond, or linked by a non-covalent bond such as a hydrogen bond or hydrophobic interaction, or linked by a combination of these. The multimer may be a homomultimer composed of the same type of subunits, or a heteromultimer composed of two or more types of subunits. Incidentally, in a case where the multimeric protein is a heteromultimer, at least one subunit among subunits composing the multimer may be a heterologous protein. In other words, all the subunits may be derived from different species, or only some subunits may be derived from different species.

The target protein may be a naturally-occurring secretory protein, or a naturally-occurring non-secretory protein. A naturally-occurring secretory protein is preferable.

The number of types of the target protein produced according to the present invention may be only one or may be two or more. Moreover, in a case where the target protein is a heteromultimer, only one type of subunits may be produced, or two or more types of subunits may be produced.

The size (the number of amino acid residues) of the target protein is not particularly limited, as long as it can be expressed in a host to be used. The number of the amino acid residues is preferably 10 to 1000, more preferably 10 to 500, and further preferably 10 to 300.

The target protein may be a variant of the naturally-occurring protein. The above description of the variant related to the "protein having a self-assembly capability" can apply to the target protein and a gene encoding the target protein.

Further, the gene encoding the target protein may be modified if necessary so as to have optimum codons in accordance with the codon usage in a host.

Examples of the target protein include bioactive proteins, receptor proteins, antigen proteins used as vaccines, and enzymes.

Examples of the bioactive proteins include growth factors (proliferative factors), hormones, cytokines, and antibody-related molecules.

Specific examples of the growth factors (proliferative factors) include epidermal growth factor (EGF), insulin-like growth factor-1 (TGF-1), transforming growth factor (TGF), nerve growth factor (NGF), brain-derived neurotrophic factor (BDNF), vesicular endothelial growth factor (VEGF), granulocyte-colony stimulating factor (G-CSF), granulocyte-macrophage-colony stimulating factor (GM-CSF), platelet-derived growth factor (PDGF), erythropoietin (EPO), thrombopoietin (TPO), acidic fibroblast growth factor (aFGF or FGF1), basic fibroblast growth factor (bFGF or FGF2), keratinocyte growth factors (KGF-1 or FGF7, KGF-2 or FGF10), and hepatocyte growth factor (HGF).

Specific examples of the hormones include insulins, glucagon, somatostatin, human growth hormones (hGHs), parathyroid hormone (PTH), and calcitonin.

Specific examples of the cytokines include interleukins, interferons, and tumor necrosis factors (TNFs).

Note that the growth factors (proliferative factors), the hormones, and the cytokines do not necessarily have to be strictly distinguished from each other. For example, the bioactive protein may belong to any one group selected from the growth factors (proliferative factors), the hormones, and the cytokines, or may belong to multiple groups selected therefrom.

Furthermore, the bioactive protein may be a full length protein or a portion thereof. An example of the portion of the protein includes a portion having a physiological activity. A specific example of the portion having a physiological activity includes teriparatide consisting of 34 amino acid residues at the N-terminus of matured parathyroid hormone (PTH).

Incidentally, the target protein may be a portion of a bioactive protein, the portion not having a physiological activity. In this case, after the target protein is obtained, a necessary modification (for example, addition of an amino acid sequence) is performed, and thus a bioactive protein can be obtained. A specific example includes a peptide (Biva18) (SEQ ID NO: 93: Arg Pro Gly Gly Gly Gly Asn Gly Asp Phe Glu Glu Ile Pro Glu Glu Tyr Leu), which is a portion (18 amino acid residues) of a bioactive protein bivalirudin (20 amino acids).

Specific examples of the antibody-related molecules include complete antibodies, Fab, F(ab'), F(ab')2, Fc, a dimer composed of a heavy chain (H chain) and a light chain (L chain), Fc fusion proteins, heavy chains (H chains), and light chains (L chains).

The receptor proteins are not particularly limited, and may be, for example, receptor proteins for bioactive proteins or other bioactive substances. Examples of the other bioactive substances include neurotransmitters such as dopamine. Additionally, the receptor proteins may be orphan receptors whose corresponding ligands are unknown.

The antigen proteins used as vaccines are not particularly limited, as long as an immune response can be elicited, and can be selected as appropriate in accordance with a target of an intended immune response.

Examples of the enzymes include transglutaminases, proteases, endopeptidases, exopeptidases, aminopeptidases, carboxypeptidases, collagenases, chitinases, and the like.

The target protein may be a protein (proprotein), to which a pro-structural portion is added. In a case where the target protein is such a proprotein, a mature protein can be obtained by cleaving the pro-structural portion.

The cleaving of the pro-structural portion can be performed simultaneously with step (4), during step (4), or after step (4) in the production method of the present invention.

The phrase "simultaneously with step (4)" means that step (4) and the cleaving of the pro-structural portion are simultaneously performed using a solution obtained by adding in advance a reagent (for example, a protease to be described below) used for cleaving the pro-structural portion to a "solution having a pH of 12 or below but higher than the pH of a solution obtained in step (2) by 0.1 or more" used in step (4).

The phrase "during step (4)" means that step (4) is initiated without adding the reagent used for cleaving the pro-structural portion to the "solution having a pH of 12 or below but higher than the pH of the solution obtained in step (2) by 0.1 or more" used in step (4), and then the reagent is added during step (4) to cleave the pro-structural portion.

The phrase "after step (4)" means that after step (4) is completed, the pro-structural portion is cleaved using the reagent used for cleaving the pro-structural portion.

The pro-structural portion can be cleaved with, for example, a protease. When a protease is used, from the viewpoint of the activity of the finally obtained protein, the proprotein is generally preferably cleaved at approximately the same position as those of naturally-occurring proteins, and more preferably cleaved at completely the same position as those of naturally-occurring proteins so that the same mature protein as naturally-occurring ones can be obtained. Thus, generally, the most preferable is a specific protease that cleaves the proprotein at this position so that the same protein as naturally-occurring mature proteins can be obtained.

The protease includes ones commercially available such as proTEV protease (manufactured by Promega Corporation), and ones obtained from culture solutions of microorganisms such as a culture solution of an actinobacterium. These proteases can be used in an unpurified state, or may be used after purified to an appropriate purity as necessary.

The fusion protein made of the protein having a self-assembly capability and the target protein can be obtained by expressing a gene construct for expressing the fusion protein in a host.

The "host" is not particularly limited, as long as it is capable of expressing the fusion protein. It is possible to use all types of bacteria, microorganisms other than bacteria, insect cells, animal cells, and the like.

In a case of using a host capable of accumulating the fusion protein in its microbial cells, the cells are disrupted to prepare the solution in step (1). A host capable of secreting the fusion protein outside the cells is preferable because such a disruption treatment is not necessary.

As the bacteria, for example, coryneform bacteria, *Escherichia coli*, and the like can be used.

As the microorganisms other than bacteria, for example, yeasts and the like can be used.

As the insect cells, *Bombyx mori* and the like can be used. As the animal cells, CHO cells and the like can be used.

Among these, coryneform bacteria are preferable.

In the present invention, the "coryneform bacteria" are aerobic gram-positive bacilli, and include *Corynebacterium* bacteria, *Brevibacterium* bacteria, *Microbacterium* bacteria, and so forth. The coryneform bacteria include bacteria which have previously been classified into the genus *Brevibacterium* but are presently united into the genus *Corynebacterium* (Int. J. Syst. Bacteriol., 41, 255 (1991)).

Advantages of using coryneform bacteria include the facts that: the amount of impurity proteins inherently secreted outside the cells is extremely small in comparison with filamentous fungi, yeasts, bacteria of the genus *Bacillus*, and the like, which have been utilized for secretory production of target proteins, so that simplification and omission of the purification step for secretory production of a fusion protein can be expected; coryne form bacteria grow well in a simple medium containing a sugar, ammonia, an inorganic salt, and the like, and are thus excellent in terms of medium cost, culturing method, culture productivity; and others.

The species of the coryneform bacteria specifically include the following:
*Corynebacterium acetoacidophilum*,
*Corynebacterium acetoglutamicum*,
*Corynebacterium alkanolyticum*,
*Corynebacterium callunae*,
*Corynebacterium glutamicum*,
*Corynebacterium lilium*,
*Corynebacterium melassecola*,
*Coryneebacterium thermoaminogenes* (*Corynebacterium efficiens*),
*Corynebacterium herculis*,
*Brevibacterium divaricatum*,
*Brevibacterium flavum*,
*Brevibacterium immariophilum*,
*Brevibacterium lactofermentum* (*Corynebacterium glutamicum*),
*Brevibacterium roseum*,
*Brevibacterium saccharolyticum*,
*Brevibacterium thiogenitalis*,
*Corynebacterium ammoniagenes*,
*Brevibacterium album*,
*Brevibacterium cerinum*, and
*Microbacterium ammoniaphilum*.

The strains of the coryneform bacteria specifically include the following:
*Corynebacterium acetoacidophilum* ATCC 13870,
*Corynebacterium acetoglutamicum* ATCC 15806,
*Corynebacterium alkanolyticum* ATCC 21511,
*Corynebacterium callunae* ATCC 15991,
*Corynebacterium glutamicum* ATCC 13020, ATCC 13032, ATCC 13060, ATCC 13869, FERM BP-734,
*Corynebacterium lilium* ATCC 15990,
*Corynebacterium melassecola* ATCC 17965,
*Corynebacterium thermoaminogenes* FERM BP-1539,
*Corynebacterium herculis* ATCC 13868,
*Brevibacterium divaricatum* ATCC 14020,
*Brevibacterium flavum* ATCC 13826, ATCC 14067, FERM BP-2205,
*Brevibacterium immariophilum* ATCC 14068,
*Brevibacterium lactofermentum* ATCC 13869,
*Brevibacterium roseum* ATCC 13825,
*Brevibacterium saccharolyticum* ATCC 14066,
*Brevibacterium thiogenitalis* ATCC 19240,
*Brevibacterium ammoniagenes* ATCC 6871, ATCC 6872,
*Brevibacterium album* ATCC 15111,
*Brevibacterium cerinum* ATCC 15112, and
*Microbacterium ammoniaphilum* ATCC 15354.

*C. glutamicum* FERM BP-734 isolated as a streptomycin (Sm)-resistant mutant strain from a wildtype strain *C. glutamicum* ATCC13869 is expected to have a mutation in a functional gene involved in protein secretion, and has an extremely high secretory productivity of a heterologous protein, the amount of which accumulated under optimum culture conditions is approximately 2 to 3 times larger than that of the parent strain (wildtype strain). Thus, *C. glutamicum* FERM BP-734 is suitable as the host bacterium.

Using the above-described coryneform bacterium as a parent strain, a strain having an increased protein secretory productivity may be selected by utilizing a mutagenesis or gene recombination method and used as the host. For example, after a treatment with an ultraviolet irradiation or a chemical mutagen such as N-methyl-N'-nitrosoguanidine, a strain having an increased protein secretory productivity can be selected.

Further, a strain modified from the selected strain in such a manner as not to produce the cell surface protein is particularly preferably used as the host because it is easy to purify a heterologous protein secreted into a medium or to a microbial cell surface layer. Such a modification can be carried out by introducing a mutation into a coding region of the cell surface protein or an expression regulatory region thereof on a chromosome by a mutagenesis or gene recombination method. The coryneform bacterium modified not to produce the cell surface protein includes a *C. glutamicum* YDK010 strain that is a cell surface protein CspB (PS2)-disrupted strain of *C. glutamicum* AJ12036 (FERN BP-734) (WO2004/029254).

In a case where the protein having a self-assembly capability is located upstream of the target protein, the "gene construct for expressing the fusion protein" contains: a promoter sequence which functions in the host; a nucleic acid sequence encoding a signal peptide which functions in the host, the nucleic acid sequence connected downstream of the promoter sequence; a nucleic acid sequence encoding the protein having a self-assembly capability, the nucleic acid sequence connected downstream of the nucleic acid sequence encoding the signal peptide; and a nucleic acid sequence encoding the target protein, the nucleic acid sequence connected downstream of the nucleic acid sequence encoding the protein having a self-assembly capability. Meanwhile, in a case where the protein having a self-assembly capability is located downstream of the target protein, the "gene construct for expressing the fusion protein" contains: the promoter sequence which functions in the host; the nucleic acid sequence encoding the signal peptide which functions in the host, the nucleic acid sequence connected downstream of the promoter sequence; the nucleic acid sequence encoding the target protein, the nucleic acid sequence connected downstream of the nucleic acid sequence encoding the signal peptide; and the nucleic acid sequence encoding the protein having a self-assembly capability, the nucleic acid sequence connected downstream of the nucleic acid sequence encoding the target protein. Note that in a case where the fusion protein is accumulated in the microbial cells, the nucleic acid sequence encoding the signal peptide is not necessary.

The nucleic acid sequence encoding the signal peptide should be ligated downstream of the promoter sequence so that the signal peptide is expressed under the control of the promoter.

In the case where the protein having a self-assembly capability is located upstream of the target protein, the nucleic acid sequence encoding the protein having a self-assembly capability should be ligated downstream of the nucleic acid sequence encoding the signal peptide so that the protein having a self-assembly capability connected to the signal peptide can be expressed. Further, the nucleic acid sequence encoding the target protein should be ligated downstream of the nucleic acid sequence encoding the protein having a self-assembly capability so that the target protein connected to the protein having a self-assembly capability can be expressed.

In the case where the protein having a self-assembly capability is located downstream of the target protein, the nucleic acid sequence encoding the target protein should be ligated downstream of the nucleic acid sequence encoding the signal peptide so that the target protein connected to the signal peptide can be expressed. Further, the nucleic acid sequence encoding the protein having a self-assembly capability should be ligated downstream of the nucleic acid sequence encoding the target protein so that the protein having a self-assembly capability connected to the target protein can be expressed.

The gene construct may contain control sequences (an operator, a terminator, and the like) at suitable positions so that they can function to effectively express the fusion protein gene in the host.

The "promoter" is not particularly limited, as long as the promoter functions in the host to be used. The promoter may be derived from the host, or of a heterologous origin.

For example, when a coryneform bacterium is used as the host, the promoter is a promoter which functions in the coryneform bacterium.

The "promoter which functions in the coryneform bacterium" refers to a promoter having a promoter activity in the coryneform bacterium.

Examples of the promoter derived from the coryneform bacterium include promoters of genes of the cell surface proteins PS1, CspB (may also be referred to as PS2), and SlpA (may also be referred to as CspA), and promoters of various amino acid biosynthesis genes.

Specific examples of the promoters of various amino acid biosynthesis genes include promoters of a glutamate dehydrogenase gene in a glutamic acid biosynthesis system, a glutamine synthetase gene in a glutamine synthesis system, an aspartokinase gene in a lysine biosynthesis system, a homoserine dehydrogenase gene in a threonine biosynthesis system, an acetohydroxy acid synthetase gene in isoleucine and valine biosynthesis systems, a 2-isopropyl malic acid synthetase gene in a leucine biosynthesis system, a glutamate kinase gene in proline and arginine biosynthesis systems, a phosphoribosyl-ATP pyrophosphorylase gene in a histidine biosynthesis system, a deoxy-arabino-heptulosonate phosphate (DAHP) synthetase gene in biosynthesis systems of aromatic amino acids such as tryptophan, tyrosine, and phenylalanine, and a phosphoribosyl pyrophosphate (PRPP) amidotransferase gene, an inosinic acid dehydrogenase gene, and a guanylic acid synthetase gene in biosynthesis systems of nucleic acids such as inosinic acid and guanylic acid.

Specific examples of the heterologous promoter in relation to coryneform bacteria include promoters derived from *E. coli*, such as a tac promoter, a lac promoter, a trp promoter, and an araBAD promoter. Among these, a strong promoter such as a tac promoter is preferable, and an inducible promoter such as an araBAD promoter is also preferable.

By using various reporter genes, a native promoter in a highly active form may be obtained and utilized. For example, by making −35 or −10 region in a promoter region close to a consensus sequence, the activity of the promoter can be increased (International Patent Application Publication No. WO00/18935). Examples of methods for evaluating promoter strength and strong promoters are described in the paper by Goldstein et al. (Prokaryotic promoters in biotechnology. Biotechnol. Annu. Rev., 1, 105-128 (1995)) and so on. Further, a substitution, an insertion, or a deletion of several nucleotides in a spacer region between a ribosome binding site (RBS) and a start codon, particularly in a sequence (5'-UTR) immediately upstream of the start codon, is known to greatly influence the mRNA stability and translation efficiency, and these can also be modified.

In the present invention, the host preferably produces the fusion protein as a secretory protein.

Generally, it is known that a secretory protein is translated as a preprotein (may also be referred to as prepeptide) or a preproprotein (may also be referred to as prepropeptide), and then becomes a mature protein by the subsequent processing. Specifically, generally, after a secretory protein is translated as a preprotein or a preproprotein, a pre-portion thereof, that is, a signal peptide, is cleaved by a protease (generally called a signal peptidase) to thus produce and secrete a mature protein or a proprotein, while a pro-portion of the proprotein is further cleaved by a protease to thus produce a mature protein.

Accordingly, in the present invention, a signal peptide is utilized for the secretory production of the fusion protein by the host. Note that, herein, the preprotein and the preproprotein of the secretory protein are collectively referred to as a "secretory protein precursor" in some cases.

The term "signal peptide" (hereinafter may also be sometimes referred to as "signal sequence") refers to an amino acid sequence present at the N-terminus of the secretory protein precursor, but normally absent in naturally-occurring mature proteins.

The signal peptide used in the present invention is not particularly limited, as long as the signal peptide functions in the host. The signal peptide may be derived from the host, or of a heterologous origin.

For example, when a coryneform bacterium is used as the host, the signal peptide is a signal peptide which functions in the coryneform bacterium.

The "signal peptide which functions in the coryneform bacterium" refers to a peptide allowing the coryneform bacterium to secrete the fusion protein when the peptide is ligated to the N-terminus of the fusion protein.

The signal peptide which functions in the coryneform bacterium is preferably a signal peptide of a secretory protein of the host coryneform bacterium, more preferably a signal peptide of a cell surface protein of the coryneform bacterium. The cell surface protein of the coryneform bacterium include PS1 andCspB (PS2) derived from *C. glutamicum* (JP-AHei 6-502548), and SlpA (CspA) derived from *C. ammoniagenes* (JP-A Hei 10-108675). The amino acid sequence of the signal peptide of PS1 is shown in SEQ ID NO: 4, the amino acid sequence of the signal peptide of CspB (PS2) is shown in SEQ ID NO: 5, and the amino acid sequence of the signal peptide of SlpA (CspA) is shown in SEQ ID NO: 6. In addition, according to U.S. Pat. No. 4965197, it is said that a coryneform bacterium-derived DNase also has a signal peptide, and such a signal peptide can also be utilized in the present invention.

Signal peptides have constant, common features in the sequence among biological species. However, a signal peptide which exhibits a secretory function in one species does not necessarily exhibit a secretory function in another species. Thus, in a case where a heterologous signal peptide is used, one which functions in the host to be used should be selected as appropriate. Whether or not a certain signal peptide functions in the host to be used can be confirmed, for example, by expressing the target protein fused to the signal peptide to test whether or not the protein is secreted.

A signal sequence is generally cleaved by a signal peptidase when the translated product is secreted outside the microbial cells. The signal peptidase used may be one that the host to be used inherently has, or a gene encoding the signal peptidase which functions in the host may be incorporated into the host.

The gene encoding the signal peptide can be used in a naturally-occurring form, or may be modified so as to have optimum codons in accordance with the codon usage in the host to be used.

In the case where the protein having a self-assembly capability is located upstream of the target protein, a gene construct for expressing and secreting the fusion protein has the nucleic acid sequence (added sequence) encoding the protein having a self-assembly capability inserted between the nucleic acid sequence encoding the signal peptide and the nucleic acid sequence encoding the target protein. In the case where the protein having a self-assembly capability is located downstream of the target protein, the nucleic acid sequence (added sequence) encoding the protein having a self-assembly capability is inserted downstream of the nucleic acid sequence encoding the target protein.

It should be noted that a nucleic acid sequence encoding an amino acid sequence used for enzymatic or chemical cleavage may be further incorporated between the nucleic acid sequence encoding the added sequence and the nucleic acid sequence encoding the target protein. By inserting the amino acid sequence used for enzymatic or chemical cleavage into the fusion protein, the expressed fusion protein can be enzymatically or chemically cleaved to obtain the target protein.

The cleaving can be performed enzymatically or chemically according to conventional methods.

The cleaving step can be performed simultaneously with step (4), during step (4), or after step (4).

The phrase "simultaneously with step (4)" means that step (4) and the cleaving step are simultaneously performed using a solution obtained by adding in advance a cleaving reagent (for example, a protease used for an enzymatic cleavage to be described later) to the "solution having a pH of 12 or below but higher than the pH of the solution obtained in step (2) by 0.1 or more" used in step (4).

The phrase "during step (4)" means that step (4) is initiated without adding the cleaving reagent to the "solution having a pH of 12 or below but higher than the pH of the solution obtained in step (2) by 0.1 or more" used in step (4), and then the reagent is added during step (4) to perform the cleaving step.

The phrase "after step (4)" means that after step (4) is completed, the cleaving step is performed using the cleaving reagent.

After the cleaving step, the target protein can be easily separated from the protein having a self-assembly capability by adopting methods well-known and commonly-used in this technical field. In this event, only the protein having a self-assembly capability may be precipitated by adjusting a pH of the solution having been subjected to the cleaving step in the same manner as in step (2), and only a solid of the protein having a self-assembly capability may be separated in the same manner as in step (3).

The amino acid sequence used for the enzymatic cleavage is not particularly limited, as long as the sequence is recognized and cleaved by an enzyme capable of causing hydrolysis of a peptide bond. A sequence usable in accordance with the amino acid sequence of the target protein should be selected as appropriate. A nucleic acid sequence encoding the amino acid sequence used for the enzymatic cleavage should be designed as appropriate based on the amino acid sequence. Moreover, optimum codons should be used in accordance with the codon usage in the host, for example.

The amino acid sequence used for the enzymatic cleavage is preferably a recognition sequence of a protease with a high substrate specificity. Specific examples of such an amino acid sequence include a Factor Xa protease recognition sequence, a proTEV protease recognition sequence, and a trypsin recognition sequence. A Factor Xa protease recognizes the amino acid sequence of Ile-Glu-Gly-Arg (=IEGR) (SEQ ID NO: 7) in the protein, whereas a ProTEV protease recognizes the amino acid sequence of Glu-Asn-Leu-Tyr-Phe-Gln (=ENLYFQ) (SEQ ID NO: 8) in the protein. Both of the proteases specifically cleave C-terminal sides of the sequences. Trypsin recognizes Lys and Arg in the protein, and specifically cleaves C-terminal sides of Lys and Arg.

The amino acid sequence used for the chemical cleavage is not particularly limited, as long as the sequence is cleaved under adopted chemical reaction conditions. A sequence usable in accordance with the amino acid sequence of the target protein should be selected as appropriate. A nucleic acid sequence encoding the amino acid sequence used for the chemical cleavage should be designed as appropriate based on the amino acid sequence. Moreover, optimum codons should be used in accordance with the codon usage in the host, for example.

The amino acid sequence used for the chemical cleavage is preferably a sequence in which the cleaving occurs with a high specificity. A specific example of such a cleavage site of the amino acid sequence includes Met. If a cyanogen bromide degradation method is employed, the cleaving occurs on the C-terminal side of Met.

The "gene construct for expressing the fusion protein" can be constructed according to techniques well-known and commonly-used in this technical field.

The technique for introducing the gene construct into the host is not particularly limited. It is possible to use generally-used techniques, for example, a protoplast method (Gene, 39, 281-286 (1985)), an electroporation method (Bio/Technology, 7, 1067-1070) (1989)), and the like.

In a case where the host is a bacterium, the gene construct may be present on a vector capable of self-replicating extrachromosomally like a plasmid, or maybe incorporated into a chromosome.

For example, in a case where the gene construct is introduced into the host coryneform bacterium using a vector, the vector is not particularly limited, as long as it is capable of self-replicating in the coryneform bacterium. The vector may be, for example, vectors derived from bacterial plasmids, vectors derived from yeast plasmids, vectors derived from bacteriophages, cosmids, phagemids, or the like. The vector is preferably plasmids derived from coryneform bacteria. The vector capable of self-replicating in the coryneform bacterium specifically includes pHM1519 (Agric, Biol. Chem., 48, 2901-2903 (1984)); pAM330 (Agric. Biol. Chem., 48, 2901-2903 (1984)); plasmids improved from them to have a drug resistant gene; a plasmid pCRY30 described in JP-A Hei 3-210184; plasmids 15 pCRY21, pCRY2KE, pCRY2KX, pCRY31, pCRY3KE, and pCRY3KX described in JP-A Hei 2-72876 and US Patent No. 5,185,262; plasmids pCRY2 and pCRY3 described in JP-A Hei 1-191686; pAJ655, pAJ611, and pAJ1844 described in JP-A Sho 58-192900; pCG1 described in JP-A Sho 57-134500; pCG2 described in JP-A Sho 58-35197; pCG4 and pCG11 described in JP-A Sho 57-183799; and the like.

In introducing the gene construct, an artificial transposon or the like can also be utilized. In a case of using a transposon, the gene construct is introduced into a chromosome by homologous recombination or by the transposition ability of the transposon itself. Besides, examples of the introduction method utilizing homologous recombination include methods using a linear DNA, a plasmid containing a temperature sensitive replication origin, a plasmid capable of conjugative transfer, a suicide vector not having a replication origin which functions in the host, or the like. Note that when the fusion protein gene is introduced into the chromosome, one or more sequences contained in the gene construct, which are selected from the promoter sequence, the nucleic acid sequence encoding the signal peptide, and the nucleic acid sequence encoding the added sequence, may be ones inherently present on the chromosome of the host, as long as the gene construct is constructed on the chromosome. For example, the gene construct can be constructed on the chromosome as follows. Specifically, a promoter sequence and a nucleic acid sequence encoding the signal peptide, connected downstream of the promoter sequence, which are inherently present on the chromosome of the host, are used as they are; meanwhile, only the gene connected downstream of the nucleic acid sequence encoding the signal peptide is replaced with the nucleic acid sequence encoding the fusion protein made of the added sequence and the target protein.

In a case where two or more types of the target protein are produced, the host should contain gene constructs for expressing the proteins so as to express the proteins. For example, all of the gene constructs for expressing the proteins may be contained on a single expression vector, or all of the gene constructs may be contained on the chromosome. Alternatively, the gene constructs for expressing the proteins may be contained separately on multiple expression vectors, or may be contained separately on a single or multiple expression vectors and on the chromosome. Incidentally, the two or more types of the target protein include a heteromultimeric protein.

By culturing the host having the gene construct(s) introduced therein, and expressing the fusion protein to be secreted outside the microbial cells or accumulated in the microbial cells, a culture solution containing the fusion protein is prepared.

The host can be cultured according to normally-used methods and conditions. For example, when a bacterium is used as the host, the bacterium can be cultured in a normal medium containing a carbon source, a nitrogen source, and inorganic ions. In order to achieve a higher growth, organic trace nutrients such as vitamins and amino acids may also be added as necessary.

As the carbon source, it is possible to use carbohydrates such as glucose and sucrose, organic acids such as acetic acid, alcohols, or others. As the nitrogen source, it is possible to use an ammonia gas, ammonia water, ammonium salts, or others. As the inorganic ions, it is possible to use calcium ions, magnesium ions, phosphate ions, potassium ions, iron ions, or the like as appropriate if necessary.

The culturing can be performed under appropriate conditions for the host to be used. For example, in a case of a coryneform bacterium, the culturing is performed within suitable ranges of pH 5.0 to 8.5 and 15° C. to 37° C. under aerobic conditions for approximately 1 to 7 days. Moreover, it is possible to adopt culture conditions for producing an L-amino acid of coryneform bacteria, or conditions described in the method for producing a protein using a signal peptide of the Sec system or Tat system (see WO01/23591, WO2005/103278).

In a case where an inducible promoter is used to express the fusion protein, the culturing can be performed by adding a promoter inducer to the medium.

Whether the fusion protein is produced or not can be confirmed from the molecular weight of a protein band separated in SDS-PAGE performed on a sample of fractions containing a culture supernatant (including cell homogenate also in a case where the fusion protein is accumulated in the microbial cells). Moreover, it can be confirmed by western blot using an antibody, which is performed on a sample of fractions containing a culture supernatant (including the above-described cell homogenate also) (Molecular cloning (Cold spring Harbor Laboratory Press, Cold spring Harbor (USA), 2001)). Further, it can be confirmed by determining the N-terminal amino acid sequence of the produced protein using a protein sequencer. Furthermore, it can be confirmed also by determining the mass of the produced protein using a mass spectrometer.

Additionally, in some cases, the concentration and purity of the fusion protein (and also the target protein) can also be determined using reversed-phase HPLC.

When the fusion protein is secreted outside the host microbial cells, a "solution containing the fusion protein" may be the above-described culture solution containing the fusion protein itself (culture solution containing the microbial cells), or may be a culture supernatant obtained by separating the host microbial cells from the culture solution (microorganism-removed culture solution). Specifically, the "solution containing the fusion protein" (hereinafter may also be referred to as "solution obtained in step (1) ") includes not only the culture supernatant obtained by removing the microbial cells from the culture solution containing the fusion protein, but also the culture solution itself containing the fusion protein. In the present invention, the culture supernatant is preferably used.

The microbial cells can be separated from the culture solution by methods well-known and commonly-used in this technical field, for example, centrifugation, membrane filtration, and the like. The step of separating the microbial cells is normally performed in step (1) from the viewpoint of improving the purity and the recovery ratio of the fusion protein (or the target protein). Nevertheless, when it is preferable to perform the separation in another step for various reasons, the separation may be performed in any step other than step (1).

When the fusion protein is accumulated in the form of a soluble protein in the host microbial cells, the "solution obtained in step (1)" can be prepared by disrupting the microbial cells, and separating solid matters from the homogenate. The microbial cells can be disrupted according to methods well-known and commonly-used in this technical field, for example, a homogenation method.

When the fusion protein is accumulated in the form of the insoluble protein in the host microbial cells, the "solution obtained in step (1)" can be prepared by disrupting the microbial cells, collecting solid matters from the homogenate, and subjecting the solid matters to well-known and commonly-used methods, for example, a solubilization treatment using a protein denaturing agent such as urea and guanidine or a surfactant such as SDS, to then separate the solid matters. The microbial cells can be disrupted by methods well-known and commonly-used in this technical field, for example, a homogenation method.

In step (2) of the production method of the present invention, a pH of the solution obtained in step (1) is adjusted to such a pH that a recovery ratio calculated according to the following equation is 10% or more, where the recovery ratio (%)=[an amount of the fusion protein in a solution obtained in step (4) /{the amount of the fusion protein in the solution obtained in step (4)+an amount of the fusion protein in a solution after solid separation in step (3)}]×100.

It should be noted that the terms related to "precipitation" used in the description hereinafter (for example, "precipitate", "precipitate-dissolved solution," and the like) are directed to the fusion protein, unless otherwise specifically stated. In a case where "precipitation" is directed to the host microbial cells, such an explanation will be given.

In addition, the description related to the analysis of the fusion protein or the target protein is directed to samples from which the microbial cells have been removed.

"The amount of the fusion protein in the solution obtained in step (4)" and "the amount of the fusion protein in the solution after solid separation in step (3)" in the equation for the recovery ratio can be determined using protein quantification methods well-known and commonly-used in this technical field, for example, reducing SDS-PAGE, reversed-phase HPLC, and the like.

The quantification of the fusion protein by reducing SDS-PAGE can be performed using methods well-known and commonly-used in this technical field, for example, using as an indicator the band intensity of the fusion protein after reducing SDS-PAGE described in Example 1. In this case, the equation for the recovery ratio is as follows:

the recovery ratio (%)=[a band intensity of the fusion protein in the solution obtained in step (4)/{the band intensity of the fusion protein in the solution obtained in step (4)+a band intensity of the fusion protein in the solution after solid separation in step (3)}]×100.

The quantification of the fusion protein by reversed-phase HPLC can be performed using methods well-known and commonly-used in this technical field, for example, a quantification method based on a peak area of the fusion protein in a chromatogram obtained by reversed-phase HPLC described in Example 1-2.

The recovery ratio may vary, depending on the type and usage of the target protein, the necessary amount, and the like. However, the recovery ratio is 10% or more, preferably 20% or more, and further preferably 30% or more.

Note that the upper limit of the pH to achieve the recovery ratio of 10% or more can be easily determined, as described in Example 1 later, by: conducting multiple tests (each test includes steps (1) to (4)) at various pHs with which step (2) is performed; calculating the recovery ratio in each test; and creating a relation graph between the calculated recovery ratio and the pH.

The pH value determined based on the above equations is the upper limit of the pH applicable in step (2) (pH at which the recovery ratio becomes 10% or more). Thus, step (2) can be performed with a pH equal to or below the upper limit of the pH determined above. Meanwhile, the lower limit of the pH is not particularly limited, as long as the fusion protein is not irreversibly denatured by acid. The lower limit of the pH is determined in consideration of the cost for the pH adjustment operation and a desired recovery ratio.

The pH value used in step (2) may vary, depending on the type and usage of the target protein, the necessary amount, and the like. However, the pH is preferably 9 or below. For example, the pH is −0.5 to 9, preferably 1.5 to 9.

A substance used for the pH adjustment is not particularly limited, and all types of acids and alkalis can be used. Examples of the acids include sulfuric acid, hydrochloric acid, acetic acid, phosphoric acid, trifluoroacetic acid (TFA), and the like. Among these, sulfuric acid, hydrochloric acid, and acetic acid are preferable. One acid may be used alone, or two or more acids may be used in combination. Examples of the bases include sodium hydroxide, ammonia, tris(hydroxymethyl)aminomethane (Tris), and the like. One base may be used alone, or two or more bases may be used in combination.

In step (2), after the pH is adjusted, a solid is formed in the solution. The solid is mainly formed of the fusion protein. This fusion protein is not substantially denatured by acid. In order to facilitate the solid formation, the solution is preferably stirred or left alone after the pH adjustment.

Incidentally, in a case where the solution obtained in step (1) already has a pH value that should be achieved by the pH adjustment operation in step (2), the pH adjustment operation in step (2) is not necessary, and step (3) can be performed after the solution obtained in step (1) is stirred or left alone as appropriate.

Thus, as an embodiment, the method for producing a fusion protein of the present invention comprises the following steps (A) to (C):

(A) preparing a solution containing the fusion protein, the solution having such a pH that a recovery ratio calculated according to the following equation is 10% or more, where the recovery ratio (%)=[an amount of the fusion protein in a solution obtained in step (C)/{the amount of the fusion protein in the solution obtained in step (C)+an amount of the fusion protein in a solution after solid separation in step (B)}]×100;

(B) separating a solid from the solution obtained in step (A); and (C) dissolving the solid separated in step (B) into a solution having a pH of 12 or below but higher than the pH of the solution obtained in step (A) by 0.1 or more.

Note that the above descriptions related to steps (1) and (2) can apply to step (A). Moreover, descriptions related to steps (3) and (4) below can apply to steps (B) and (C).

In step (3) of the production method of the present invention, the solid is separated from the solution obtained in step (2). In the solution obtained in step (2), various components (for example, colored substances, lipids, and impurity proteins) derived from the microbial cells and components (for example, colored substances and inorganic salts) derived from the medium remain other than the fusion protein. These can be removed by step (3), consequently making it possible to easily improve the purity of the fusion protein.

The separation can be performed by methods well-known and commonly-used in this technical field. For example, centrifugation, membrane filtration, and the like can be used. Multiple methods maybe performed in combination (for example, a combination of centrifugation and membrane filtration).

The solid obtained in step (3) may have a liquid (impurities) not having been removed completely and attached to the solid. When a solution having a pH equal to or below the upper limit of the pH applicable in step (2) (i.e., the pH at which the recovery ratio of the fusion protein becomes 10%) is added to the solid having the impurities attached thereto, a mixture (suspension) of the solid with the solution (including the liquid (impurities)) is obtained. By separating the solid from the suspension again, a solid having a smaller amount of the impurities attached thereto can be obtained. After step (3), this operation may be performed once or several times.

In step (4) of the production method of the present invention, the solid separated in step (3) is dissolved into the solution having a pH of 12 or below but higher than the pH of the solution obtained in step (2) by 0.1 or more.

A more preferable pH of the solution used in step (4) is higher than the pH at which the recovery ratio of the targeted fusion protein is 10% (i.e., the upper limit of the pH applicable in step (2)) by 0.1 or more, more preferably 0.2 or more, and further preferably 1 or more. The use of the preferable pH in this range makes it possible to sufficiently dissolve the fusion protein into the solution.

The preferable pH may vary, depending on the type of the protein having a self-assembly capability and the type of the target protein. Nevertheless, for example, in a case where the protein having a self-assembly capability is the CspB mature protein or a portion thereof, the pH is preferably 12 or below, more preferably 11 or below, and further preferably 10 or below.

The solution for dissolving the solid separated in step (3) is not particularly limited and any type of substance can be used, as long as the solution has the above-described pH. A specific example thereof includes a buffer. A buffer is preferable because the pH is less likely to change. The buffer includes ones obtained by using Tris, HEPES, sodium phosphate, citric acid, or the like, and Tris is preferable.

By performing step (4), the fusion protein can be obtained in the form of solution. Increasing or decreasing the amount of the solution used in this step can adjust the concentration of the fusion protein as needed. Moreover, the composition of the solution used in step (4) can be determined in consideration of step performed next. Thus, performing steps (2) to (4) makes it possible to easily improve the purity of the fusion protein, and/or concentrate the fusion protein solution, and/or replace the solvent.

Note that when the solid is formed in step (2), substances other than the fusion protein are included as impurities in the solid, and stay remained in the solution obtained in step (4) in some cases. In such a case, by performing steps (2) to (4) again using the solution obtained in step (4) as the solution obtained in step (1), the amount of the impurities can be reduced. The number of times of the operation to be performed after step (4) may be one or more.

In the solution obtained in step (4), the fusion protein is dissolved.

By cleaving the protein having a self-assembly capability from the fusion protein, the target protein can be obtained.

The cleaving can be performed according to methods well-known and commonly-used in this technical field. Examples of the cleaving method include an enzymatic cleavage, a chemical cleavage, and the like. An enzymatic cleavage is preferable because the cleaving specificity is excellent. The cleaving step may be performed on the solution containing the fusion protein obtained in step (4), or may be performed after the fusion protein is separated from the solution obtained in step (4). In the case where the step is performed on the solution containing the fusion protein obtained in step (4), the cleaving maybe performed simultaneously with step (4), during step (4), or after step (4).

The enzymatic cleavage can be suitably performed by incorporating a recognition sequence of a protease with a high substrate specificity (for example, the aforementioned Factor Xa protease recognition sequence, proTEV protease recognition sequence, trypsin recognition sequence) between the protein having a self-assembly capability and the target protein.

The fusion protein obtained in step (4) or the target protein obtained by cleaving the fusion protein can be purified from the solution according to methods well-known and commonly-used in this technical field. The fusion protein or the target protein can be purified by subjecting the solution containing the fusion protein or the target protein to a suitable known method such as, for example, column chromatography (for example, high-performance liquid chromatography (HPLC), reversed-phase chromatography (for example, reversed-phase HPLC), medium high-pressure liquid chromatography, ion-exchange column chromatography, hydrophobic chromatography, gel filtration chromatography, affinity chromatography), alcohol precipitation, or ultrafiltration, or a combination of these.

Note that when the solution obtained after the step of cleaving the fusion protein is subjected to the same step as step (2), the protein having a self-assembly capability is precipitated. By performing this step, the target protein can be purified more efficiently.

Whether or not the target protein is obtained can be confirmed according to analysis methods well-known and commonly-used in this technical field. For example, it can be confirmed by subjecting a sample to SDS-PAGE, and checking the molecular weight of a protein band thus separated. Moreover, it can be confirmed by western blot using an antibody (Molecular cloning (Cold spring Harbor Laboratory Press, Cold spring Harbor (USA), 2001)). Further, it can also be confirmed by determining the N-terminal amino acid sequence of the target protein using a protein sequencer. Furthermore, it can also be confirmed by determining the mass of the target protein using a mass spectrometer. Additionally, in a case where the target protein has enzymatic or certain measureable physiological activity, the confirmation is possible also using the enzymatic activity or physiological activity as an indicator.

The target protein obtained according to the present invention may be used as it is, or may be further modified. The modification includes amino acid addition by chemical synthesis, PEGylation (Biotechnol J., Januuary; 5 (1): 113 (2010)), and the like. For example, in a case where Biva18 (peptide obtained by deleting 2 amino acid residues (D-Phe-L-Pro) from the N-terminus of a bioactive protein bivalirudin (20 amino acids)) is produced as the target protein, full length bivalirudin having a physiological activity can be prepared by adding 2 amino acid residues (D-Phe-L-Pro) to the N-terminus of Biva18 by chemical synthesis. Specifically, full length bivalirudin can be prepared by a chemical synthesis reaction by which particular activated amino acid residues react with the N-terminus of Biva18.

The modified target protein can be purified by methods well-known and commonly-used in this technical field, for example, ion-exchange chromatography, reversed-phase HPLC, hydrophobic chromatography, and the like.

EXAMPLES

Hereinafter, the present invention will be further specifically described based on Examples and Comparative Example. Nevertheless, the present invention is not limited to these Examples.

Example 1

Production of Fusion Protein Having Bioactive Peptide Teriparatide

In Example 1, a bioactive peptide teriparatide (34 amino acid residues) (Teri) was used as a target protein, a sequence consisting of 50 amino acid residues from the N-terminus of a CspB mature protein (CspB50) was used as a protein having a self-assembly capability, a proTEV protease recognition sequence was used as an amino acid sequence used for an enzymatic cleavage, and a coryneform bacterium *C. glutamicum* was used as a host.

(1) Construction of Teriparatide-Secretory Expression Plasmid pPKK50TEV-Teri (i) Total Synthesis of Proinsulin Gene, and Construction of Proinsulin-Secretory Expression Plasmid pPKPIns Using Signal Sequence of Cell Surface Protein CspB of *C. glutamicum* ATCC13869

The amino acid sequence of proinsulin (hereinafter described as PIns) has already been determined (Genbank Accession No. NP_000198.1). In consideration of this sequence and the codon usage of *C. glutamicum*, DNAs shown in <SEQ ID NO: 9> to <SEQ ID NO: 16> were synthesized. Using these DNAs as templates, and using DNAs shown in <SEQ ID NO: 17> and <SEQ ID NO: 18> as primers, a gene encoding PIns was amplified by PCR. Thus, approximately 0.3 kbp of a DNA fragment shown in <SEQ ID NO: 19> was obtained. This DNA fragment was inserted in a SmaI site of a cloning vector pHSG398 (manufactured by Takara Bio Inc.) to thus obtain pHSG-PIns. Using this pHSG-PIns as a template, and using the DNAs shown in <SEQ ID NO: 17> and <SEQ ID NO: 18> as primers, a PIns gene region was amplified by PCR. Thus, approximately 0.3 kbp of a PIns gene fragment was obtained.

On the other hand, the base sequence of a gene encoding the cell surface protein CspB of *C. glutamicum* has already been determined (Mol. Microbial., 9, 97-109 (1993)). Referring to this sequence, pPKPTG1 described in WO01/23591 (the pPKPTG1 is a protransglutaminase (transglutaminase having a pro-structural portion)-secretory expression vector having: a promoter of a cspB gene derived from a *C. glutamicum* ATCC13869 strain; a DNA encoding 30 amino acid residues of a signal peptide of CspB derived from the *C. glutamicum* ATCC13869 strain, the DNA expressibly ligated downstream of the promoter; and a protransglutaminase gene derived from an actinobacterium *Streptoverticillium mobaraense*, the gene ligated downstream of the DNA encoding the signal peptide in such a manner as to be expressed in the form of a fusion protein with the signal peptide) was used as a template, and primers shown in <SEQ ID NO: 20> and <SEQ ID NO: 21> were used in PCR to amplify a region encoding the promoter region of CspB derived from the *C. glutamicum* ATCC13869 strain and the signal peptide. Thus, approximately 0.7 kbp of a DNA fragment was obtained.

Then, using the two amplified DNA fragments (the PIns gene fragment; the fragment of the region encoding the promoter region and the signal peptide) as templates, and using the DNAs shown in <SEQ ID NO: 20> and <SEQ ID NO: 18> as primers, approximately 0.9 kbp of a DNA fragment was obtained by PCR, in which the two DNA fragments were fused together. Note that the primers of <SEQ ID NO: 20> and <SEQ ID NO: 18> were each designed to have a restriction enzyme KpnI recognition sequence. In the PCR reaction, Pyrobest DNA polymerase (manufactured by Takara Bio Inc.) was used, and the reaction conditions were in accordance with the manufacturer's recommended protocol. After restriction enzyme KpnI treatment, the DNA fragment was inserted in a KpnI site of pPK4 described in JP-A Hei 9-322774 to thus obtain pPKPIns.

The result of determining the base sequence of the inserted fragment confirmed that the fusion gene was constructed as expected. Note that the base sequence was determined using BigDye (registered trademark) Terminator v3.1 Cycle Sequencing Kit (manufactured by Applied BioSystems Inc.) and 3130 Genetic Analyzer (manufactured by Applied BioSystems Inc.).

(ii) Construction of Secretory Expression Plasmids for Proinsulin Fused with 1, 2, 3, 4, 5, 6, 7, 8, 9, 10, 11, 12, 13, 14, 15, 17, 20, 50, 100, 150, 200, 250, 300, 350, 400, or 440 Amino acid residues at N-Terminus of Mature Cell Surface Protein CspB of *C. glutamicum* ATCC13869

As described above, the base sequence of the gene encoding the cell surface protein CspB of *C. glutamicum* has already been determined (Mol. Microbial., 9, 97-109 (1993)). It is known that CspB is localized in the cell surface layer of *C. glutamicum*, forming a layer called an S-layer, and a highly hydrophobic amino acid residue region on the C-terminal side is involved in the localization (Mol. Microbial., 9, 97-109 (1993)). Referring to the sequence, primers shown in <SEQ ID NO: 20> and <SEQ ID NO: 22> were synthesized, and using a chromosomal DNA of *C. glutamicum* ATCC13869 as a template prepared in accordance with an ordinary method (the method by Saito and Miura [Biochem. Biophys. Act., 72, 619 (1963)]), a region encoding a 5'-upstream region containing the promoter of the gene encoding CspB (hereinafter may also be referred to as CspB promoter region), the 30 amino acid residues of the signal peptide at the N-terminus of CspB, and 440 amino acid residues at the N-terminus of the CspB mature protein was amplified by PCR. Note that the 440 amino acid residues at the N-terminus of the CspB mature protein were obtained from the full length 469 amino acids of the CspB mature protein of *C. glutamicum* ATCC13869 (SEQ ID NO: 3) by excluding 29 amino acids in the hydrophobic region on the C-terminal side therefrom. In the PCR reaction, Pyrobest DNA polymerase (manufactured by Takara Bio Inc.) was used, and the reaction conditions were in accordance with the manufacturer's recommended protocol.

Next, in order to construct secretory expression plasmids for proinsulin fused with 1, 2, 3, 4, 5, 6, 7, 8, 9, 10, 11, 12, 13, 14, 15, 17, 20, 50, 100, 150, 200, 250, 300, 350, 400, or 440 amino acid residues at the N-terminus of the mature cell surface protein CspB of *C. glutamicum*, regions encoding the CspB promoter region, the 30 amino acid residues of the signal peptide at the N-terminus of CspB, and 1, 2, 3, 4, 5, 6, 7, 8, 9, 10, 11, 12, 13, 14, 15, 17, 20, 50, 100, 150, 200, 250, 300, 350, 400, or 440 amino acid residues at the N-terminus of the CspB mature protein were amplified by PCR using the above-amplified PCR reaction product as a template, and using corresponding synthetic DNAs shown in <SEQ ID NO: 20> and <SEQ ID NO: 23>, <SEQ ID NO: 20> and <SEQ ID NO: 24>, <SEQ ID NO: 20> and <SEQ ID NO: 25>, <SEQ ID NO: 20> and <SEQ ID NO: 26>, <SEQ ID NO: 20> and <SEQ ID NO: 27>, <SEQ ID NO: 20> and <SEQ ID NO: 28>, <SEQ ID NO: 20> and <SEQ ID NO: 29>, <SEQ ID NO: 20> and <SEQ ID NO: 30>, <SEQ ID NO: 20> and <SEQ ID NO: 31>, <SEQ ID NO: 20> and <SEQ ID NO: 32>, <SEQ ID NO: 20> and <SEQ ID NO: 33>, <SEQ ID NO: 20> and <SEQ ID NO: 34>, <SEQ ID NO: 20> and <SEQ ID NO: 35>, <SEQ ID NO: 20> and <SEQ ID NO: 36>, <SEQ ID NO: 20> and <SEQ ID NO: 37>, <SEQ ID NO: 20> and <SEQ ID NO: 38>, <SEQ ID NO: 20> and <SEQ ID NO: 39>, <SEQ ID NO: 20> and <SEQ ID NO: 40>, <SEQ ID NO: 20> and <SEQ ID NO: 41>, <SEQ ID NO: 20> and <SEQ ID NO: 42>, <SEQ ID NO: 20> and <SEQ ID NO: 43>, <SEQ ID NO: 20> and <SEQ ID NO: 44>, <SEQ ID NO: 20> and <SEQ ID NO: 45>, <SEQ ID NO: 20> and <SEQ ID NO: 46>, <SEQ ID NO: 20> and <SEQ ID NO: 47>, or <SEQ ID NO: 20> and <SEQ ID NO: 48> as primers. On the other hand, using the plasmid pPKPIns constructed above in (i) as a template, and using synthetic DNAs shown in <SEQ ID NO: 17> and <SEQ ID NO: 49> as primers, a PIns gene region was amplified by PCR. Thus, a PIns gene fragment was obtained.

Then, using the two amplified DNA fragments (the fragment of the region encoding the CspB promoter region, the CspB signal peptide, and the 1, 2, 3, 4, 5, 6, 7, 8, 9, 10, 11, 12, 13, 14, 15, 17, 20, 50, 100, 150, 200, 250, 300, 350, 400, or 440 amino acid residues at the N-terminus of the mature CspB; the PIns gene fragment) as templates, and using the DNAs shown in <SEQ ID NO: 20> and <SEQ ID NO: 49> as primers, DNA fragments were obtained by PCR, in each of which the two DNA fragments were fused together. Note that the primers of <SEQ ID NO: 20> and <SEQ ID NO: 49> were each designed to have the restriction enzyme KpnI recognition sequence, and the primers of <SEQ ID NO: 23> to <SEQ ID NO: 48> each contained a sequence encoding an amino acid sequence on the N-terminal side of PIns so as to construct a fusion gene made of the PIns gene and the region encoding the N-terminus of the CspB mature protein. In the PCR reaction, Pyrobest DNA polymerase (manufactured by Takara Bio Inc.) was used, and the reaction conditions were in accordance with the manufacturer's recommended protocol. After restriction enzyme KpnI treatment, each of these DNA fragments was inserted in a KpnI site of pPK4 described in JP-A Hei 9-322774 to thus obtain pPKK1PIns, pPKK2PIns, pPKK3PIns, pPKK4PIns, pPKK5PIns, pPKK6PIns, pPKK7PIns, pPKK8PIns, pPKK9PIns, pPKK10PIns, pPKK11PIns, pPKK12PIns, pPKK13PIns, pPKK14PIns, pPKK15PIns, pPKK17PIns, pPKK20PIns, pPKK50PIns, pPKK100PIns, pPKK150PIns, pPKK200PIns, pPKK250PIns, pPKK300PIns, pPKK350PIns, pPKK400PIns, and pPKK440PIns. The result of determining the base sequences of the inserted fragments confirmed that the fusion genes were constructed as expected. Note that the base sequences were determined using BigDye(registered trademark) Terminator v3.1 Cycle Sequencing Kit (manufactured by Applied BioSystems Inc.) and 3130 Genetic Analyzer (manufactured by Applied BioSystems Inc.).

(iii) Construction of Plasmids pPKK17Xa-PIns and pPKK50Xa-PIns

Using pPKK17PIns or pPKK50PIns constructed above in (ii) as a template, and using corresponding synthetic DNAs shown in <SEQ ID NO: 20> and <SEQ ID NO: 50> or <SEQ ID NO: 20> and <SEQ ID NO: 51> as primers, fragments were amplified by PCR, in each of which a region encoding IEGR recognized by a Factor Xa protease was further added to the region encoding the CspB promoter region, the 30 amino acid residues of the signal peptide at the N-terminus of CspB, and the 17 or 50 amino acid residues at the N-terminus of the CspB mature protein. On the other hand, using the plasmidpPKPIns constructed above in (i) as a template, and using corresponding synthetic DNAs shown in <SEQ ID NO: 52> and <SEQ ID NO: 49> or <SEQ ID NO: 53> and <SEQ ID NO: 49> as primers, a PIns gene region was amplified by PCR. Thus, a PIns gene fragment was obtained. Then, using the two amplified DNA fragments (the fragment of the region encoding the CspB promoter region, the CspB signal peptide, the 17 or 50 amino acid residues at the N-terminus of the mature CspB (QETNPT), and IEGR; the PIns gene fragment) as templates, and using the DNAs shown in <SEQ ID NO: 20> and <SEQ ID NO: 49> as primers, DNA fragments were obtained by PCR, in each of which the two DNA fragments were fused together. Note that the primers of <SEQ ID NO: 20> and <SEQ ID NO: 49> were each designed to have the restriction enzyme KpnI recognition sequence, and the primers of <SEQ ID NO: 50> and <SEQ ID NO: 51> were each designed to have a sequence encoding an amino acid sequence on the N-terminal side of PIns so as to construct a fusion gene made of the PIns gene and the base sequence encoding IEGR. In the PCR reaction, Pyrobest DNA polymerase (manufactured by Takara Bio Inc.) was used, and the reaction conditions were in accordance with the manufacturer's recommendedprotocol. After restriction enzyme KpnI treatment, each of these DNA fragments was inserted in a KpnI site of pPK4 described in JP-A Hei 9-322774 to thus obtain pPKK17Xa-PIns and pPKK50Xa-PIns. The result of determining the base sequences of the inserted fragments confirmed that the fusion genes were constructed as expected. Note that the base sequences were determined using BigDye (registered trademark) Terminator v3.1 Cycle Sequencing Kit (manufactured by Applied BioSystems Inc.) and 3130 Genetic Analyzer (manufactured by Applied BioSystems Inc.).

(iv) Construction of Secretory Expression Plasmids for Fusion Proinsulin Having Factor Xa Protease or ProTEV Protease Recognition Sequence Inserted Between N-Terminal Amino Acid Sequence of CspB Mature Protein and Proinsulin Sequence For expressing a certain target protein in a form fused with an amino acid sequence other than that of the target protein, there is well known a method for obtaining the target protein easily by disposing a particular protease recognition sequence of a protease with a high substrate specificity between the amino acid sequence of the target protein and the fused amino acid sequence to thereby cleave the expressed fusion protein with the particular protease. On the other hand, a Factor Xa protease, a ProTEV protease, and the like are known as proteases with a high substrate specificity, and respectively recognize sequences Ile-Glu-Gly-Arg (=IEGR) (SEQ ID NO: 7) and Glu-Asn-Leu-Tyr-Phe-Gln (=ENLYFQ) (SEQ ID NO: 8) in a protein, and specifically cleave C-terminal sides of the sequences. Hence, for example, if fusion PIns is expressed and secreted from CspB-fused PIns by constructing a fusion PIns gene having a base sequence encoding a Factor Xa protease recognition sequence (IEGR) or a ProTEV protease recognition sequence (ENLYFQ) inserted between a base sequence encoding amino acid residues at the N-terminus of the CspB mature protein and a base sequence encoding proinsulin, PIns can be easily obtained from the fusion PIns using these proteases.

Using pPKK6PIns constructed above in (ii) as a template, and using corresponding synthetic DNAs shown in <SEQ ID NO: 20> and <SEQ ID NO: 54> or <SEQ ID NO: 20> and <SEQ ID NO: 55> as primers, fragments were amplified by PCR, in each of which a region encoding IEGR recognized by the Factor Xa protease or ENLYFQ recognized by the ProTEV protease was further added to the region encoding the CspB promoter region, the 30 amino acid residues of the signal peptide at the N-terminus of CspB, and the 6 amino acid residues at the N-terminus of the CspB mature protein (QETNPT). On the other hand, using the plasmid pPKPIns constructed above in (i) as a template, and using the corresponding synthetic DNAs shown in <SEQ ID NO: 52> and <SEQ ID NO: 49> or <SEQ ID NO: 53> and <SEQ ID NO: 49> as primers, a PIns gene region was amplified by PCR. Thus, a PIns gene fragment was obtained. Then, using the two amplified DNA fragments (the fragment of the region encoding the CspB promoter region, the CspB signal peptide, the 6 amino acid residues at the N-terminus of the mature CspB (QETNPT), and IEGR or ENLYFQ; the PIns gene fragment) as templates, and using the DNAs shown in <SEQ ID NO: 20> and <SEQ ID NO: 49> as primers, DNA fragments were obtained by PCR, in each of which the two DNA fragments were fused together. Note that the primers of <SEQ ID NO: 20> and <SEQ ID NO: 49> were each designed to have the restriction enzyme KpnI recognition sequence, the primer of <SEQ ID NO: 54> was designed to have a sequence encoding an amino acid sequence on the N-terminal side of PIns so as to construct a fusion gene made of the PIns gene and the base sequence encoding IEGR, and the primer of <SEQ ID NO: 55> was designed to have a sequence encoding an amino acid sequence on the N-terminal side of PIns so as to construct a fusion gene made of the PIns gene and the base sequence encoding ENLYFQ. In the PCR reaction, Pyrobest DNA polymerase (manufactured by Takara Bio Inc.) was used, and the reaction conditions were in accordance with the manufacturer's recommended protocol. After restriction enzyme KpnI treatment, each of these DNA fragments was inserted in a KpnI site of pPK4 described in JP-A Hei 9-322774 to thus obtain pPKK6Xa-PIns and pPKK6TEV-PIns.

Similarly, using pPKK17PIns or pPKK50PIns constructed above in (ii) as a template, and using the corresponding synthetic DNAs shown in <SEQ ID NO: 20> and <SEQ ID NO: 50> or <SEQ ID NO: 20> and <SEQ ID NO: 51> as primers, fragments were amplified by PCR, in each of which the region encoding IEGR recognized by the Factor Xa protease was further added to the region encoding the CspB promoter region, the 30 amino acid residues of the signal peptide at the N-terminus of CspB, and the 17 or 50 amino acid residues at the N-terminus of the CspB mature protein. On the other hand, using the plasmid pPKPIns constructed above in (i) as a template, and using the corresponding synthetic DNAs shown in <SEQ ID NO: 52> and <SEQ ID NO: 49> or <SEQ ID NO: 53> and <SEQ ID NO: 49> as primers, a PIns gene region was amplified by PCR. Thus, a PIns gene fragment was obtained. Then, using the two amplified DNA fragments (the fragment of the region encoding the CspB promoter region, the CspB signal peptide, the 17 or 50 amino acid residues at the N-terminus of the mature CspB (QETNPT), and IEGR; the PIns gene fragment) as templates, and using the DNAs shown in <SEQ ID NO: 20> and <SEQ ID NO: 49> as primers, DNA fragments were obtained by PCR, in each of which the two DNA fragments were fused together. Note that the primers of <SEQ ID NO: 20> and <SEQ ID NO: 49> were each designed to have the restriction enzyme KpnI recognition sequence, and the primers of <SEQ ID NO: 50> and <SEQ ID NO: 51> were each designed to have the sequence encoding the amino acid sequence on the N-terminal side of PIns so as to construct the fusion gene made of the PIns gene and the base sequence encoding IEGR. In the PCR reaction, Pyrobest DNA polymerase (manufactured by Takara Bio Inc.) was used, and the reaction conditions were in accordance with the manufacturer's recommended protocol. After restriction enzyme KpnI treatment, each of these DNA fragments was inserted in a KpnI site of pPK4 described in JP-A Hei 9-322774 to thus obtain pPKK17Xa-PIns and pPKK50Xa-PIns. The result of determining the base sequences of the inserted fragments confirmed that the fusion genes were constructed as expected. Note that the base sequences were determined using BigDye (registered trademark) Terminator v3.1 Cycle Sequencing Kit (manufactured by Applied BioSystems Inc.) and 3130 Genetic Analyzer (manufactured by Applied BioSystems Inc.).

(v) Total Synthesis of Human Growth Hormone hGH Gene, and Construction of Human Growth Hormone hGH-Secretory Expression Plasmids in C. glutamicum The amino acid sequence of human growth hormone (hGH) has already been determined (Genbank Accession No. CAA23779.1). In consideration of this sequence, particularly an amino acid sequence of mature hGH excluding 26 residues of a signal sequence at the N-terminus, and the codon usage in C. glutamicum, DNAs shown in <SEQ ID NO: 56> to <SEQ ID NO: 69> were synthesized. Using these DNAs as templates, and using independently synthesized DNAs shown in <SEQ ID NO: 70> and <SEQ ID NO: 71> as primers, a hGH gene was amplified by PCR. Thus, approximately 0.6 kbp of a DNA fragment shown in <SEQ ID NO: 72> was obtained. The DNA fragment was inserted in a SmaI site of a cloning vector pHSG398 (manufactured by Takara Bio Inc.) to thus obtain pHSG-hGH. Using this pHSG-hGH as a template, and using the DNAs shown in <SEQ ID NO: 70> and <SEQ ID NO: 71> as primers, a hGH gene region was amplified by PCR. Thus, approximately 0.6 kbp of a hGH gene fragment was obtained. Next, pPK-SPTG1 described in WO01/23591 (the pPKSPTG1 is a protransglutaminase (transglutaminase having a pro-structural portion)-secretory expression vector having: the promoter of the cspB gene derived from the C. glutamicum ATCC13869 strain; a DNA encoding 25 amino acid residues of a signal peptide of CspA (SlpA) <Genbank Accession No. BAB62413.1> derived from a C. ammoniagenes ATCC6872 strain, the DNA expressibly ligated downstream of the promoter; and the protransglutaminase gene derived from S. mobaraense, the gene ligated downstream of the DNA encoding the signal peptide in such a manner as to be expressed in the form of a fusion protein with the signal peptide) and pPKPTG1 described in WO01/23591 (containing the promoter region of CspB derived from the C. glutamicum ATCC13869 strain and the DNA encoding the signal peptide) were used as templates, and primers shown in <SEQ ID NO: 20> and <SEQ ID NO: 73> or <SEQ ID NO: 20> and <SEQ ID NO: 74> were used in PCR to amplify regions encoding the promoter region of the C. glutamicum ATCC13869-derived CspB and the signal peptide of the C. ammoniagenes ATCC6872 strain-derived CspA or the C. glutamicum ATCC13869 strain-derived CspB. Thus, DNA fragments, each approximately 0.7 kbp, were obtained. Then, using the two amplified DNA fragments (the hGH gene fragment; the fragment of the region encoding the CspB promoter region and any one of the signal peptides) as templates, and using the DNAs shown in <SEQ ID NO: 20> and <SEQ ID NO: 71> as primers, DNA fragments, each approximately 1.2 kbp, were obtained by PCR, in each of which the two DNA fragments were fused together. Note that the primers of <SEQ ID NO: 20> and <SEQ ID NO: 71> were each designed to have the restriction enzyme KpnI recognition sequence, and the primers of <SEQ ID NO: 73> and <SEQ ID NO: 74> were each designed to have a sequence encoding amino acid residues at the N-terminus of hGH so as to construct a fusion gene made of the hGH gene and the region encoding the corresponding signal peptide. In the PCR reaction, Pyrobest DNA polymerase (manufactured by Takara Bio Inc.) was used, and the reaction conditions were in accordance with the manufacturer's recommendedprotocol. After restriction enzyme KpnI treatment, each of these DNA fragments was inserted in a KpnI site of pPK4 described in JP-AHei 9-322774 to thus obtain pPS-hGH andpPK-hGH. The result of determining the base sequences of the inserted fragments confirmed that the fusion genes were constructed as expected. Note that all the base sequences were determined using BigDye (registered trademark) Terminator v3.1 Cycle Sequencing Kit (manufactured by Applied BioSystems Inc.) and 3130 GeneticAnalyzer (manufacturedbyAppliedBioSystems Inc.).

(vi) Construction of Secretory Expression Plasmids for Human Growth Hormone hGH Fused with Signal Peptide of Cell Surface Protein CspB of C. glutamicum ATCC13869, Amino Acid Residues at N-Terminus of the Mature Protein, and Factor Xa Protease Recognition Sequence Using pPKK6Xa-PIns, pPKK17Xa-PIns, or pPKK50Xa-PIns constructed above in (iv) as a template, and using corresponding synthetic DNAs shown in <SEQ ID NO: 20> and <SEQ ID NO: 75>, <SEQ ID NO: 20> and <SEQ ID NO: 76>, or <SEQ ID NO: 20> and <SEQ ID NO: 77>0 as primers, regions encoding the CspB promoter region, the 30 amino acid residues of the signal peptide at the N-terminus of CspB, the amino acid residues (6, 17, or 50 residues) at the N-terminus of the CspB mature protein, and the Factor Xa protease recognition sequence (IEGR) were amplified by PCR. On the other hand, using the plasmid pPS-hGH constructed above in (v) as a template, and using the synthetic DNA shown in <SEQ ID NO: 70> and <SEQ ID NO: 71> as primers, a hGH gene region was amplified by PCR. Then, using the two amplified DNA fragments (each fragment of the region encoding the CspB promoter region, the CspB signal peptide, the amino acid residues at the N-terminus of the mature CspB, and IEGR; the hGH gene fragment) as templates, and using the DNAs shown in <SEQ ID NO: 20> and <SEQ ID NO: 71> as primers, DNA fragments were obtained by PCR, in each of which the two DNA fragments were fused together. Note that the primers of <SEQ ID NO: 20> and <SEQ ID NO: 71> were each designed to have the restriction enzyme KpnI recognition sequence, and the primers of <SEQ ID NO: 75>, <SEQ ID NO: 76>, and <SEQ ID NO: 77> were each designed to have a sequence encoding amino acid residues at the N-terminus of hGH so as to construct a fusion gene made of the hGH gene and the region encoding the Factor Xa protease recognition sequence (IEGR). In the PCR reaction, Pyrobest DNA polymerase (manufactured by Takara Bio Inc.) was used, and the reaction conditions were in accordance with the manufacturer's recommended protocol. After restriction enzyme KpnI treatment, each of these DNA fragments was inserted in a KpnI site of pPK4 described in JP-A Hei 9-322774 to thus obtain pPKK6Xa-hGH, pPKK17Xa-hGH, and pPKK50Xa-hGH.

(vii) Construction of Teriparatide-Secretory Expression Plasmid pPKK6Xa-Teri

The amino acid sequence of a matured human parathyroid hormone PTH has already been determined (Genbank Accession No. AAA60215.1). A peptide from 1 to 34 residues at the N-terminus of this human parathyroid hormone PTH is known as a peptide teriparatide having a physiological activity serving as an osteoporosis drug. In consideration of the amino acid sequence of this teriparatide and the codon usage in C. glutamicum, DNAs shown in <SEQ ID NO: 78> and <SEQ ID NO: 79> were synthesized. Using the DNAs as templates, and using independently synthesized DNAs shown in <SEQ ID NO: 80> and <SEQ ID NO: 81> as primers, a teriparatide gene shown in <SEQ ID NO: 82> was amplified by PCR. The DNA fragment was inserted in a SmaI site of a cloning vector pHSG398 (manufactured by Takara Bio Inc.) to thus obtain pHSG-Teri. Using this pHSG-Teri as a template, and using the DNAs shown in <SEQ ID NO: 80> and <SEQ ID NO: 81> as primers, a teriparatide gene region was amplified by PCR. Next, pPKSPTG1 described in WO01/23591 (containing the promoter region of CspB derived from the *C. glutamicum* ATCC13869 strain and the DNA encoding the signal peptide of CspA (SlpA) derived from the *C. ammoniagenes* ATCC6872 strain) and pPKPTG1 described in WO01/23591 (containing the promoter region of CspB derived from the *C. glutamicum* ATCC13869 strain and the DNA encoding the signal peptide) were used as templates, and primers shown in <SEQ ID NO: 20> and <SEQ ID NO: 83> or <SEQ ID NO: 20> and <SEQ ID NO: 84> were used in PCR to amplify regions encoding the promoter region of the *C. glutamicum* ATCC13869-derived CspB and the signal peptide of the *C. ammoniagenes* ATCC6872 strain-derived CspA or the *C. glutamicum* ATCC13869 strain-derived CspB. Then, using the two amplified DNA fragments (the teriparatide gene fragment; the fragment of the region encoding the CspB promoter region and any one of the signal peptides) as templates, and using the DNAs shown in <SEQ ID NO: 20> and <SEQ ID NO: 81> as primers, DNA fragments, each approximately 0.8 kbp, were obtained by PCR, in each of which the two DNA fragments were fused together. Note that the primers of <SEQ ID NO: 20> and <SEQ ID NO: 81> were each designed to have the restriction enzyme KpnI recognition sequence, and the primers of <SEQ ID NO: 83> and <SEQ ID NO: 84> were each designed to have a sequence encoding amino acid residues at the N-terminus of teriparatide so as to construct a fusion gene made of the teriparatide gene and the region encoding the corresponding signal peptide. In the PCR reaction, Pyrobest DNA polymerase (manufactured by Takara Bio Inc.) was used, and the reaction conditions were in accordance with the manufacturer's recommended protocol. After restriction enzyme KpnI treatment, each of these DNA fragments was inserted in a KpnI site of pPK4 described in JP-A Hei 9-322774 to thus obtain pPS-Teri and pPK-Teri.

Next, using pHSG-Teri described above as a template, and using DNAs shown in <SEQ ID NO: 85> and <SEQ ID NO: 81> as primers, a teriparatide gene region was amplified by PCR. Moreover, using pPKK6Xa-hGH constructed above in (vi) as a template, and using primers shown in <SEQ ID NO: 20> and <SEQ ID NO: 86>, a region encoding the CspB promoter region, the 30 amino acid residues of the signal peptide at the N-terminus of CspB, the 6 amino acid residues at the N-terminus of the CspB mature protein, and the Factor Xa protease recognition sequence (IEGR) was amplified by PCR. Then, using the two amplified DNA fragments (the teriparatide gene fragment; the fragment of the region encoding the CspB promoter region, the CspB signal peptide, the 6 amino acid residues at the N-terminus of the CspB mature protein, and IEGR) as templates, and using the DNAs shown in <SEQ ID NO: 20> and <SEQ ID NO: 81> as primers, approximately 0.8 kbp of a DNA fragment was obtained by PCR, in which the two DNA fragments were fused together. Note that the primers of <SEQ ID NO: 20> and <SEQ ID NO: 81> were each designed to have the restriction enzyme KpnI recognition sequence, and the primer of <SEQ ID NO: 85> was designed to have a sequence encoding the Factor Xa protease recognition sequence (IEGR) so as to construct a fusion gene made of the teriparatide gene and the region encoding the Factor Xa protease recognition sequence (IEGR). In the PCR reaction, Pyrobest DNA polymerase (manufactured by Takara Bio Inc.) was used, and the reaction conditions were in accordance with the manufacturer's recommended protocol. After restriction enzyme KpnI treatment, the DNA fragment was inserted in a KpnI site of pPK4 described in JP-A Hei 9-322774 to thus obtain pPKK6Xa-Teri. The result of determining the base sequence of the inserted fragment confirmed that the fusion gene was constructed as expected. Note that all the base sequences were determined using BigDyeR Terminator v3.1 Cycle Sequencing Kit (manufactured by Applied BioSystems Inc.) and 3130 Genetic Analyzer (manufactured by Applied BioSystems Inc.).

(viii) Construction of Teriparatide-Secretory Expression Plasmid pPKK50TEV-Teri

Using the plasmid pPKK50Xa-PIns constructed above in (iii) as a template, and using synthetic DNAs shown in <SEQ ID NO: 20> and <SEQ ID NO: 87> as primers, a region encoding the 5'-upstream region containing the promoter region of CspB, the 30 amino acid residues of the signal peptide at the N-terminus, the 50 residues on the N-terminal side of the mature cell surface protein, and the amino acid sequence ENLYFQ recognized by the ProTEV protease was amplified by PCR. On the other hand, using the plasmid pPKK6Xa-Teri constructed above in (vii) as a template, and using synthetic DNAs shown in <SEQ ID NO: 88> and <SEQ ID NO: 89> as primers, a teriparatide gene region was amplified by PCR. Then, using the amplified DNA fragments (the fragment of the region encoding the CspB promoter, the CspB signal peptide, the 50 residues in the N-terminal amino acid sequence of CspB, and the amino acid sequence ENLYFQ; the teriparatide gene fragment) as templates, and using the DNAs shown in <SEQ ID NO: 20> and <SEQ ID NO: 89> as primers, a DNA fragment was obtained by PCR, in which the DNA fragments were fused together. Note that the primers of <SEQ ID NO: 20> and <SEQ ID NO: 89> were each designed to have the restriction enzyme KpnI recognition sequence, and the primer of <SEQ ID NO: 88> was designed to have a sequence encoding an amino acid sequence on the N-terminal side of teriparatide so as to construct a fusion gene made of teriparatide and the base sequence encoding ENLYFQ. In the PCR reaction, Pyrobest DNA polymerase (manufactured by Takara Bio Inc.) was used, and the reaction conditions were in accordance with the manufacturer's recommended protocol. After restriction enzyme KpnI treatment, the DNA fragment was inserted in a KpnI site of pPK4 described in JP-A Hei 9-322774 to thus obtain a plasmid pPKK50TEV-Teri. The result of determining the base sequence of the inserted fragment confirmed that the fusion gene was constructed as expected. Note that the base sequence was determined using BigDye(registered trademark) Terminator v3.1 Cycle Sequencing Kit (manufactured by Applied BioSystems Inc.) and 3130 Genetic Analyzer (manufactured by Applied BioSystems Inc.).

(2) Secretory Expression of Fusion Protein CspB50TEV-Teriparatide (Abbreviated as 50-Teri) Using pPKK50TEV-Teri Using pPKK50TEV-Teri constructed in (1), a *C. glutamicum* YDK010 strain described in WO001/23591 was transformed. The obtained transformed strain was cultured at 30° C. for 72 hours in MM liquid media (120 g of glucose, 0.4 g of magnesium sulfate heptahydrate, 30 g of ammonium sulfate, 1 g of potassium dihydrogen phosphate, 0.01 g of iron sulfate heptahydrate, 0.01 g of manganese sulfate pentahydrate, 200 μg of thiamine hydrochloride, 500 μg of biotin, 0.15 g of DL-methionine, 50 g of calcium carbonate, adjusted to 1 L with water and to pH 7.5) containing 25 mg/l of kanamycin. After the culturing was completed, each culture solution was centrifuged. The resulting culture supernatant was subjecting to reducing SDS-PAGE. Staining with CBB R-250 (manufactured by Bio-Rad Laboratories, Inc.) showed a band of the target fusion protein 50-Teri.

On the other hand, the obtained transformed strain was cultured, while being agitated for aeration, at 30° C. for 3 days in a jar fermenter of 1 L capacity, in which 300 mL of a MMTG liquid medium (120 g of glucose, 2 g of calcium chloride, 3 g of magnesium sulfate heptahydrate, 3 g of ammonium sulfate, 1.5 g of potassium dihydrogen phosphate, 0.03 g of iron sulfate heptahydrate, 0.03 g of manganese sulfate pentahydrate, 450 µg of thiamine hydrochloride, 450 µg of biotin, 0.15 g of DL-methionine, 50 g of calcium carbonate, adjusted to 1 L with water and to pH 6.7) containing 25 mg/l of kanamycin had been charged and the pH was being maintained at 6.7 by adding an ammonia gas.

(3) Removal of Microbial Cells from Culture Solution, and Storage of Microbial Cell-Removed Culture Solution After the culturing was completed, the culture solution was transferred to microtubes and centrifuged using a centrifuge at 12000 G for 10 minutes to separate the microbial cells. The resulting centrifuged supernatant was filtered through a sterile filter having a pore diameter of 0.22 µm, and the resulting filtrate was cryopreserved at -80° C. as a "microbial cell-removed culture solution" (corresponding to "solution obtained in step (1)").

(4) Precipitation and Solubilization of Fusion Protein (50-Teri) due to pH Change The cryopreserved microbial cell-removed culture solution was thawed at 25° C. and centrifuged using a centrifuge at 12000 G for 1 minute to separate a precipitate mainly including an inorganic salt formed during the cryopreservation. To four microtubes, 0, 5, 10, and 30 µL of aqueous solutions of 0.5 M sulfuric acid and 30, 25, 20, and 0 µL of Milli Q water were respectively added and uniformly mixed. Then, 100 µL of the resulting centrifuged supernatant was dispensed into each of the tubes. All of the mixtures were adjusted to a volume of 130 µL.

After stirring, these were left alone for 10 minutes. Thereby, "pH-adjusted culture solutions" at pH 7.4, pH 6.6, pH 3.8, and pH 1.7 were obtained (corresponding to "solution obtained in step (2) "). The "pH-adjusted culture solutions" at pH 6.6, pH 3.8, and pH 1.7 were clouded, and precipitation formation was observed. Those "pH-adjusted culture solutions" were centrifuged using a centrifuge at 12000 G for 5 minutes to separate precipitates formed by the pH change (corresponding to "solid separated in step (3) "). The resulting centrifuged supernatants were transferred as "supernatants of the pH-adjusted culture solutions" (corresponding to "solution after solid separation in step (3)") to different microtubes separately. To the remaining precipitates, a buffer (100 mM Tris-HCl, pH 8.5) was added in the same volume as those of the centrifuged supernatants having been removed. By stirring, the precipitates were immediately dissolved, and "precipitate-dissolved solutions" were obtained (corresponding to "solution obtained in step (4)"). All of the precipitate-dissolved solutions had a pH of around neutral, which were pH 8.3, pH 8.3, pH 8.1, and pH 7.8. In consideration of the above pH range of the precipitate formation and the fact that the precipitates formed were reversibly and immediately re-dissolved at around the neutral pH, it was found out that the precipitation phenomenon observed in step (2) is totally different from a phenomenon in which a protein is denatured by acid generally in an irreversible manner.

The "supernatants of the pH-adjusted culture solutions" at pH 7.4, pH 6.6, pH 3.8, and pH 1.7, and the "precipitate-dissolved solutions" obtained by the above-described operations were subjected to reducing SDS-PAGE, and bands of 50-Teri were checked to analyze and evaluate the precipitation and solubilization of 50-Teri due to the pH change. Note that the reducing SDS-PAGE was performed using Any kD™ Mini-PROTEAN(registered trademark) TGX™ Precast Gel (Bio-Rad Laboratories, Inc.), and the bands of the fusion protein 50-Teri were detected by staining with SYPRO (registered trademark) Ruby (Life Technologies Japan Ltd.). Subsequently, the band intensity at each pH was quantified using software Multi Gauge (manufactured by FUJI FILM Corporation), and the recovery ratio of 50-Teri at each pH was calculated according to the following equation:

the recovery ratio (%)=[a band intensity of the fusion protein in the solution obtained in step (4)/{the band intensity of the fusion protein in the solution obtained in step (4)+a band intensity of the fusion protein in the solution after solid separation in step (3)}]×100.

It should be noted that, in Examples and Comparative Example to be described below also, the recovery ratio in reducing SDS-PAGE was calculated in the same manner as in Example 1.

The calculated recovery ratios of 50-Teri from the "pH-adjusted culture solutions" at pH 7.4, pH 6.6, pH 3.8, and pH 1.7 were respectively 1%, 95%, 99%, and 99%. FIG. 1-A shows the relation between the calculated recovery ratio and the pH of the "pH-adjusted culture solutions." The graph revealed that the precipitation phenomenon observed in step (2) is totally different from an isoelectric point precipitation phenomenon in which the solubility of a protein becomes lowest at an isoelectric point thereof.

FIG. 1-B shows the pH of the "pH-adjusted culture solutions," band portions of the fusion protein 50-Teri in images of electrophoresis of the "supernatants of the pH-adjusted culture solutions" and the corresponding "precipitate-dissolved solutions," and the recovery ratio.

The 50-Teri was present in the "supernatant of the pH-adjusted culture solution" at pH 7.4. The 50-Teri was not detected in the "supernatants of the pH-adjusted culture solutions" at pH 6.6, pH 3.8, and pH 1.7, but was detected in the corresponding "precipitate-dissolved solutions" at these pHs.

Example 1-2

Production of Fusion Protein 50-Teri Having bioactive Peptide Teriparatide, and Production of Target Protein Teriparatide In Example 1-2, in the same manner as in Example 1, a bioactive peptide teriparatide (34 amino acid residues) (Teri) was used as a target protein, a sequence consisting of 50 amino acid residues from the N-terminus of a CspB mature protein (CspB50) was used as a protein having a self-assembly capability, a proTEV protease recognition sequence was used as an amino acid sequence used for an enzymatic cleavage, and a coryneform bacterium C. glutamicum was used as a host.

(1) Construction of Teriparatide-Secretory Expression Plasmid pPKK50TEV-Teri constructed according to the procedure described in Example 1 (1).

(2) Secretory Expression of Fusion Protein Using pPKK50TEV-Teri

According to the procedure described in Example 1 (2), a *C. glutamicum* YDK010 strain transformed using pPKK50TEV-Teri was cultured.

(3) Removal of Microbial Cells from Culture Solution, and Storage of Microbial Cell-Removed Culture Solution carried out according to the procedure described in Example 1 (3).

(4) Precipitation and Solubilization of Fusion Protein 50-Teri due to pH Change

The cryopreserved microbial cell-removed culture solution was thawed at 25° C. and centrifuged using a centrifuge at 12000 G for 1 minute to separate a precipitate mainly including an inorganic salt formed during the cryopreservation. To eight microtubes, 0 μL, 5 μL, 10 μL, 15 μL, 20 μL, 30 μL, 40 μL, and 50 μL of aqueous solutions of 0.5 M sulfuric acid and 50 μL, 45 μL, 40 μL, 25 μL, 30 μL, 20 μL, 10 μL, and 0 μL of Milli Q water were respectively added and uniformly mixed. Then, 600 μL of the resulting centrifuged supernatant was dispensed into each of the tubes. All of the mixtures were adjusted to a volume of 650 μL.

After stirring, these were left alone for 10 minutes. Thereby, "pH-adjusted culture solutions" at pH 7.9, pH 7.6, pH 7.3, pH 7.1, pH 6.6, pH 4.9, pH 4.1, and pH 3.7 were obtained (corresponding to "solution obtained in step (2)"). The "pH-adjusted culture solutions" at pH 7.1, pH 6.6, pH 4.9, pH 4.1, and pH 3.7 were clouded, and precipitation formation was observed. Those "pH-adjusted culture solutions" were centrifuged using a centrifuge at 12000 G for 5 minutes to separate precipitates formed by the pH change (corresponding to "solid separated in step (3)"). The resulting centrifuged supernatants were transferred as "supernatants of the pH-adjusted culture solutions" (corresponding to "solution after solid separation in step (3)") to different microtubes separately. To the remaining precipitates, a buffer (100 mM Tris-HCl, pH 8.5) was added in the same volume as those of the centrifuged supernatants having been removed. By stirring, the precipitates were immediately dissolved, and "precipitate-dissolved solutions" were obtained (corresponding to "solution obtained in step (4)"). All of the "precipitate-dissolved solutions" had a pH of around neutral, which were pH 8.0, pH 8.0, pH 8.0, pH 8.0, pH 8.0, pH 7.9, pH 7.7, and pH 7.6.

The "supernatants of the pH-adjusted culture solutions" at pH 7.9, pH 7.6, pH 7.3, pH 7.1, pH 6.6, pH 4.9, pH 4.1, and pH 3.7, and the "precipitate-dissolved solutions" obtained by the above-described operations were subjected to reducing SDS-PAGE and reversed-phase HPLC to analyze and evaluate the precipitation and solubilization of 50-Teri due to the pH change. Note that the recovery ratio of 50-Teri was calculated according to the following equation using reversed-phase HPLC:

the recovery ratio (%)=[an amount of the fusion protein in the solution obtained in step (4)/{the amount of the fusion protein in the solution obtained in step (4)+an amount of the fusion protein in the solution after solid separation in step (3)}]×100.

The amounts of the fusion proteins were quantified from the peak area in the reversed-phase HPLC. Specifically, a calibration curve was created using a known substance (IGF-1), and the peak area of each measurement sample was assigned to the calibration curve, so that the amount of the fusion protein was calculated. The conditions of the reversed-phase HPLC are shown below.

System: a set of Waters Alliance PDA system
Column: YMC-Triart C18 φ4.6×100 mm, a particle diameter of 5 μm, a pore diameter of 12 nm
Column temp.: 30° C.
Mobile phase A: aqueous solution of 10 mM ammonium acetate, aqueous solution of 10% acetonitrile, pH 7.0
Mobile phase B: aqueous solution of 10 mM ammonium acetate, aqueous solution of 80% acetonitrile, pH 7.0
Flow rate: 1.0 mL/min
Detection: 220 nm
Injection volume: 30 μL

| Gradient: Time (min) | A (%) | B (%) |
|---|---|---|
| 0 | 100 | 0 |
| 25 | 50 | 50 |
| 28 | 0 | 100 |

The recovery ratios of 50-Teri from the "pH-adjusted culture solutions" at pH 7.9, pH 7.6, pH 7.3, pH 7.1, pH 6.6, pH 4.9, pH 4.1, and pH 3.7 were respectively 0%, 0%, 0%, 63%, 5 95%, 96%, 98%, and 100%. FIG. 1-2A shows a relation graph between the calculated recovery ratio and the pH of the "pH-adjusted culture solutions."

Figures 1, 2, 2B:
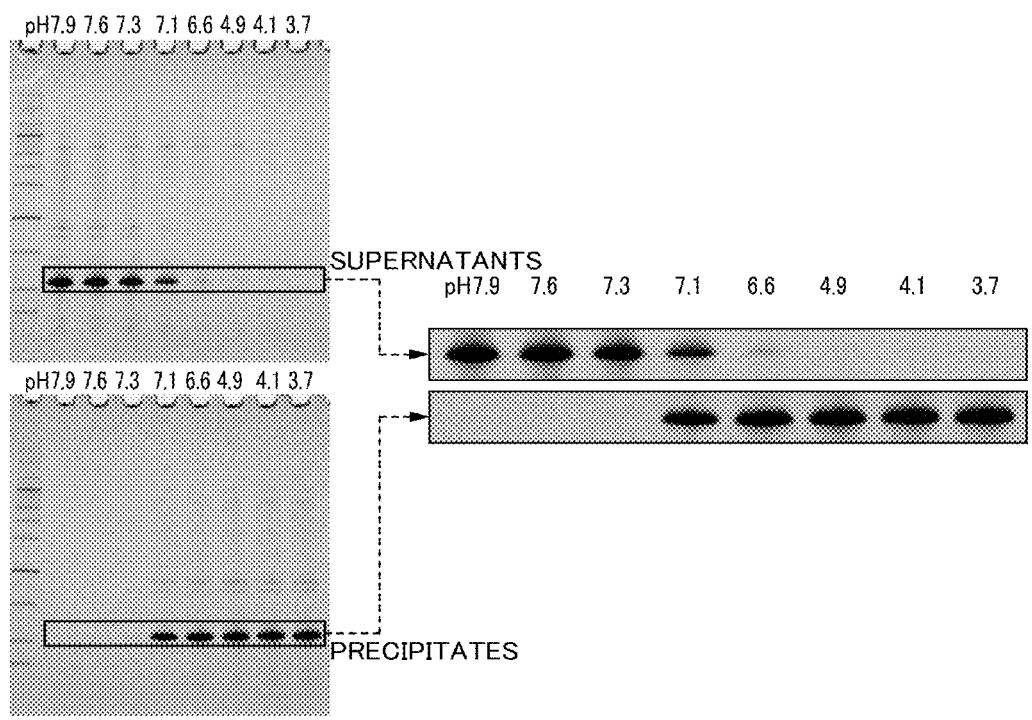

FIG. 1-2B shows images of electrophoresis of the "pH-adjusted culture solutions" and the corresponding "precipitate-dissolved solutions," and photographs of extracted band portions of the fusion protein 50-Teri.

The 50-Teri was present in the "supernatants of the pH-adjusted culture solutions" at pH 7.9, pH 7.6, pH 7.3, and pH 7.1. Although the 50-Teri was not detected in the "supernatants of the pH-adjusted culture solutions" at pH 6.6, pH 4.9, pH 4.1, and pH 3.7, significant amounts thereof were detected in the corresponding "precipitate-dissolved solutions" at these pHs.

Figures 1, 2, 2C:
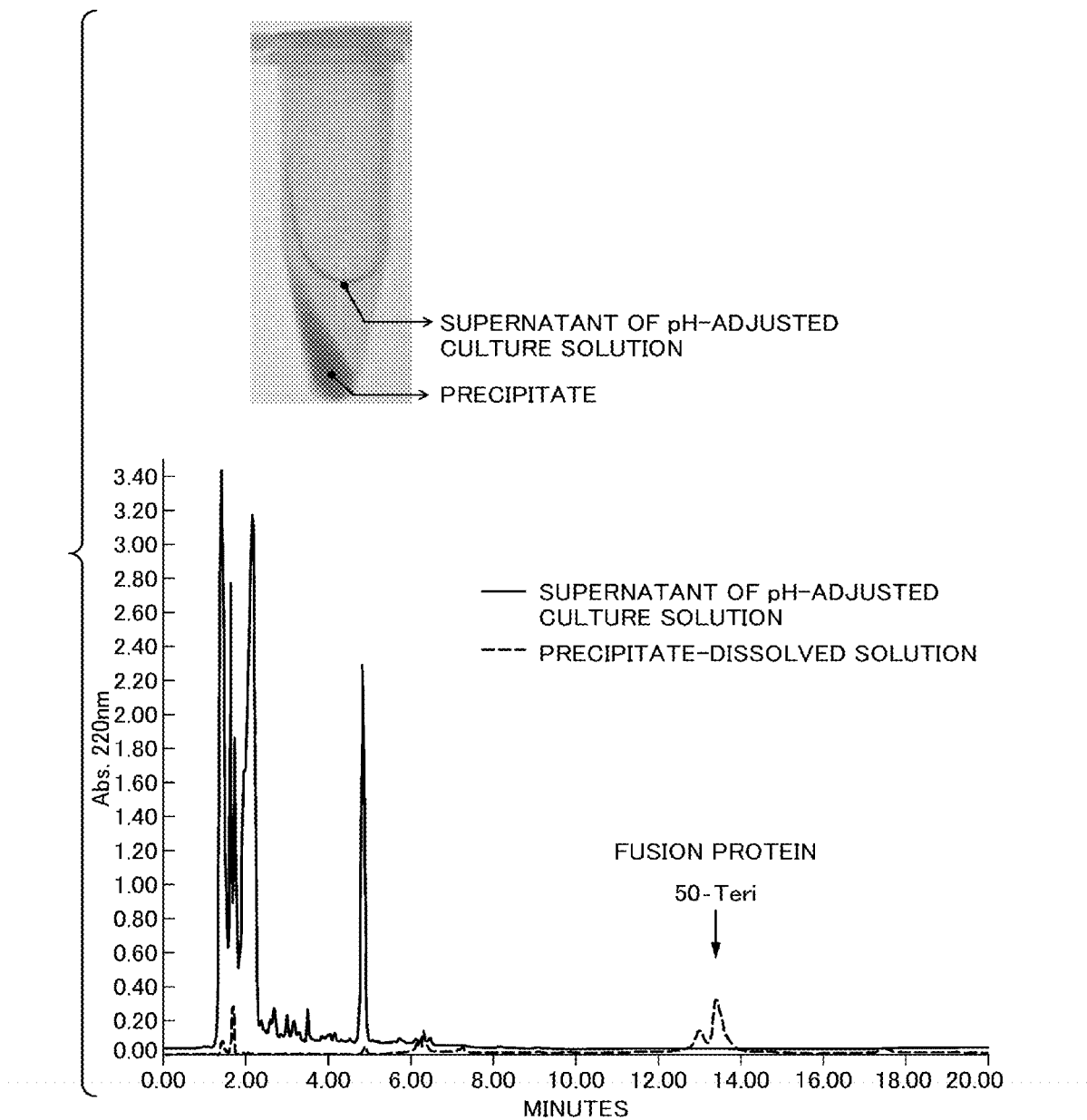

Moreover, the "supernatant of the pH-adjusted culture solution" at pH 4.9 and the corresponding "precipitate-dissolved solution" were subjected to a reversed-phase HPLC analysis to compare the fusion protein 50-Teri, impurities, and the like contained in the two. As a result, a large amount of impurities (for example, a peak group having a retention time of 0 minutes to 5 minutes) derived from the culture solution were detected in the "supernatant of the pH-adjusted culture solution"; meanwhile, impurity peaks other than the target fusion protein 50-Teri were hardly detected in the "precipitate-dissolved solution" (FIG. 1-2C). This revealed that the liquid-solid separation of the fusion protein by precipitation according to the present invention is applicable as a partial purification process.

Figures 1, 2, 2D:
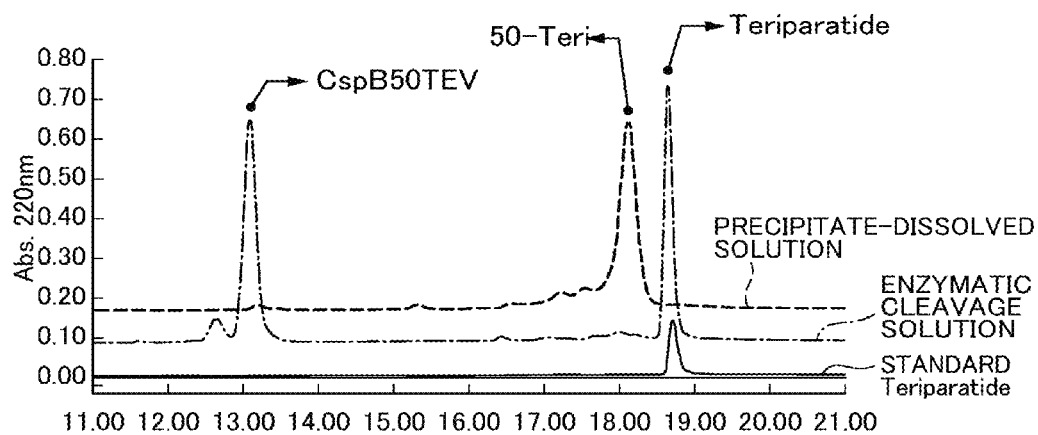

(5) Enzymatic Cleavage of Fusion Protein 50-Teri, and Acquisition of Target Protein Teriparatide The precipitated fusion protein 50-Teri obtained from the "pH-adjusted culture solution" having a pH adjusted to 4.9 in (4) above was washed with a 20 mM Tris HCl buffer (pH 5.0) to remove the culture solution attached to the precipitate. Next, the precipitate was dissolved into a buffer of 6 M urea +20 mM Tris HCl (pH 8.0), and a "precipitate-dissolved solution" was prepared. The "precipitate-dissolved solution" was diluted 10-fold by adding ultrapure water thereto, and then a ProTEV protease (capable of recognizing the amino acid sequence ENLYFQ in the fusion protein, Promega Corporation, V6102) was added to the resultant. Thereby, the fusion protein was enzymatically cleaved into CspB50TEV containing the protein having a self-assembly capability and the target protein teriparatide. Thus, an "enzymatic cleavage solution" was obtained. As a result of analyzing the enzymatic cleavage solution by reversed-phase HPLC, a peak believed to be of teriparatide was detected (FIG. 1-2D).

Subsequently, in order to confirm that the substance formed in the enzymatic cleavage solution was teriparatide, the "enzymatic cleavage solution" was subjected to reversed-phase HPLC. An eluate was obtained at a retention time of around 18.6 minutes under the above-described conditions of the reversed-phase HPLC, and then the substance believed to be teriparatide was purified. The purified substance was subjected to an N-terminal amino acid sequence analysis and mass spectrometry, and compared with standard Teriparatide (BACHEM, cat# H-4835).

The N-terminal amino acid sequence analysis was performed using a protein sequencer PPSQ-10 (manufactured by Shimadzu Corporation) based on the Edman degradation in accordance with the method (instruction manual) recommended by Shimadzu Corporation. The mass spectrometry was performed using AXIMA-TOF2 (manufactured by Shimadzu Corporation) based on MALDI-TOF-MS in accordance with the method (instruction manual) recommended by Shimadzu Corporation.

As a result of the N-terminal amino acid sequence analysis, amino acid residues on the N-terminal side of the purified substance matched 10 amino acid residues on the N-terminal side of standard Teriparatide.

Figures 1, 2, 2E:
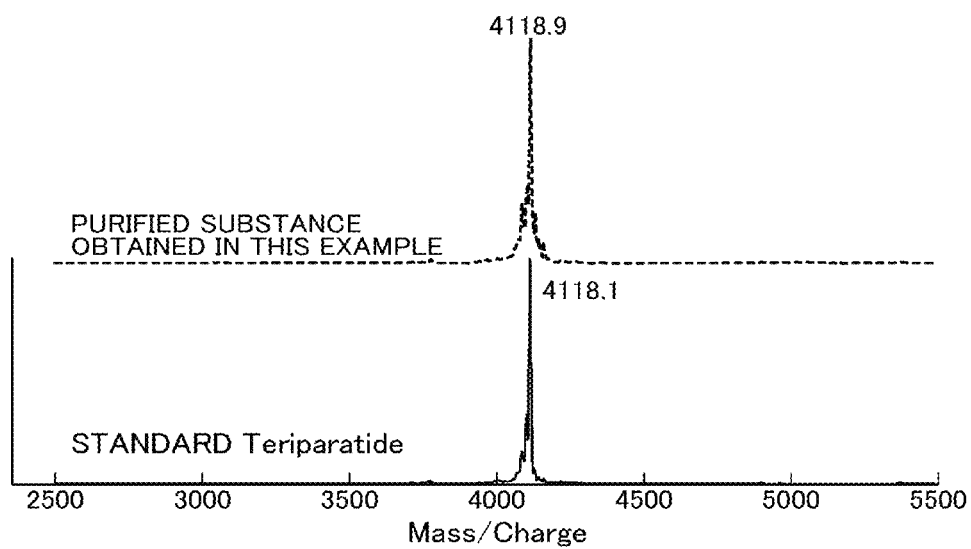

As a result of the mass spectrometry, when the purified substance was measured, the measurement mass of 4118.9 (the measurement error was ±0.1%) was detected; when standard Teriparatide was measured, the measurement mass of 4118.1 (the measurement error was ±0.1%) was detected (FIG. 1-2E). In other words, the measurement mass of the purified substance matched the measurement mass of standard Teriparatide. It was revealed that the purified substance was the target protein teriparatide. The purity of teriparatide obtained in this Example was 94%, which was calculated based on a peak area detected using reversed-phase HPLC according to the following equation:

the purity (%)=(the peak area of teriparatide/a total of all peak areas)×100.

Incidentally, the reversed-phase HPLC was carried out under the following conditions.
System: a set of Waters Alliance PDA system
Column: YMC-Pack C8 φ4.6×100 mm, particle diameter 5 μm, a pore diameter of 30 nm
Column temp.: 30° C.
Mobile phase A: aqueous solution of 10 mM ammonium acetate, aqueous solution of 10% acetonitrile, pH 7.0
Mobile phase B: aqueous solution of 10 mM ammonium acetate, aqueous solution of 80% acetonitrile, pH 7.0
Flow rate: 1.0 mL/min
Detection: 220 nm
Injection volume: 30 μL

| Gradient: Time (min) | A (%) | B (%) |
|---|---|---|
| 0 | 100 | 0 |
| 60 | 0 | 100 |

These results confirmed that the purified substance was teriparatide, and that the target protein can be obtained from the fusion protein.

Example 2

Production of Fusion Protein (CspB50Lvs-Bivalirudin18 (Abbreviated as 50-Biva18)) Having Portion of Bioactive Peptide Bivalirudin, and Production of Target Protein Bivalirudin18 (Abbreviated as Biva18)

In Example 2, a portion (18 amino acid residues) (Biva18) of a bioactive peptide bivalirudin was used as a target protein, a sequence consisting of 50 amino acid residues from the N-terminus of a CspB mature protein (CspB50) was used as a protein having a self-assembly capability, and a coryneform bacterium *C. glutamicum* was used as a host.

(1) Construction of Biva18-Secretory Expression Plasmid pPKK50Lys-Biva18 in *C. glutamicum*

A bioactive peptide bivalirudin known as an anticoagulant having a thrombin inhibitory activity is a peptide consisting of 20 residues in full length and having a D-phenylalanine residue at the N-terminus. In consideration of an amino acid sequence of 18-residue peptides (=Biva18) excluding an L-proline residue and the D-phenylalanine residue at the N-terminus and the codon usage in *C. glutamicum*, a total synthesis of <SEQ ID NO: 90> containing the Biva18 gene was performed.

Next, using the plasmid pPKK50Xa-PIns described in Example 1 (1) (iii) as a template, and using synthetic DNAs shown in <SEQ ID NO: 20> and <SEQ ID NO: 91> as primers, a region encoding the 5'-upstream region containing the promoter region of CspB, the 30 amino acid residues of the signal peptide at the N-terminus, the 50 residues on the N-terminal side of the mature cell surface protein, and a lysine residue was amplified by PCR. Then, using the amplified DNA fragment (the fragment of the region encoding the CspB promoter, the CspB signal peptide, the 50 residues in the N-terminal amino acid sequence of CspB, and the lysine residue) and the Biva18 gene fragment <SEQ ID NO: 90> as templates, and using DNAs shown in <SEQ ID NO: 20> and <SEQ ID NO: 92> as primers, a DNA fragment was obtained by PCR, in which the two DNA fragments were fused together. Note that the primers of <SEQ ID NO: 20> and <SEQ ID NO: 92> were each designed to have the restriction enzyme KpnI recognition sequence, and the primer of <SEQ ID NO: 91> was designed to have a sequence encoding the amino acid sequence on the N-terminal side of Biva18 so as to construct a fusion gene made of Biva18 and the base sequence encoding the 50 residues in the N-terminal amino acid sequence of CspB and the lysine residue. In the PCR reaction, Pyrobest DNA polymerase (manufactured by Takara Bio Inc.) was used, and the reaction conditions were in accordance with the manufacturer's recommended protocol. After restriction enzyme KpnI treatment, the DNA fragment was inserted in a KpnI site of pPK4 described in JP-A Hei 9-322774 to thus obtain a plasmid pPKK50Lys-Biva18. The result of determining the base sequence of the inserted fragment confirmed that the fusion gene was constructed as expected. Note that the base sequence was determined using BigDye (registered trademark) Terminator v3.1 Cycle Sequencing Kit (manufactured by Applied BioSystems Inc.) and 3130 Genetic Analyzer (manufactured by Applied BioSystems Inc.).

(2) Secretory Expression of Fusion Protein CspB50Lys-Bivalirudin18 (Abbreviated as 50-Biva18) Using pPKK50Lys-Biva18

Using pPKK50Lys-Biva18 constructed in (1), a *C. glutamicum* YDK010 strain described in WO01/23591 was transformed. The obtained transformed strain was cultured at 30° C. for 72 hours in MM liquid media (120 g of glucose, 0.4 g of magnesium sulfate heptahydrate, 30 g of ammonium sulfate, 1 g of potassium dihydrogen phosphate, 0.01 g of iron sulfate heptahydrate, 0.01 g of manganese sulfate pentahydrate, 200 μg of thiamine hydrochloride, 500 μg of biotin, 0.15 g of DL-methionine, 50 g of calcium carbonate, adjusted to 1 L with water and to pH 7.5) containing 25 mg/l of kanamycin. After the culturing was completed, each culture solution was centrifuged. The resulting culture supernatant was subjected to reducing SDS-PAGE. Staining with CBB R-250 (manufactured by Bio-Rad Laboratories, Inc.) showed a band of the target protein Bivalirudinl8.

On the other hand, the obtained transformed strain was cultured, while being agitated for aeration, at 30° C. for 3 days in a jar fermenter of 1 L capacity, in which 300 mL of a MMTG liquid medium (120 g of glucose, 2 g of calcium chloride, 3 g of magnesium sulfate heptahydrate, 3 g of ammonium sulfate, 1.5 g of potassium dihydrogen phosphate, 0.03 g of iron sulfate heptahydrate, 0.03 g of manganese sulfate pentahydrate, 450 µg of thiamine hydrochloride, 450 µg of biotin, 0.15 g of DL-methionine, 50 g of calcium carbonate, adjusted to 1 L with water and to pH 6.7) containing 25 mg/l of kanamycin had been charged and the pH was being maintained at 6.7 by adding an ammonia gas. After the culturing was completed, each culture solution was centrifuged. The resulting culture supernatant was subjected to reducing SDS-PAGE. Staining with CBB R-250 (manufactured by Bio-Rad Laboratories, Inc.) showed a band of the target protein.

(3) Removal of Microbial Cells from Culture Solution, and Storage of Microbial Cell-Removed Culture Solution
carried out in the same manner as in Example 1.

(4) Precipitation and Solubilization of Fusion Protein 50-Biva18 Due to pH Change The cryopreserved microbial cell-removed culture solution was thawed at 25° C. and centrifuged using a centrifuge at 12000 G for 1 minute to separate a precipitate mainly including an inorganic salt formed during the cryopreservation. To four microtubes, 0, 5, 10, and 30 µL of aqueous solutions of 0.5 M sulfuric acid and 30, 25, 20, and 0 µL of Milli Q water were respectively added and uniformly mixed. Then, 100 µL of the resulting centrifuged supernatant was dispensed into each of the tubes. All of the mixtures were adjusted to a volume of 130 µL.

After stirring, these were left alone for 10 minutes. Thereby, "pH-adjusted culture solutions" at pH 7.8, pH 4.7, pH 2.9, and pH 1.6 were obtained (corresponding to "solution obtained in step (2)"). The "pH-adjusted culture solutions" at pH 2.9 and pH 1.6 were clouded, and precipitation formation was observed. Those "pH-adjusted culture solutions" were centrifuged using a centrifuge at 12000 G for 5 minutes to separate precipitates formed by the pH change (corresponding to "solid separated in step (3)"). The resulting centrifuged supernatants were transferred as "supernatants of the pH-adjusted culture solutions" (corresponding to "solution after solid separation in step (3)") to different microtubes separately. To the separated precipitates, a buffer (100 mM Tris-HCl, pH 8.5) was added in the same volume as those of the supernatants of the pH-adjusted culture solutions. By stirring, the precipitates were immediately dissolved, and "precipitate-dissolved solutions" were obtained (corresponding to "solution obtained in step (4)"). All of the "precipitate-dissolved solutions" had a pH of around neutral, which were pH 8.3, pH 8.3, pH 8.1, and pH 7.8.

The "supernatants of the pH-adjusted culture solutions" at pH 7.8, pH 4.7, pH 2.9, and pH 1.6, and the "precipitate-dissolved solutions" obtained by the above-described operations were subjected to reducing SDS-PAGE, and bands of the fusion protein 50-Biva18 were checked to evaluate the precipitation and solubilization of the fusion protein 50-Biva18 due to the pH change.

The calculated recovery ratios of 50-Bival 8 from the "pH-adjusted culture solutions" at pH 7.8, pH 4.7, pH 2.9, and pH 1.6 were respectively 3%, 5%, 65%, and 63%. FIG. 2-A shows the relation between the calculated recovery ratio and the pH of the "pH-adjusted culture solutions."

FIG. 2-B shows the pH of the "pH-adjusted culture solutions," band portions of the fusion protein 50-Biva18 in images of electrophoresis of the "supernatants of the pH-adjusted culture solutions" and the corresponding "precipitate-dissolved solutions," and the recovery ratio.

The 50-Biva18 was present in the "supernatants of the pH-adjusted culture solutions" at pH 7.8 and pH 4.7. Weak bands thereof were detected in the "supernatants of the pH-adjusted culture solutions" at pH 2.9 and pH 1.6, while strong bands were detected in the "precipitate-dissolved solutions" at these pHs.

Next, by the same operations as above, a "pH-adjusted culture solution" having a pH of 3.0 lower than the pH value of approximately 4.5 at which the recovery ratio of 10% is achieved according to FIG. 2-A (the pH is the upper limit of the pH applicable in step (2)) was prepared and centrifuged. The resulting "supernatant of the pH-adjusted culture solution" and a corresponding "precipitate-dissolved solution" were subjected to a reversed-phase HPLC analysis to compare the fusion protein 50-Biva18, impurities, and the like contained in the two. As a result, a large amount of impurities (for example, a peak group having a retention time of 0 minutes to 10 minutes) derived from the culture solution were detected in the "supernatant of the pH-adjusted culture solution"; meanwhile, impurity peaks other than the target fusion protein 50-Biva18 were hardly detected in the "precipitate-dissolved solution" (FIG. 2-C).

Incidentally, the reversed-phase HPLC was carried out under the following conditions.
System: a set of Waters Alliance PDA system
Column: YMC-Triart C18 φ4.6×100 mm, a particle diameter of 10 5 µm, a pore diameter of 12 nm
Column temp.: 30° C.
Mobile phase A: aqueous solution of 10 mM ammonium acetate, aqueous solution of 10% acetonitrile, pH 7.0
Mobile phase B: aqueous solution of 10 mM ammonium acetate, aqueous solution of 80% acetonitrile, pH 7.0
Flow rate: 1.0 mL/min
Detection: 220 nm
Injection volume: 30 µL

| Gradient: Time (min) | A (%) | B (%) |
| --- | --- | --- |
| 0 | 100 | 0 |
| 25 | 50 | 50 |
| 28 | 0 | 100 |

(5) Enzymatic Cleavage of Fusion Protein 50-Biva18, and Acquisition of Target Protein Biva18

The precipitated fusion protein 50-Biva18 obtained from the "pH-adjusted culture solution" having a pH adjusted to 3.0 in (4) above was washed with a sulfuric acid solution of pH 3.0 to remove the culture solution attached to the precipitate. Next, the precipitate was dissolved into a buffer of 50 mM sodium bicarbonate (pH 8.3), and a "precipitate-dissolved solution" was prepared. To the precipitate-dissolved solution, trypsin (capable of recognizing the amino acid sequence Lys in the fusion protein, SIGMA-ALDRICH Co., T-303-10G) was added. Thus, an "enzymatic cleavage solution" was obtained. As a result of subjecting the enzymatic cleavage solution to reversed-phase HPLC, the peak of the fusion protein 50-Biva18, which was observed before the enzyme addition, was not detected; instead, other peaks were newly detected. This revealed that the cleavage reaction had favorably progressed (FIG. 2-D).

Subsequently, in order to confirm that the substance formed in the enzymatic cleavage solution was Biva18, the "enzymatic cleavage solution" was subjected to reversed-phase HPLC. An eluate was obtained at a retention time of around 5 minutes, and then the substance believed to be Biva18 was purified.

As a result of subjecting this purified substance to mass spectrometry to measure the mass, the measurement mass of 1935.8 at monoisotopic m/z (the measurement error was ±0.1%) was detected. On the other hand, the theoretical monoisotopic m/z calculated from the amino acid sequence of Biva18 was 1935.9, which was obtained as a result of inputting the sequence of Biva18 to MS-Isotope (http://prospector.ucsf.edu/prospector/cgi-bin/msform.cgi?form=msisotope). It was confirmed that this matched the measurement mass of 1935.8 detected from the purified substance (the measurement errorwas±0.1%) (FIG. 2-E). In other words, it was confirmed that the purified substance was the target protein Biva18.

The purity of Biva18 obtained in this Example was 92%, which was calculated based on a peak area detected using reversed-phase HPLC according to the following equation:

the purity (%)=(the peak area of Biva18/a total of all peak areas)×100

Incidentally, the reversed-phase HPLC was carried out under the following conditions.
System: a set of Waters Alliance PDA system
Column: YMC-Triart C18  4.6×100 mm, a particle diameter of 5 μm, a pore diameter of 12 nm
Column temp.: 30° C.
Mobile phase A: aqueous solution of 10 mM ammonium acetate, aqueous solution of 10% acetonitrile, pH 7.0
Mobile phase B: aqueous solution of 10 mM ammonium acetate, aqueous solution of 80% acetonitrile, pH 7.0
Flow rate: 1.0 mL/min
Detection: 220 nm
Injection volume: 30 μL

| Gradient: Time (min) | A (%) | B (%) |
|---|---|---|
| 0 | 100 | 0 |
| 25 | 50 | 50 |
| 28 | 0 | 100 |

These results confirmed that the purified substance was Biva18, and that the target protein can be obtained from the fusion protein.

Next, the "enzymatic cleavage solution" was subjected to strong anion exchange resin chromatography in place of the reversed-phase HPLC, and the Biva18 was purified.
<Chromatography Conditions>
Column: strong anion exchange resin (HiTrap Q FF, 1 mL, GE healthcare)
A buffer (binding): aqueous solution of 25 mM Na phosphate, pH 7.0
B buffer (elution): aqueous solution of 250 mM Na phosphate, pH 7.0
Flow rate: 1 mL/min
Detection: 280 nm
Amount of sample having been loaded: 0.3 mg-Biva18 (prepared with 250 μL of the enzymatic cleavage solution and 750 μL of A buffer)
Gradient elution: linear gradient, 0-100% B over 20 Column Volumes (CV)

As a result of the strong anion chromatography, all Biva18 contained in the enzymatic cleavage solution adsorbed to the resin. In the subsequent gradient elution, an eluate was obtained around 95% B and Biva18 was purified (FIG. 2-F). The purity of Biva18 thus obtained was 83%, which was calculated based on a peak area detected using reversed-phase HPLC according to the aforementioned equation (FIG. 2-G).

Example 3

Production of Fusion Protein CspB50TEV-Proinsulin (Abbreviated as 50-PIns) Having Proinsulin In Example 3, proinsulin (86 amino acid residues) (PIns), which is a proprotein of a bioactive peptide insulin, was used as a target protein, a sequence consisting of 50 amino acid residues from the N-terminus of a CspB mature protein (CspB50) was used as a protein having a self-assembly capability, and a coryneform bacterium C. glutamicum was used as a host.
(1) Secretory Expression of Fusion Protein 50-PIns Using pPKK50PIns Using the plasmid pPKK50PIns described in Example 1 (1) (ii), a C. glutamicum YDK010 strain described in WO01/23591 was transformed. The obtained transformed strain was cultured at 30° C. for 72 hours in MM liquid media (120 g of glucose, 0.4 g of magnesium sulfate heptahydrate, 30 g of ammonium sulfate, 1 g of potassium dihydrogen phosphate, 0.01 g of iron sulfate heptahydrate, 0.01 g of manganese sulfate pentahydrate, 200 μg of thiamine hydrochloride, 500 μg of biotin, 0.15 g of DL-methionine, 50 g of calcium carbonate, adjusted to 1 L with water and to pH 7.5) containing 25 mg/l of kanamycin. After the culturing was completed, each culture solution was centrifuged. The resulting culture supernatant was subjected to reducing SDS-PAGE. Staining with CBB R-250 (manufactured by Bio-Rad Laboratories, Inc.) showed a band of the target protein.
(2) Removal of Microbial Cells from Culture Solution, and Storage of Microbial Cell-Removed Culture Solution
carried out in the same manner as in Example 1.
(3) Precipitation and Solubilization of Fusion Protein 50-PIns Due to pH Change The cryopreserved microbial cell-removed culture solution was thawed at 25° C. and centrifuged using a centrifuge at 12000 G for 1 minute to separate a precipitate formed during the cryopreservation. To four microtubes, 0, 5, 10, and 30 μL of aqueous solutions of 0.5 M sulfuric acid and 30, 25, 20, and 0 μL of Milli Q water were respectively added and uniformly mixed. Then, 100 μL of the resulting centrifuged supernatant was dispensed into each of the tubes. All of the mixtures were adjusted to a volume of 130 μL.

After stirring, these were left alone for 10 minutes. Thereby, "pH-adjusted culture solutions" at pH 7.8, pH 4.8, pH 4.0, and pH 2.0 were obtained (corresponding to "solution obtained in step (2)"). The "pH-adjusted culture solutions" at pH 4.8, pH 4.0, and pH 2.0 were clouded, and precipitation formation was observed. Those "pH-adjusted culture solutions" were centrifuged using a centrifuge at 12000 G for 5 minutes to separate precipitates formed by the pH change (corresponding to "solid separated in step (3)"). The resulting centrifuged supernatants were transferred as "supernatants of the pH-adjusted culture solutions" (corresponding to "solution after solid separation in step (3)") to different microtubes separately. To the remaining precipitates, a buffer (100 mM Tris-HCl, pH 8.5) was added in the same volume as those of the centrifuged supernatants having been removed. By stirring, the precipitates were immediately dissolved, and "precipitate-dissolved solutions" were obtained (corresponding to "solution obtained in step (4)"); however, the precipitate formed at pH 2.0 was partially insoluble. All of the "precipitate-dissolved solutions" had a pH of around neutral, which were pH 8.3, pH 8.3, pH 8.3, and pH 8.3.

The "supernatants of the pH-adjusted culture solutions" at pH 7.8, pH 4.8, pH 4.0, and pH 2.0, and the "precipitate-dissolved solutions" obtained by the above-described operations were subjected to reducing SDS-PAGE, and bands of 50-PIns were checked to evaluate the precipitation and solubilization of 50-PIns due to the pH change.

The calculated recovery ratios of 50-PIns from the "pH-adjusted culture solutions" at pH 7.8, pH 4.8, pH 4.0, and pH 2.0 were respectively 1%, 54%, 58%, and 60%. FIG. 3-A shows the relation between the calculated recovery ratio and the pH of the "pH-adjusted culture solutions."

FIG. 3-B shows the pH of the "pH-adjusted culture solutions," band portions of the fusion protein 50-PIns in images of electrophoresis of the "supernatants of the pH-adjusted culture solutions" and the corresponding "precipitate-dissolved solutions," and the recovery ratio.

The 50-PIns was present in the "supernatant of the pH-adjusted culture solution" at pH 7.8. Weak bands thereof were detected in the "supernatants of the pH-adjusted culture solutions" at pH 4.8, pH 4.0, and pH 2.0, while strong bands were detected in the "precipitate-dissolved solutions" at these pHs.

Comparative Example 1

Production of Proinsulin Without Using Protein Having Self-Assembly Capability

In Comparative Example 1, proinsulin (86 amino acid residues) (PIns) was used as a target protein, and a coryneform bacterium *C. glutamicum* was used as a host. Nevertheless, no protein having a self-assembly capability was used.

(1) Secretory Expression of Proinsulin Using pPK-PIns

Using the plasmid pPKPIns described in Example 1 (1) (i), a *C. glutamicum* YDK010 strain described in WO001/23591 was transformed. The obtained transformed strain was cultured at 30° C. for 72 hours in MM liquid media (120 g of glucose, 0.4 g of magnesium sulfate heptahydrate, 30 g of ammonium sulfate, 1 g of potassium dihydrogen phosphate, 0.01 g of iron sulfate heptahydrate, 0.01 g of manganese sulfate pentahydrate, 200 μg of thiamine hydrochloride, 500 μg of biotin, 0.15 g of DL-methionine, 50 g of calcium carbonate, adjusted to 1 L with water and to pH 7.5) containing 25 mg/l of kanamycin. After the culturing was completed, each culture solution was centrifuged. The resulting culture supernatant was subjected to reducing SDS-PAGE. Staining with CBB R-250 (manufactured by Bio-Rad Laboratories, Inc.) showed a band of the target protein.

(2) Removal of Microbial Cells from Culture Solution, and Storage of Microbial Cell-Removed Culture Solution carried out in the same manner as in Example 1.

(3) Precipitation and Solubilization of Proinsulin (PIns) Due to pH Change

The cryopreserved microbial cell-removed culture solution was thawed at 25° C. and centrifuged using a centrifuge at 12000 G for 1 minute to separate a precipitate formed during the cryopreservation. To four microtubes, 0, 5, 10, and 30 μL of aqueous solutions of 0.5 M sulfuric acid and 30, 25, 20, and 0 μL of Milli Q water were respectively added and uniformly mixed. Then, 100 μL of the resulting centrifuged supernatant was dispensed into each of the tubes. All of the mixtures were adjusted to a volume of 130 μL.

After stirring, these were left alone for 10 minutes. Thereby, "pH-adjusted culture solutions" at pH 7.5, pH 4.6, pH 4.0, and pH 2.2 were obtained. The "pH-adjusted culture solution" at pH 2.2 was clouded, and precipitation formation was observed. Those "pH-adjusted culture solutions" were centrifuged using a centrifuge at 12000 G for 5 minutes to separate precipitates formed by the pH change. The resulting centrifuged supernatants were transferred as "supernatants of the pH-adjusted culture solutions" to different microtubes separately. To the remaining precipitates, a buffer (100 mM Tris-HCl, pH 8.5) was added in the same volume as those of the centrifuged supernatants having been removed. Even after stirring, the precipitate formed at pH 2.0 was partially insoluble. All of the obtained "precipitate-dissolved solutions" had a pH of around neutral, which were pH 8.4, pH 8.3, pH 8.3, and pH 8.1.

The "supernatants of the pH-adjusted culture solutions" at pH 7.5, pH 4.6, pH 4.0, and pH 2.2, and the "precipitate-dissolved solutions" obtained by the above-described operations were subjected to reducing SDS-PAGE, and bands of PIns were checked to evaluate the precipitation and solubilization of PIns due to the pH change.

The recovery ratios of PIns from the "pH-adjusted culture solutions" at pH 7.5, pH 4.6, pH 4.0, and pH 2.2 were respectively 7%, 6%, 0%, and 7%. FIG. 4-A shows the relation between the calculated recovery ratio and the pH of the "pH-adjusted culture solutions."

FIG. 4-B shows the pH of the "pH-adjusted culture solutions," band portions of the fusion protein PIns in images of electrophoresis of the "supernatants of the pH-adjusted culture solutions" and the corresponding "precipitate-dissolved solutions," and the recovery ratio.

The PIns was present in the "supernatant of the pH-adjusted culture solution" at pH 7.5 and also detected in the "supernatants of the pH-adjusted culture solutions" at pH 4.6, pH 4.0, and pH 2.2, but not detected in the "precipitate-dissolved solutions."

Example 4

Production of Fusion Protein Having Proinsulin

In Example 4, proinsulin (86 amino acid residues) (PIns) was used as a target protein, a sequence consisting of 250 amino acid residues from the N-terminus of a CspB mature protein (CspB250) was used as a protein having a self-assembly capability, and a coryneform bacterium *C. glutamicum* was used as a host.

(1) Secretory Expression of Fusion Protein CspB250TEV-Proinsulin (abbreviated as 250-PIns) Using pPKK250PIns Using the plasmid pPKK250PIns described in Example 1 (1) (ii), a *C. glutamicum* YDK010 strain described in WO01/23591 was transformed. The obtained transformed strain was cultured at 30° C. for 72 hours in MM liquid media (120 g of glucose, 0.4 g of magnesium sulfate heptahydrate, 30 g of ammonium sulfate, 1 g of potassium dihydrogen phosphate, 0.01 g of iron sulfate heptahydrate, 0.01 g of manganese sulfate pentahydrate, 200 μg of thiamine hydrochloride, 500 μg of biotin, 0.15 g of DL-methionine, 50 g of calcium carbonate, adjusted to 1 L with water and to pH 7.5) containing 25 mg/l of kanamycin. After the culturing was completed, each culture solution was centrifuged. The resulting culture supernatant was subjected to reducing SDS-PAGE. Staining with CBB R-250 (manufactured by Bio-Rad Laboratories, Inc.) showed a band of the target protein.

(2) Removal of Microbial Cells from Culture Solution, and Storage of Microbial Cell-Removed Culture Solution
carried out in the same manner as in Example 1.

(3) Precipitation and Solubilization of Fusion Protein 250-PIns Due to pH Change The cryopreserved microbial cell-removed culture solution was thawed at 25° C. and centrifuged using a centrifuge at 12000 G for 1 minute to separate a precipitate formed during the cryopreservation. To four microtubes, 0, 5, 10, and 30 μL of aqueous solutions of 0.5 M sulfuric acid and 30, 25, 20, and 0 μL of Milli Q water were respectively added and uniformly mixed. Then, 100 μL of the resulting centrifuged supernatant was dispensed into each of the tubes. All of the mixtures were adjusted to a volume of 130 μL.

After stirring, these were left alone for 10 minutes. Thereby, "pH-adjusted culture solutions" at pH 7.8, pH 4.4, pH 3.0, and pH 1.7 were obtained (corresponding to "solution obtained in step (2)"). The "pH-adjusted culture solutions" were not clouded, and no precipitation formation was observed visually. Those "pH-adjusted culture solutions" were centrifuged using a centrifuge at 12000 G for 5 minute. As a result, precipitates (corresponding to "solid separated in step (3)") were observed in the "pH-adjusted culture solutions" at pH 4.4 or lower. After these precipitates formed by the pH change were centrifuged, the resulting centrifuged supernatants were transferred as "supernatants of the pH-adjusted culture solutions" (corresponding to "solution after solid separation in step (3)") to different microtubes separately. To the remaining precipitates, a buffer (100 mM Tris-HCl, pH 8.5) was added in the same volume as those of the centrifuged supernatants having been removed. By stirring, the precipitates were immediately dissolved, and "precipitate-ssolved solutions" were obtained (corresponding to "solution obtained in step (4)"). All of the "precipitate-dissolved solutions" had a pH of around neutral, pH 8.3.

The "supernatants of the pH-adjusted culture solutions" at pH 7.8, pH 4.4, pH 3.0, and pH 1.7, and the "precipitate-dissolved solutions" obtained by the above-described operations were subjected to reducing SDS-PAGE, and bands of 250-PIns were checked to evaluate the precipitation and solubilization of 250-PIns due to the pH change. The calculated recovery ratios of 250-PIns from the "pH-adjusted culture solutions" at pH 7.8, pH 4.4, pH 3.0, and pH 1.7 were respectively 7%, 66%, 70%, and 74%. FIG. 5-A shows the relation between the calculated recovery ratio and the pH of the "pH-adjusted culture solutions."

FIG. 5-B shows the pH of the "pH-adjusted culture solutions," band portions of the fusion protein 250-PIns in images of electrophoresis of the "supernatants of the pH-adjusted culture solutions" and the corresponding "precipitate-dissolved solutions," and the recovery ratio.

The 250-PIns was present in the "supernatant of the pH-adjusted culture solution" at pH 7.8. Weak bands thereof were detected in the "supernatants of the pH-adjusted culture solutions" at pH 4.4, pH 3.0, and pH 1.7, while strong bands were detected in the "precipitate-dissolved solutions" at these pHs.

Example 5

Production of Fusion Protein Having Proinsulin

In Example 5, proinsulin (86 amino acid residues) (PIns) was used as a target protein, a sequence consisting of 17 amino acid residues from the N-terminus of a CspB mature protein (CspB17) was used as a protein having a self-assembly capability, and a coryneform bacterium C. glutamicum was used as a host.

(1) Secretory Expression of Fusion Protein CspB17TEV-Proinsulin (Abbreviated as 17-PIns) Using pPKK17PIns Using the plasmid pPKK17PIns described in Example 1 (1) (ii), a C. glutamicum YDK010 strain described in WO01/23591 was transformed. The obtained transformed strain was cultured at 30° C. for 72 hours in MM liquid media (120 g of glucose, 0.4 g of magnesium sulfate heptahydrate, 30 g of ammonium sulfate, 1 g of potassium dihydrogen phosphate, 0.01 g of iron sulfate heptahydrate, 0.01 g of manganese sulfate pentahydrate, 200 μg of thiamine hydrochloride, 500 μg of biotin, 0.15 g of DL-methionine, 50 g of calcium carbonate, adjusted to 1 L with water and to pH 7.5) containing 25 mg/l of kanamycin. After the culturing was completed, each culture solution was centrifuged. The resulting culture supernatant was subjected to reducing SDS-PAGE. Staining with CBB R-250 (manufactured by Bio-Rad Laboratories, Inc.) showed a band of the target protein.

(2) Removal of Microbial Cells from Culture Solution, and Storage of Microbial Cell-Removed Culture Solution
carried out in the same manner as in Example 1.

(3) Precipitation and Solubilization of Fusion Protein 17-PIns Due to pH Change

The cryopreserved microbial cell-removed culture solution was thawed at 25° C. and centrifuged using a centrifuge at 12000 G for 1 minute to separate a precipitate formed during the cryopreservation. To four microtubes, 0, 5, 10, and 30 μL of aqueous solutions of 0.5 M sulfuric acid and 30, 25, 20, and 0 μL of Milli Q water were respectively added and uniformly mixed. Then, 100 μL of the resulting centrifuged supernatant was 10 dispensed into each of the tubes. All of the mixtures were adjusted to a volume of 130 μL.

After stirring, these were left alone for 10 minutes. Thereby, "pH-adjusted culture solutions" at pH 7.8, pH 4.6, pH 3.7, and pH 2.0 were obtained (corresponding to "solution obtained instep (2)"). The "pH-adjusted culture solution" at pH 2.0 was clouded, and precipitation formation was observed. Those "pH-adjusted culture solutions" were centrifuged using a centrifuge at 12000 G for 5 minutes to separate precipitates formed by the pH change (corresponding to "solid separated in step (3)"). The resulting centrifuged supernatants were transferred as "supernatants of the pH-adjusted culture solutions" (corresponding to "solution after solid separation in step (3)") to different microtubes separately. To the remaining precipitates, a buffer (100 mM Tris-HCl, pH 8.5) was added in the same volume as those of the centrifuged supernatants having been removed. By stirring, the precipitates were immediately dissolved; however, the precipitate formed at pH was partially insoluble. All of the obtained "precipitate-dissolved solutions" (corresponding to "solution obtained in step (4)") had a pH of around neutral, pH 8.5.

The "supernatants of the pH-adjusted culture solutions" at pH 7.8, pH 4.6, pH 3.7, and pH 2.0, and the "precipitate-dissolved solutions" obtained by the above-described operations were subjected to reducing SDS-PAGE, and bands of 17-PIns were checked to evaluate the precipitation and solubilization of 17-PIns due to the pH change.

The recovery ratios of 17-PIns from the "pH-adjusted culture solutions" at pH 7.8, pH 4.6, pH 3.7, and pH 2.0 were respectively 9%, 46%, 43%, and 45%. FIG. 6-A shows the relation between the calculated recovery ratio and the pH of the "pH-adjusted culture solutions."

FIG. 6-B shows the pH of the "pH-adjusted culture solutions," band portions of the fusion protein 17-PIns in images of electrophoresis of the "supernatants of the pH-adjusted culture solutions" and the corresponding "precipitate-dissolved solutions," and the recovery ratio.

The 17-PIns was present in the "supernatant of the pH-adjusted culture solution" at pH 7. 8, and also detected as strong bands in the "precipitate-dissolved solutions" at pH 4.6, pH 3.7, and pH 2.0.

Example 6

Production of Fusion Protein Having Proinsulin

In Example 6, proinsulin (86 amino acid residues) (PIns) was used as a target protein, a sequence consisting of 6 amino acid residues from the N-terminus of a CspB mature protein (CspB6) was used as a protein having a self-assembly capability, and a coryneform bacterium *C. glutamicum* was used as a host.

(1) Secretory Expression of Fusion Protein CspB6TEV-Prinsulin (abbreviated as 6-PIns) Using pPKK6PIns Using the plasmid pPKK6PIns described in Example 1 (1) (ii), a *C. glutamicuin* YDK010 strain described in WO01/23591 was transformed. The obtained transformed strain was cultured at 30° C. for 72 hours in MM liquid media (120 g of glucose, 0.4 g of magnesium sulfate heptahydrate, 30 g of ammonium sulfate, 1 g of potassium dihydrogen phosphate, 0.01 g of iron sulfate heptahydrate, 0.01 g of manganese sulfate pentahydrate, 200 μg of thiamine hydrochloride, 500 μg of biotin, 0.15 g of DL-methionine, 50 g of calcium carbonate, adjusted to 1 L with water and to pH 7.5) containing 25 mg/l of kanamycin. After the culturing was completed, each culture solution was centrifuged. The resulting culture supernatant was subjected to reducing SDS-PAGE. Staining with CBB R-250 (manufactured by Bio-Rad Laboratories, Inc.) showed a band of the target protein.

(2) Removal of Microbial Cells from Culture Solution, and Storage of Microbial Cell-Removed Culture Solution carried out in the same manner as in Example 1.

(3) Precipitation and Solubilization of Fusion Protein 6-PIns Due to pH Change

The cryopreserved microbial cell-removed culture solution was thawed at 25° C. and centrifuged using a centrifuge at 12000 G for 1 minute to separate a precipitate formed during the cryopreservation. To four microtubes, 0, 5, 10, and 30 μL of aqueous solutions of 0.5 M sulfuric acid and 30, 25, 20, and 0 μL of Milli Q water were respectively added and uniformly mixed. Then, 100 μL of the resulting centrifuged supernatant was dispensed into each of the tubes. All of the mixtures were adjusted to a volume of 130 μL.

After stirring, these were left alone for 10 minutes. Thereby, "pH-adjusted culture solutions" at pH 7.6, pH 4.6, pH 3.5, and pH 1.8 were obtained (corresponding to "solution obtained instep (2)"). The "pH-adjusted culture solution" at pH 1.8 was clouded, and precipitation formation was observed. Those "pH-adjusted culture solutions" were centrifuged using a centrifuge at 12000 G for 5 minutes to separate precipitates formed by the pH change (corresponding to "solid separated in step (3)"). The resulting centrifuged supernatants were transferred as "supernatants of the pH-adjusted culture solutions" (corresponding to "solution after solid separation in step (3)") to different microtubes separately. To the remaining precipitates, a buffer (100 mM Tris-HCl, pH 8.5) was added in the same volume as those of the centrifuged supernatants having been removed. By stirring, the precipitates were immediately dissolved; however, the precipitate formed at pH 1.8 was partially insoluble. All of the obtained "precipitate-dissolved solutions" (corresponding to "solution obtained in step (4)") had a pH of around neutral, pH 8.5.

The "supernatants of the pH-adjusted culture solutions" at pH 7.6, pH 4.6, pH 3.5, and pH 1.8, and the "precipitate-dissolved solutions" obtained by the above-described operations were subjected to reducing SDS-PAGE, and bands of 6-PIns were checked to evaluate the precipitation and solubilization of 6-PIns due to the pH change.

The calculated recovery ratios of 6-PIns from the "pH-adjusted culture solutions" at pH 7.6, pH 4.6, pH 3.5, and pH 1.8 were respectively 3%, 34%, 31%, and 45%. FIG. 7-A shows the relation between the calculated recovery ratio and the pH of the "pH-adjusted culture solutions."

FIG. 7-B shows the pH of the "pH-adjusted culture solutions," band portions of the fusion protein 6-PIns in images of electrophoresis of the "supernatants of the pH-adjusted culture solutions" and the corresponding "precipitate-dissolved solutions," and the recovery ratio.

The 6-PIns was present in the "supernatant of the pH-adjusted culture solution" at pH 7.6, and also detected as bands in the "precipitate-dissolved solutions" at pH 4.6, pH 3.5, and pH 1.8.

Example 7

Production of Fusion Protein Having Teriparatide

In Example 7, in the same manner as in Example 1, a bioactive peptide teriparatide (34 amino acid residues) (Teri) was used as a target protein, a sequence consisting of 50 amino acid residues from the N-terminus of a CspB mature protein (CspB50) was used as a protein having a self-assembly capability, a proTEV protease recognition sequence was used as an amino acid sequence used for an enzymatic cleavage, and a coryneform bacterium *C. glutamicum* was used as a host.

Nevertheless, hydrochloric acid was used to adjust the pH of the solution containing the fusion protein (in Example 1, sulfuric acid was used).

(1) Construction of Teriparatide-Secretory Expression Plasmid (pPKK50TEV-Teri)

carried out in the same manner as in Example 1.

(2) Secretory Expression of Fusion Protein Using pPKK50TEV-Teri carried out in the same manner as in Example 1.

(3) Removal of Microbial Cells from Culture Solution, and Storage of Microbial Cell-Removed Culture Solution the same as in Example 1.

(4) Precipitation and Solubilization of Fusion Protein (Made of CspB50 and Teri (50-Teri)) Due to pH Change The cryopreserved microbial cell-removed culture solution was thawed at 25° C. and centrifuged using a centrifuge at 12000 G for 1 minute to separate a precipitate formed during the cryopreservation. To four microtubes, 0, 3.5, 5, and 10 μL of aqueous solutions of 1 M hydrochloric acid and 10, 6.5, 5, and 0 μL of Milli Q water were respectively added and uniformly mixed. Then, 100 μL of the resulting centrifuged supernatant was dispensed into each of the tubes. All of the mixtures were adjusted to a volume of 110 μL.

After stirring, these were left alone for 10 minutes. Thereby, "pH-adjusted culture solutions" at pH 7.9, pH 7.0, pH 5.3, and pH 3.1 were obtained (corresponding to "solution obtained in step (2)"). The "pH-adjusted culture solutions" at pH 7.0 or lower were clouded, and precipitation formation was observed. Those "pH-adjusted culture solutions" were centrifuged using a centrifuge at 12000 G for 5 minutes to separate precipitates formed by the pH change (corresponding to "solid separated in step (3)"). The resulting centrifuged supernatants were transferred as "supernatants of the pH-adjusted culture solutions" (corresponding to "solution after solid separation in step (3)") to different microtubes separately. To the remaining precipitates, a buffer (100 mM Tris-HCl, pH 8.5) was added in the same volume as those of the centrifuged supernatants having been removed. By stirring, the precipitates were immediately dissolved, and "precipitate-dissolved solutions" were obtained (corresponding to "solution obtained in step (4)"). All of the "precipitate-dissolved solutions" had a pH of around neutral, which were pH 8.5, pH 8.5, pH 8.4, and pH 8.3.

The "supernatants of the pH-adjusted culture solutions" at pH 7.9, pH 7.0, pH 5.3, and pH 3.1, and the "precipitate-dissolved solutions" obtained by the above-described operations were subjected to reducing SDS-PAGE and bands of 50-Teri were checked to evaluate the precipitation and solubilization of 50-Teri due to the pH change.

The calculated recovery ratios of 50-Teri from the "pH-adjusted culture solutions" at pH 7.9, pH 7.0, pH 5.3, and pH 3.1 were respectively 2%, 80%, 100%, and 99%. FIG. 8-A shows the relation between the calculated recovery ratio and the pH of the "pH-adjusted culture solutions."

FIG. 8-B shows the pH of the "pH-adjusted culture solutions," band portions of the fusion protein 50-Teri in images of electrophoresis of the "supernatants of the pH-adjusted culture solutions" and the corresponding "precipitate-dissolved solutions," and the recovery ratio.

The 50-Teri was present in the "supernatant of the pH-adjusted culture solution" at pH 7.9. The 50-Teri was not detected in the "supernatants of the pH-adjusted culture solutions" at pH 7.0, pH 5.3, and pH 3.1, but was detected in the corresponding "precipitate-dissolved solutions" at these pHs.

Example 8

Production of Fusion Protein Having Teriparatide

In Example 8, in the same manner as in Example 1, a bioactive peptide teriparatide (34 amino acid residues) (Teri) was used as a target protein, a sequence consisting of 50 amino acid residues from the N-terminus of a CspB mature protein (CspB50) was used as a protein having a self-assembly capability, a proTEV protease recognition sequence was used as an amino acid sequence used for an enzymatic cleavage, and a coryneform bacterium *C. glutamicum* was used as a host.

Nevertheless, acetic acid was used to adjust the pH of the solution containing the fusion protein (in Example 1, sulfuric acid was used).

(1) Construction of Teriparatide-Secretory Expression Plasmid (pPKK50TEV-Teri)

carried out in the same manner as in Example 1.

(2) Secretory Expression of Fusion Protein CspB50TEV-Teriparatide (abbreviated as 50-Teri) Using pPKK50TEV-Teri carried out in the same manner as in Example 1.

(3) Removal of Microbial Cells from Culture Solution, and Storage of Microbial Cell-Removed Culture Solution carried out in the same manner as in Example 1.

(4) Precipitation and Solubilization of Fusion Protein 50-Teri Due to pH Change

The cryopreserved microbial cell-removed culture solution was thawed at 25° C. and centrifuged using a centrifuge at 12000 G for 1 minute to separate a precipitate formed during the cryopreservation. To four microtubes, 0, 2, 4, and 10 µL of aqueous solutions of 10% acetic acid and 10, 8, 6, and 0 µL of Milli Q water were respectively added and uniformly mixed. Then, 100 µL of the resulting centrifuged supernatant was dispensed into each of the tubes. All of the mixtures were adjusted to a volume of 110 µL.

After stirring, these were left alone for 10 minutes. Thereby, "pH-adjusted culture solutions" at pH 7.9, pH 6.8, pH 5.0, and pH 4.3 were obtained (corresponding to "solution obtained in step (2)"). The "pH-adjusted culture solutions" at pH 6.8 or lower were clouded, and precipitation formation was observed. Those "pH-adjusted culture solutions" were centrifuged using a centrifuge at 12000 G for 5 minutes to separate precipitates formed by the pH change (corresponding to "solid separated in step (3)"). The resulting centrifuged supernatants were transferred as "supernatants of the pH-adjusted culture solutions" (corresponding to "solution after solid separation in step (3)") to different microtubes separately. To the remaining precipitates, a buffer (100 mM Tris-HCl, pH 8.5) was added in the same volume as those of the centrifuged supernatants having been removed. By stirring, the precipitates were immediately dissolved, and "precipitate-dissolved solutions" were obtained (corresponding to "solution obtained in step (4)"). All of the "precipitate-dissolved solutions" had a pH of around neutral, which were pH 8.5, pH 8.3, pH 8.1, and pH 7.9.

The "supernatants of the pH-adjusted culture solutions" at pH 7.9, pH 6.8, pH 5.0, and pH 4.3, and the "precipitate-dissolved solutions" obtained by the above-described operations were subjected to reducing SDS-PAGE, and bands of 50-Teri were checked to evaluate the precipitation and solubilization of 50-Teri due to the pH change.

The recovery ratios from the "pH-adjusted culture solutions" at pH 7.9, pH 6.8, pH 5.0, and pH 4.3 were respectively 2%, 95%, 99%, and 98%. FIG. 9-A shows the relation between the calculated recovery ratio and the pH of the "pH-adjusted culture solutions."

FIG. 9-B shows the pH of the "pH-adjusted culture solutions," band portions of the fusion protein 50-Teri in images of electrophoresis of the "supernatants of the pH-adjusted culture solutions" and the corresponding "precipitate-dissolved solutions," and the recovery ratio.

The 50-Teri was present in the "supernatant of the pH-adjusted culture solution" at pH 7.9. The 50-Teri was not detected in the "supernatants of the pH-adjusted culture solutions" at pH 6.8, pH 5.0, and pH 4.3, but was detected in the corresponding "precipitate-dissolved solutions" at these pHs.

Example 9

Production of Fusion Protein Having Teriparatide

In Example 9, in the same manner as in Example 1 and Example 1-2, a bioactive peptide teriparatide (34 amino acid residues) (Teri) was used as a target protein, a sequence consisting of 50 amino acid residues from the N-terminus of a CspB mature protein (CspB50) was used as a protein having a self-assembly capability, a proTEV protease recognition sequence was used as an amino acid sequence used for an enzymatic cleavage, and a coryneform bacterium *C. glutamicum* was used as a host.

(1) Construction of Teriparatide-Secretory Expression Plasmid (pPKK50TEV-Teri)

carried out in the same manner as in Example 1.

(2) Secretory Expression of Fusion Protein CspB50TEV-Teriparatide (Abbreviated as 50-Teri) Using pPKK50TEV-Teri
carried out in the same manner as in Example 1.
(3) Removal of Microbial Cells from Culture Solution, and Storage of Microbial Cell-Removed Culture Solution carried out in the same manner as in Example 1.
(4) Precipitation and Solubilization of Fusion Protein 50-Teri Due to pH Change and Evaluation of an Improvement of the Purity of 50-Teri The cryopreserved microbial cell-removed culture solution was thawed at 25° C. and centrifuged using a centrifuge at 12000 G for 1 minute to separate a precipitate formed during the cryopreservation. To microtube, 50 μL of aqueous solutions of 0.5M sulfuric acid and 600 μL of the resulting centrifuged supernatant were added.

After stirring, these were left alone for 10 minutes. Thereby, "pH-adjusted culture solution" at pH 3.7 was obtained (corresponding to "solution obtained in step (2)"). The pH value of 3.7 was used as "such a pH that a recovery ratio is 10% or more" based on the results of Example 1 and Example 1-2. The "pH-adjusted culture solution" was centrifuged using a centrifuge at 12000 G for 5 minutes to separate a precipitate formed by the pH change (corresponding to "solid separated in step (3)"). The resulting centrifuged supernatant was transferred as "supernatant of the pH-adjusted culture solution" (corresponding to "solution after solid separation in step (3)") to a different microtube. To the remaining precipitate, a buffer (100 mM Tris-HCl, pH 8.5) was added in the same volume as those of the centrifuged supernatant having been removed. By stirring, the precipitate was immediately dissolved, and "precipitate-dissolved solution" was obtained (corresponding to "solution obtained in step (4)"). The "precipitate-dissolved solution" had a pH of around neutral, which was pH 7.4. The pH value of 7.4 was used as "pH of 12 or below but higher than the pH of the solution obtained instep (2) by 0.1 or more" based on the results of Example 1 and Example 1-2.

The microbial cell-removed culture solution (before the above operations) and the "precipitate-dissolved solution" obtained by the above-described operations were subjected to reversed-phase HPLC to determine the peak areas of 50-Teri and so on and calculate the purity of 50-Teri in each solution according to the following equation. The calculated purities were compared.

the purity (%)=(the peak area of 50-Teri/total peak area)×100.

The conditions of the reversed-phase HPLC are shown below.
System: a set of Waters Alliance PDA system
Column: YMC-Pack C8 φ4.6×100 mm, a particle diameter of 5 μm,
a pore diameter of 30 nm
Column temp.: 30° C.
Mobile phase A: 10 mM ammonium acetate, 10% acetonitrile, pH 7.0 (non-adjusted pH value)
Mobile phase B: 10 mM ammonium acetate, 80% acetonitrile, pH 7.0 (non-adjusted pH value)
Flow rate: 1.0 mL/min
Detection: 280 nm, 220 nm
Injection volume: 30 μL

| Gradient: Time (min) | A (%) | B (%) |
|---|---|---|
| 0 | 100 | 0 |
| 5 | 74 | 26 |
| 25 | 64 | 36 |
| 30 | 0 | 100 |

Results of reversed-phase HPLC for each solution are shown in FIG. 10-A and FIG. 10-B. FIG. 10-A shows peaks detected at the wavelength of 280 nm. FIG. 10-B shows peaks detected at the wavelength of 220 nm.

When detected at the wavelength of 280 nm, the purity of 50-Teri in the microbial cell-removed culture solution was 11% while the purity of 50-Teri in the precipitate-dissolved solution was improved to 46% (FIG. 10-A). Similarly, when detected at the wavelength of 220 nm, the purity of 50-Teri in the microbial cell-removed culture solution was 46% while the purity of 50-Teri in the precipitate-dissolved solution was improved to 73% (FIG. 10-B).

This revealed that the above operations according to the present invention can achieve the improvement of the purity of 50-Teri as well as the recovery of 50-Teri.

INDUSTRIAL APPLICABILITY

The present invention can be utilized in methods for producing target proteins.

[Sequence Listing Free Text]
SEQ ID NO: 1: base sequence of cspB gene of *C. glutamicum* ATCC13869
SEQ ID NO: 2: amino acid sequence of CspB protein of *C. glutamicum* ATCC13869
SEQ ID NO: 3: amino acid sequence of CspB mature protein of *C. glutamicum* ATCC13869
SEQ ID NO: 4: amino acid sequence of signal peptide of *C. glutamicum*-derived PS1
SEQ ID NO: 5: amino acid sequence of signal peptide of *C. glutamicum*-derived PS2 (CspB)
SEQ ID NO: 6: amino acid sequence of signal peptide of *C. ammoniagenes*-derived SlpA (CspA)
SEQ ID NO: 7: Factor Xa protease recognition sequence
SEQ ID NO: 8: ProTEV protease recognition sequence
SEQ ID NOs: 9 to 16: base sequences of DNA for proinsulin total synthesis
SEQ ID NOs: 17, 18: primers
SEQ ID NO: 19: base sequence of proinsulin gene
SEQ ID NOs: 20 to 55: primers
SEQ ID NOs: 56 to 69: base sequences of DNA for human growth hormone hGH total synthesis
SEQ ID NOs: 70, 71: primers
SEQ ID NO: 72: base sequence of hGH gene
SEQ ID NOs: 73 to 77: primers
SEQ ID NOs: 78, 79: base sequences of DNA for teriparatide synthesis
SEQ ID NOs: 80, 81: primers
SEQ ID NO: 82: base sequence of teriparatide gene
SEQ ID NOs: 83 to 86: primers
SEQ ID NOs: 87 to 89: primers
SEQ ID NO: 90: base sequence of DNA for Biva18 synthesis
SEQ ID NOs: 91, 92: primers
SEQ ID NO: 93: amino acid sequence of Biva18

The invention claimed is:

1. A method of purifying a fusion protein, comprising:
(1) adjusting the pH of
an aqueous phase, comprising a fusion protein which is a fusion of a protein having a self-assembly capability and a target protein, and which aqueous phase has a first pH, to a second pH, to obtain a remaining aqueous phase and a solid fraction comprising an amount of said fusion protein;
(2) separating said solid fraction from said remaining aqueous phase, to obtain a separated solid fraction; and
(3) dissolving said separated solid fraction in a solution having a pH of 12 or lower but higher than said second pH by at least 0.1 pH units,
wherein said protein having a self-assembly capability is a cell surface protein that is a CspB mature protein or a portion thereof; and
wherein (i) said target protein has 10 to 300 amino acid residues, or (ii) the ratio of the number of amino acid residues in the target protein to the number of amino acid residues in the CspB mature protein or portion thereof is in a range of 0.3 to 14.

2. The method according to claim 1, wherein the CspB mature protein or the portion thereof is any one of the following (a) and (b):
(a) a protein or portion thereof consisting of an amino acid sequence of SEQ ID NO: 3; and
(b) a protein or portion thereof having a homology of 95% or more with the amino acid sequence of SEQ ID NO: 3.

3. The method according to claim 1, wherein the protein having a self-assembly capability is a portion of the CspB mature protein having a sequence consisting of 6 to 250 amino acid residues from the N-terminus of the CspB mature protein.

4. The method according to claim 3, wherein the portion of the CspB mature protein is a sequence consisting of 6, 17, 50, or 250 amino acid residues from the N-terminus of the CspB mature protein.

5. The method according to claim 1, wherein the number of amino acid residues in the target protein is 10 to 1000.

6. The method according to claim 1, wherein an amino acid sequence used for an enzymatic cleavage or a chemical cleavage is further incorporated between the protein having a self-assembly capability and the target protein.

7. The method according to claim 6, wherein the amino acid sequence used for the enzymatic cleavage between the protein having a self-assembly capability and the target protein is a ProTEV protease recognition sequence, a trypsin recognition sequence, or a Factor Xa protease recognition sequence.

8. The method according to claim 1, wherein the second pH is 9 or below.

9. The method according to claim 1, wherein the pH is adjusted using an acid selected from the group consisting of sulfuric acid, hydrochloric acid, acetic acid, phosphoric acid, and trifluoroacetic acid.

10. The method according to claim 1, wherein the separating of said solid fraction from said remaining aqueous phase is performed by centrifugation and/or membrane filtration.

11. The method according to claim 1, wherein the aqueous phase is a supernatant of a culture solution of a coryneform bacterium having a gene construct capable of expressing the fusion protein.

12. A method for producing a target protein, comprising:
(1) adjusting the pH of
an aqueous phase, comprising a fusion protein which is a fusion of a protein having a self-assembly capability, a target protein, and an amino acid sequence capable of enzymatic cleavage or a chemical cleavage located between said protein haying a self-assembly capability and said target protein, and which aqueous phase has a first pH, to a second pH, to obtain a remaining aqueous phase and a solid fraction comprising an amount of said fusion protein;
(2) separating said solid fraction from said remaining aqueous phase, to obtain a separated solid fraction;
(3) dissolving said separated solid fraction in a solution having a pH of 12 or lower but higher than said second pH by at least 0.1 pH units; and
(4) enzymatically or chemically cleaving said fusion protein at said site of said amino acid sequence located between said protein having a self-assembly capability and said target protein, either simultaneously with, during, or after said dissolving (3), to obtain said target protein,
wherein said protein having a self-assembly capability is a cell surface protein that is a CspB mature protein or a portion thereof; and
wherein (i) said target protein has 10 to 300 amino acid residues, or (ii) the ratio of the number of amino acid residues in the target protein to the number of amino acid residues in the CspB mature protein or portion thereof is in a range of 0.3 to 14.

13. The method according to claim 12, wherein said enzymatically or chemically cleaving of said fusion protein is an enzymatically cleaving.

14. The method according to claim 12, wherein the CspB mature protein or the portion thereof is any one of the following (a) and (b):
(a) a protein or portion thereof consisting of an amino acid sequence of SEQ ID NO: 3; and
(b) a protein or portion thereof having a homology of 95% or more with the amino acid sequence of SEQ ID NO: 3.

15. The method according to claim 12, wherein the protein having a self-assembly capability is a portion of the CspB mature protein having a sequence consisting of 6 to 250 amino acid residues from the N-terminus of the CspB mature protein.

16. The method according to claim 15, wherein the portion of the CspB mature protein is a sequence consisting of 6, 17, 50, or 250 amino acid residues from the N-terminus of the CspB mature protein.

17. The method according to claim 12, wherein the number of amino acid residues in the target protein is 10 to 1000.

18. The method according to claim 12, wherein the target protein is teriparatide.

19. The method according to claim 12, wherein the target protein is a bivalirudin intermediate represented by SEQ ID NO: 93.

20. The method according to claim 12, wherein said amino acid sequence capable of enzymatic cleavage or a chemical cleavage is a ProTEV protease recognition sequence, a trypsin recognition sequence, or a Factor Xa protease recognition sequence.

21. The method according to claim 12, wherein the second pH is 9 or below.

22. The method according to claim 12, wherein the pH is adjusted using an acid selected from the group consisting of sulfuric acid, hydrochloric acid, acetic acid, phosphoric acid, and trifluoroacetic acid.

23. The method according to claim 12, wherein the separating of said solid fraction from said remaining aqueous phase is performed by centrifugation and/or membrane filtration.

24. The method according to claim 12, wherein the aqueous phase is a supernatant of a culture solution of a coryneform bacterium having a gene construct capable of expressing the fusion protein.

25. The method according to claim 12, further comprising purifying said fusion protein after said dissolving (3), and/or purifying said target protein after said enzymatically or chemically cleaving (4).

26. The method according to claim 25, wherein said further purifying is performed by column chromatography.

27. A method for isolating a solid of a fusion protein, comprising:
(1) adjusting the pH of an aqueous phase, comprising a fusion protein which is a fusion of a protein having a self-assembly capability and a target protein, and which aqueous phase has a first pH, to a second pH, to obtain a remaining aqueous phase and a solid fraction comprising an amount of said fusion protein; and
(2) separating said solid fraction from said remaining aqueous phase, to obtain a separated solid fraction which comprises said fusion protein,
wherein said protein having a self-assembly capability is a cell surface protein that is a CspB mature protein or a portion thereof; and
wherein (i) said target protein has 10 to 300 amino acid residues, or (ii) the ratio of the number of amino acid residues in the target protein to the number of amino acid residues in the CspB mature protein or portion thereof is in a range of 0.3 to 14.

28. The method according to claim 1, wherein (i) said target protein has 10 to 300 amino acid residues.

29. The method according to claim 1, wherein (ii) the ratio of the number of amino acid residues in the target protein to the b of amino acid residues in the CspB mature protein or portion thereof is in a range of 0.3 to 14.

30. The method according to claim 12, wherein (i) said target protein has 10 to 300 amino acid residues.

31. The method according to claim 12, wherein (ii) the ratio of the number of amino acid residues in the target protein to the number of amino acid residues in the CspB mature protein or portion thereof is in a range of 0.3 to 14.

32. The method according to claim 27, wherein (i) said target protein has 10 to 300 amino acid residues.

33. The method according to claim 27, wherein (ii) the ratio of the number of amino acid residues in the target protein to the number of amino acid residues in the CspB mature protein or portion thereof is in a range of 0.3 to 14.

* * * * *

UNITED STATES PATENT AND TRADEMARK OFFICE
CERTIFICATE OF CORRECTION

PATENT NO. : 9,617,299 B2
APPLICATION NO. : 15/135012
DATED : April 11, 2017
INVENTOR(S) : Takahiro Nonaka et al.

Page 1 of 1

It is certified that error appears in the above-identified patent and that said Letters Patent is hereby corrected as shown below:

On the Title Page

Item (73), the Assignee's information has been listed incorrectly.
Item (73) should read:
-- (73) Assignee: AJINOMOTO CO., INC., Chuo-ku
(JP) --

Signed and Sealed this
Fifteenth Day of January, 2019

Andrei Iancu
*Director of the United States Patent and Trademark Office*

SEQUENCE LISTING

<160> NUMBER OF SEQ ID NOS: 93

<210> SEQ ID NO 1
<211> LENGTH: 1500
<212> TYPE: DNA
<213> ORGANISM: Corynebacterium glutamicum ATCC13869
<220> FEATURE:
<221> NAME/KEY: CDS
<222> LOCATION: (1)..(1500)

<400> SEQUENCE: 1

| atg | ttt | aac | aac | cgt | atc | cgc | act | gca | gct | ctc | gct | ggt | gca | atc | gca | 48 |
|---|---|---|---|---|---|---|---|---|---|---|---|---|---|---|---|---|
| Met | Phe | Asn | Asn | Arg | Ile | Arg | Thr | Ala | Ala | Leu | Ala | Gly | Ala | Ile | Ala | |
| 1 | | | | 5 | | | | | 10 | | | | | 15 | | |

| atc | tcc | acc | gca | gct | tcc | ggc | gta | gct | atc | cca | gca | ttc | gct | cag | gag | 96 |
|---|---|---|---|---|---|---|---|---|---|---|---|---|---|---|---|---|
| Ile | Ser | Thr | Ala | Ala | Ser | Gly | Val | Ala | Ile | Pro | Ala | Phe | Ala | Gln | Glu | |
| | | 20 | | | | | 25 | | | | | 30 | | | | |

| acc | aac | cca | acc | ttc | aac | atc | aac | aac | ggc | ttc | aac | gat | gct | gat | gga | 144 |
|---|---|---|---|---|---|---|---|---|---|---|---|---|---|---|---|---|
| Thr | Asn | Pro | Thr | Phe | Asn | Ile | Asn | Asn | Gly | Phe | Asn | Asp | Ala | Asp | Gly | |
| | | | 35 | | | | | 40 | | | | | 45 | | | |

| tcc | acc | atc | cag | cca | gtt | gag | cca | gtt | aac | cac | acc | gag | gaa | acc | ctc | 192 |
|---|---|---|---|---|---|---|---|---|---|---|---|---|---|---|---|---|
| Ser | Thr | Ile | Gln | Pro | Val | Glu | Pro | Val | Asn | His | Thr | Glu | Glu | Thr | Leu | |
| | 50 | | | | | 55 | | | | | 60 | | | | | |

| cgc | gac | ctg | act | gac | tcc | acc | ggc | gct | tac | ctg | gaa | gag | ttc | cag | tac | 240 |
|---|---|---|---|---|---|---|---|---|---|---|---|---|---|---|---|---|
| Arg | Asp | Leu | Thr | Asp | Ser | Thr | Gly | Ala | Tyr | Leu | Glu | Glu | Phe | Gln | Tyr | |
| 65 | | | | | 70 | | | | | 75 | | | | | 80 | |

| ggc | aac | gtt | gag | gaa | atc | gtt | gaa | gca | tac | ctg | cag | gtt | cag | gct | tcc | 288 |
|---|---|---|---|---|---|---|---|---|---|---|---|---|---|---|---|---|
| Gly | Asn | Val | Glu | Glu | Ile | Val | Glu | Ala | Tyr | Leu | Gln | Val | Gln | Ala | Ser | |
| | | | | 85 | | | | | 90 | | | | | 95 | | |

| gca | gac | gga | ttc | gat | cct | tct | gag | cag | gct | gct | tac | gag | gct | ttc | gag | 336 |
|---|---|---|---|---|---|---|---|---|---|---|---|---|---|---|---|---|
| Ala | Asp | Gly | Phe | Asp | Pro | Ser | Glu | Gln | Ala | Ala | Tyr | Glu | Ala | Phe | Glu | |
| | | | 100 | | | | | 105 | | | | | 110 | | | |

| gct | gct | cgc | gtt | cgt | gca | tcc | cag | gag | ctc | gcg | gct | tcc | gct | gag | acc | 384 |
|---|---|---|---|---|---|---|---|---|---|---|---|---|---|---|---|---|
| Ala | Ala | Arg | Val | Arg | Ala | Ser | Gln | Glu | Leu | Ala | Ala | Ser | Ala | Glu | Thr | |
| | | 115 | | | | | 120 | | | | | 125 | | | | |

| atc | act | aag | acc | cgc | gag | tcc | gtt | gct | tac | gca | ctc | aag | gct | gac | cgc | 432 |
|---|---|---|---|---|---|---|---|---|---|---|---|---|---|---|---|---|
| Ile | Thr | Lys | Thr | Arg | Glu | Ser | Val | Ala | Tyr | Ala | Leu | Lys | Ala | Asp | Arg | |
| | 130 | | | | | 135 | | | | | 140 | | | | | |

| gaa | gct | acc | gca | gct | ttc | gag | gct | tac | ctc | agc | gct | ctt | cgt | cag | gtt | 480 |
|---|---|---|---|---|---|---|---|---|---|---|---|---|---|---|---|---|
| Glu | Ala | Thr | Ala | Ala | Phe | Glu | Ala | Tyr | Leu | Ser | Ala | Leu | Arg | Gln | Val | |
| 145 | | | | | 150 | | | | | 155 | | | | | 160 | |

| tca | gtc | atc | aac | gat | ctg | atc | gct | gat | gct | aac | gcc | aag | aac | aag | act | 528 |
|---|---|---|---|---|---|---|---|---|---|---|---|---|---|---|---|---|
| Ser | Val | Ile | Asn | Asp | Leu | Ile | Ala | Asp | Ala | Asn | Ala | Lys | Asn | Lys | Thr | |
| | | | | 165 | | | | | 170 | | | | | 175 | | |

| gac | ttt | gca | gag | atc | gag | ctc | tac | gat | gtt | ctt | tac | acc | gac | gcc | gac | 576 |
|---|---|---|---|---|---|---|---|---|---|---|---|---|---|---|---|---|
| Asp | Phe | Ala | Glu | Ile | Glu | Leu | Tyr | Asp | Val | Leu | Tyr | Thr | Asp | Ala | Asp | |
| | | | 180 | | | | | 185 | | | | | 190 | | | |

| atc | tct | ggc | gat | gct | cca | ctt | ctt | gct | cct | gca | tac | aag | gag | ctg | aag | 624 |
|---|---|---|---|---|---|---|---|---|---|---|---|---|---|---|---|---|
| Ile | Ser | Gly | Asp | Ala | Pro | Leu | Leu | Ala | Pro | Ala | Tyr | Lys | Glu | Leu | Lys | |
| | | 195 | | | | | 200 | | | | | 205 | | | | |

| gac | ctt | cag | gct | gag | gtt | gac | gca | gac | ttc | gag | tgg | ttg | ggc | gag | ttc | 672 |
|---|---|---|---|---|---|---|---|---|---|---|---|---|---|---|---|---|
| Asp | Leu | Gln | Ala | Glu | Val | Asp | Ala | Asp | Phe | Glu | Trp | Leu | Gly | Glu | Phe | |
| | 210 | | | | | 215 | | | | | 220 | | | | | |

| gca | att | gat | aac | aat | gaa | gac | aac | tac | gtc | att | cgt | act | cac | atc | cct | 720 |
|---|---|---|---|---|---|---|---|---|---|---|---|---|---|---|---|---|
| Ala | Ile | Asp | Asn | Asn | Glu | Asp | Asn | Tyr | Val | Ile | Arg | Thr | His | Ile | Pro | |
| 225 | | | | | 230 | | | | | 235 | | | | | 240 | |

| gct | gta | gag | gca | ctc | aag | gca | gcg | atc | gat | tca | ctg | gtc | gac | acc | gtt | 768 |
|---|---|---|---|---|---|---|---|---|---|---|---|---|---|---|---|---|
| Ala | Val | Glu | Ala | Leu | Lys | Ala | Ala | Ile | Asp | Ser | Leu | Val | Asp | Thr | Val | |
| | | | | 245 | | | | | 250 | | | | | 255 | | |

```
gag cca ctt cgt gca gac gct atc gct aag aac atc gag gct cag aag    816
Glu Pro Leu Arg Ala Asp Ala Ile Ala Lys Asn Ile Glu Ala Gln Lys
        260                 265                 270 tct gac gtt ctg gtt ccc cag ctc ttc ctc gag cgt gca act gca cag    864
Ser Asp Val Leu Val Pro Gln Leu Phe Leu Glu Arg Ala Thr Ala Gln
    275                 280                 285 cgc gac acc ctg cgt gtt gta gag gca atc ttc tct acc tct gct cgt    912
Arg Asp Thr Leu Arg Val Val Glu Ala Ile Phe Ser Thr Ser Ala Arg
290                 295                 300 tac gtt gaa ctc tac gag aac gtc gag aac gtt aac gtt gag aac aag    960
Tyr Val Glu Leu Tyr Glu Asn Val Glu Asn Val Asn Val Glu Asn Lys
305                 310                 315                 320 acc ctt cgc cag cac tac tct tcc ctg atc cct aac ctc ttc atc gca   1008
Thr Leu Arg Gln His Tyr Ser Ser Leu Ile Pro Asn Leu Phe Ile Ala
        325                 330                 335 gcg gtt ggc aac atc aac gag ctc aac aat gca gat cag gct gca cgt   1056
Ala Val Gly Asn Ile Asn Glu Leu Asn Asn Ala Asp Gln Ala Ala Arg
    340                 345                 350 gag ctc ttc ctc gat tgg gac acc gac ctc acc acc aac gat gag gac   1104
Glu Leu Phe Leu Asp Trp Asp Thr Asp Leu Thr Thr Asn Asp Glu Asp
355                 360                 365 gaa gct tac tac cag gct aag ctc gac ttc gct atc gag acc tac gca   1152
Glu Ala Tyr Tyr Gln Ala Lys Leu Asp Phe Ala Ile Glu Thr Tyr Ala
370                 375                 380 aag atc ctg atc aac ggt gaa gtt tgg cag gag cca ctc gct tac gtc   1200
Lys Ile Leu Ile Asn Gly Glu Val Trp Gln Glu Pro Leu Ala Tyr Val
385                 390                 395                 400 cag aac ctg gat gca ggc gca cgt cag gaa gca gct gac cgc gaa gca   1248
Gln Asn Leu Asp Ala Gly Ala Arg Gln Glu Ala Ala Asp Arg Glu Ala
        405                 410                 415 gag cgc gca gct gac gca gca tac cgc gct gag cag ctc cgc atc gct   1296
Glu Arg Ala Ala Asp Ala Ala Tyr Arg Ala Glu Gln Leu Arg Ile Ala
    420                 425                 430 cag gaa gca gct gac gct cag aag gct ctc gct gag gct ctt gct aat   1344
Gln Glu Ala Ala Asp Ala Gln Lys Ala Leu Ala Glu Ala Leu Ala Asn
435                 440                 445 gca ggc aac aac gac aac ggt ggc gac aac tcc tcc gac gac aag gga   1392
Ala Gly Asn Asn Asp Asn Gly Gly Asp Asn Ser Ser Asp Asp Lys Gly
450                 455                 460 acc ggt tct tcc gac atc gga acc tgg gga cct ttc gca gca att gca   1440
Thr Gly Ser Ser Asp Ile Gly Thr Trp Gly Pro Phe Ala Ala Ile Ala
465                 470                 475                 480 gct atc atc gca gca atc gca gct atc ttc cca ttc ctc tcc ggt atc   1488
Ala Ile Ile Ala Ala Ile Ala Ala Ile Phe Pro Phe Leu Ser Gly Ile
        485                 490                 495 gtt aag ttc taa                                                    1500
Val Lys Phe <210> SEQ ID NO 2
<211> LENGTH: 499
<212> TYPE: PRT
<213> ORGANISM: Corynebacterium glutamicum ATCC13869

<400> SEQUENCE: 2

Met Phe Asn Asn Arg Ile Arg Thr Ala Ala Leu Ala Gly Ala Ile Ala
1               5                   10                  15

Ile Ser Thr Ala Ala Ser Gly Val Ala Ile Pro Ala Phe Ala Gln Glu
            20                  25                  30

Thr Asn Pro Thr Phe Asn Ile Asn Asn Gly Phe Asn Asp Ala Asp Gly
        35                  40                  45
```

```
Ser Thr Ile Gln Pro Val Glu Pro Val Asn His Thr Glu Glu Thr Leu
    50              55                  60

Arg Asp Leu Thr Asp Ser Thr Gly Ala Tyr Leu Glu Glu Phe Gln Tyr
 65              70                  75                      80

Gly Asn Val Glu Glu Ile Val Glu Ala Tyr Leu Gln Val Gln Ala Ser
                85                  90                  95

Ala Asp Gly Phe Asp Pro Ser Glu Gln Ala Ala Tyr Glu Ala Phe Glu
            100                 105                 110

Ala Ala Arg Val Arg Ala Ser Gln Leu Ala Ala Ser Ala Glu Thr
            115                 120                 125

Ile Thr Lys Thr Arg Glu Ser Val Ala Tyr Ala Leu Lys Ala Asp Arg
    130                 135                 140

Glu Ala Thr Ala Ala Phe Glu Ala Tyr Leu Ser Ala Leu Arg Gln Val
145                 150                 155                 160

Ser Val Ile Asn Asp Leu Ile Ala Asp Ala Asn Ala Lys Asn Lys Thr
                165                 170                 175

Asp Phe Ala Glu Ile Glu Leu Tyr Asp Val Leu Tyr Thr Asp Ala Asp
            180                 185                 190

Ile Ser Gly Asp Ala Pro Leu Leu Ala Pro Ala Tyr Lys Glu Leu Lys
    195                 200                 205

Asp Leu Gln Ala Glu Val Asp Ala Asp Phe Glu Trp Leu Gly Glu Phe
    210                 215                 220

Ala Ile Asp Asn Asn Glu Asp Asn Tyr Val Ile Arg Thr His Ile Pro
225                 230                 235                 240

Ala Val Glu Ala Leu Lys Ala Ala Ile Asp Ser Leu Val Asp Thr Val
                245                 250                 255

Glu Pro Leu Arg Ala Asp Ala Ile Ala Lys Asn Ile Glu Ala Gln Lys
            260                 265                 270

Ser Asp Val Leu Val Pro Gln Leu Phe Leu Glu Arg Ala Thr Ala Gln
    275                 280                 285

Arg Asp Thr Leu Arg Val Val Glu Ala Ile Phe Ser Thr Ser Ala Arg
    290                 295                 300

Tyr Val Glu Leu Tyr Glu Asn Val Glu Asn Val Asn Val Glu Asn Lys
305                 310                 315                 320

Thr Leu Arg Gln His Tyr Ser Ser Leu Ile Pro Asn Leu Phe Ile Ala
                325                 330                 335

Ala Val Gly Asn Ile Asn Glu Leu Asn Asn Ala Asp Gln Ala Ala Arg
            340                 345                 350

Glu Leu Phe Leu Asp Trp Asp Thr Asp Leu Thr Thr Asn Asp Glu Asp
            355                 360                 365

Glu Ala Tyr Tyr Gln Ala Lys Leu Asp Phe Ala Ile Glu Thr Tyr Ala
    370                 375                 380

Lys Ile Leu Ile Asn Gly Glu Val Trp Gln Glu Pro Leu Ala Tyr Val
385                 390                 395                 400

Gln Asn Leu Asp Ala Gly Ala Arg Gln Glu Ala Ala Asp Arg Glu Ala
                405                 410                 415

Glu Arg Ala Ala Asp Ala Tyr Arg Ala Glu Gln Leu Arg Ile Ala
            420                 425                 430

Gln Glu Ala Ala Asp Ala Gln Lys Ala Leu Ala Glu Ala Leu Ala Asn
            435                 440                 445

Ala Gly Asn Asn Asp Asn Gly Gly Asp Asn Ser Ser Asp Asp Lys Gly
450                 455                 460
```

-continued

Thr Gly Ser Ser Asp Ile Gly Thr Trp Gly Pro Phe Ala Ala Ile Ala
465                 470                 475                 480

Ala Ile Ile Ala Ala Ile Ala Ala Ile Phe Pro Phe Leu Ser Gly Ile
                485                 490                 495

Val Lys Phe

<210> SEQ ID NO 3
<211> LENGTH: 469
<212> TYPE: PRT
<213> ORGANISM: Corynebacterium glutamicum ATCC13869

<400> SEQUENCE: 3

Gln Glu Thr Asn Pro Thr Phe Asn Ile Asn Asn Gly Phe Asn Asp Ala
1               5                   10                  15

Asp Gly Ser Thr Ile Gln Pro Val Glu Pro Val Asn His Thr Glu Glu
            20                  25                  30

Thr Leu Arg Asp Leu Thr Asp Ser Thr Gly Ala Tyr Leu Glu Glu Phe
        35                  40                  45

Gln Tyr Gly Asn Val Glu Glu Ile Val Glu Ala Tyr Leu Gln Val Gln
    50                  55                  60

Ala Ser Ala Asp Gly Phe Asp Pro Ser Glu Gln Ala Ala Tyr Glu Ala
65                  70                  75                  80

Phe Glu Ala Ala Arg Val Arg Ala Ser Gln Glu Leu Ala Ala Ser Ala
                85                  90                  95

Glu Thr Ile Thr Lys Thr Arg Glu Ser Val Ala Tyr Ala Leu Lys Ala
            100                 105                 110

Asp Arg Glu Ala Thr Ala Ala Phe Glu Ala Tyr Leu Ser Ala Leu Arg
        115                 120                 125

Gln Val Ser Val Ile Asn Asp Leu Ile Ala Asp Ala Asn Ala Lys Asn
    130                 135                 140

Lys Thr Asp Phe Ala Glu Ile Glu Leu Tyr Asp Val Leu Tyr Thr Asp
145                 150                 155                 160

Ala Asp Ile Ser Gly Asp Ala Pro Leu Leu Ala Pro Ala Tyr Lys Glu
                165                 170                 175

Leu Lys Asp Leu Gln Ala Glu Val Asp Ala Asp Phe Glu Trp Leu Gly
            180                 185                 190

Glu Phe Ala Ile Asp Asn Asn Glu Asp Asn Tyr Val Ile Arg Thr His
        195                 200                 205

Ile Pro Ala Val Glu Ala Leu Lys Ala Ala Ile Asp Ser Leu Val Asp
    210                 215                 220

Thr Val Glu Pro Leu Arg Ala Asp Ala Ile Ala Lys Asn Ile Glu Ala
225                 230                 235                 240

Gln Lys Ser Asp Val Leu Val Pro Gln Leu Phe Leu Glu Arg Ala Thr
                245                 250                 255

Ala Gln Arg Asp Thr Leu Arg Val Val Glu Ala Ile Phe Ser Thr Ser
            260                 265                 270

Ala Arg Tyr Val Glu Leu Tyr Glu Asn Val Glu Asn Val Asn Val Glu
        275                 280                 285

Asn Lys Thr Leu Arg Gln His Tyr Ser Ser Leu Ile Pro Asn Leu Phe
    290                 295                 300

Ile Ala Ala Val Gly Asn Ile Asn Glu Leu Asn Asn Ala Asp Gln Ala
305                 310                 315                 320

Ala Arg Glu Leu Phe Leu Asp Trp Asp Thr Asp Leu Thr Thr Asn Asp
                325                 330                 335

-continued

```
Glu Asp Glu Ala Tyr Tyr Gln Ala Lys Leu Asp Phe Ala Ile Glu Thr
            340                 345                 350

Tyr Ala Lys Ile Leu Ile Asn Gly Glu Val Trp Gln Glu Pro Leu Ala
        355                 360                 365

Tyr Val Gln Asn Leu Asp Ala Gly Ala Arg Gln Glu Ala Ala Asp Arg
    370                 375                 380

Glu Ala Glu Arg Ala Ala Asp Ala Ala Tyr Arg Ala Glu Gln Leu Arg
385                 390                 395                 400

Ile Ala Gln Glu Ala Ala Asp Ala Gln Lys Ala Leu Ala Glu Ala Leu
                405                 410                 415

Ala Asn Ala Gly Asn Asn Asp Asn Gly Gly Asp Asn Ser Ser Asp Asp
            420                 425                 430

Lys Gly Thr Gly Ser Ser Asp Ile Gly Thr Trp Gly Pro Phe Ala Ala
        435                 440                 445

Ile Ala Ala Ile Ile Ala Ala Ile Ala Ile Phe Pro Phe Leu Ser
    450                 455                 460

Gly Ile Val Lys Phe
465

<210> SEQ ID NO 4
<211> LENGTH: 43
<212> TYPE: PRT
<213> ORGANISM: Corynebacterium glutamicum

<400> SEQUENCE: 4

Met Arg Asp Thr Ala Phe Arg Ser Ile Lys Ala Lys Ala Gln Ala Lys
1               5                   10                  15

Arg Arg Ser Leu Trp Ile Ala Ala Gly Ala Val Pro Thr Ala Ile Ala
            20                  25                  30

Leu Thr Met Ser Leu Ala Pro Met Ala Ser Ala
        35                  40

<210> SEQ ID NO 5
<211> LENGTH: 30
<212> TYPE: PRT
<213> ORGANISM: Corynebacterium glutamicum

<400> SEQUENCE: 5

Met Phe Asn Asn Arg Ile Arg Thr Ala Ala Leu Ala Gly Ala Ile Ala
1               5                   10                  15

Ile Ser Thr Ala Ala Ser Gly Val Ala Ile Pro Ala Phe Ala
            20                  25                  30

<210> SEQ ID NO 6
<211> LENGTH: 25
<212> TYPE: PRT
<213> ORGANISM: Corynebacterium ammoniagenes

<400> SEQUENCE: 6

Met Lys Arg Met Lys Ser Leu Ala Ala Ala Leu Thr Val Ala Gly Ala
1               5                   10                  15

Met Leu Ala Ala Pro Val Ala Thr Ala
            20                  25

<210> SEQ ID NO 7
<211> LENGTH: 4
<212> TYPE: PRT
<213> ORGANISM: Artificial Sequence
<220> FEATURE:
<223> OTHER INFORMATION: FactorXa
```

<400> SEQUENCE: 7

Ile Glu Gly Arg
1

<210> SEQ ID NO 8
<211> LENGTH: 6
<212> TYPE: PRT
<213> ORGANISM: Artificial Sequence
<220> FEATURE:
<223> OTHER INFORMATION: ProTEV

<400> SEQUENCE: 8

Glu Asn Leu Tyr Phe Gln
1               5

<210> SEQ ID NO 9
<211> LENGTH: 60
<212> TYPE: DNA
<213> ORGANISM: Artificial Sequence
<220> FEATURE:
<223> OTHER INFORMATION: PIns

<400> SEQUENCE: 9
atggcgctct ggatgcgcct gctgccactc ctggcgctcc tggcactgtg gggaccagat    60

<210> SEQ ID NO 10
<211> LENGTH: 60
<212> TYPE: DNA
<213> ORGANISM: Artificial Sequence
<220> FEATURE:
<223> OTHER INFORMATION: PIns

<400> SEQUENCE: 10
gggagccgca aagatgttgg ttcacgaagg cggcagcagg atctggtccc cacagtgcca    60

<210> SEQ ID NO 11
<211> LENGTH: 60
<212> TYPE: DNA
<213> ORGANISM: Artificial Sequence
<220> FEATURE:
<223> OTHER INFORMATION: PIns

<400> SEQUENCE: 11
ccaacatctt tgcggctccc acttggtgga ggcgctgtac cttgtctgcg gagagcgcgg    60

<210> SEQ ID NO 12
<211> LENGTH: 60
<212> TYPE: DNA
<213> ORGANISM: Artificial Sequence
<220> FEATURE:
<223> OTHER INFORMATION: PIns

<400> SEQUENCE: 12
atcttcggct tcgcgacgag tcttaggggt atagaagaat ccgcgctctc cgcagacaag    60

<210> SEQ ID NO 13
<211> LENGTH: 60
<212> TYPE: DNA
<213> ORGANISM: Artificial Sequence
<220> FEATURE:
<223> OTHER INFORMATION: PIns

<400> SEQUENCE: 13
ctcgtcgcga agccgaagat ctgcaggttg gtcaggtcga actgggcggc ggccctggtg    60

```
<210> SEQ ID NO 14
<211> LENGTH: 60
<212> TYPE: DNA
<213> ORGANISM: Artificial Sequence
<220> FEATURE:
<223> OTHER INFORMATION: PIns

<400> SEQUENCE: 14
tgcaaggagc cttccagggc gagtggctgg agggagccgg caccagggcc gccgcccagt      60

<210> SEQ ID NO 15
<211> LENGTH: 60
<212> TYPE: DNA
<213> ORGANISM: Artificial Sequence
<220> FEATURE:
<223> OTHER INFORMATION: PIns

<400> SEQUENCE: 15
gccctggaag gctccttgca aaacgcgga atcgtggagc agtgctgtac cagcatctgc      60

<210> SEQ ID NO 16
<211> LENGTH: 53
<212> TYPE: DNA
<213> ORGANISM: Artificial Sequence
<220> FEATURE:
<223> OTHER INFORMATION: PIns

<400> SEQUENCE: 16
tcagttgcag tagttctcaa gttggtagag ggagcagatg ctggtacagc act            53

<210> SEQ ID NO 17
<211> LENGTH: 25
<212> TYPE: DNA
<213> ORGANISM: Artificial Sequence
<220> FEATURE:
<223> OTHER INFORMATION: primer

<400> SEQUENCE: 17
ttcgtgaacc aacatctttg cggct                                           25

<210> SEQ ID NO 18
<211> LENGTH: 34
<212> TYPE: DNA
<213> ORGANISM: Artificial Sequence
<220> FEATURE:
<223> OTHER INFORMATION: primer

<400> SEQUENCE: 18
gcctctagat cagttgcagt agttctcaag ttgg                                 34

<210> SEQ ID NO 19
<211> LENGTH: 261
<212> TYPE: DNA
<213> ORGANISM: Artificial Sequence
<220> FEATURE:
<223> OTHER INFORMATION: PIns

<400> SEQUENCE: 19
ttcgtgaacc aacatctttg cggctcccac ttggtggagg cgctgtacct tgtctgcgga     60
gagcgcggat tcttctatac ccctaagact cgtcgcgaag ccgaagatct gcaggttggt    120
caggtcgaac tgggcggcgg ccctggtgcc ggctccctcc agccactcgc cctggaaggc    180
tccttgcaaa aacgcggaat cgtggagcag tgctgtacca gcatctgctc cctctaccaa    240
cttgagaact actgcaactg a                                              261
```

<210> SEQ ID NO 20
<211> LENGTH: 28
<212> TYPE: DNA
<213> ORGANISM: Artificial Sequence
<220> FEATURE:
<223> OTHER INFORMATION: primer

<400> SEQUENCE: 20
ggcggtaccc aaattcctgt gaagtagc    28

<210> SEQ ID NO 21
<211> LENGTH: 46
<212> TYPE: DNA
<213> ORGANISM: Artificial Sequence
<220> FEATURE:
<223> OTHER INFORMATION: primer

<400> SEQUENCE: 21
ccgcaaagat gttggttcac gaaagcgaat gctgggatag ctacgc    46

<210> SEQ ID NO 22
<211> LENGTH: 25
<212> TYPE: DNA
<213> ORGANISM: Artificial Sequence
<220> FEATURE:
<223> OTHER INFORMATION: primer

<400> SEQUENCE: 22
gatgtcggaa gaaccggttc ccttg    25

<210> SEQ ID NO 23
<211> LENGTH: 46
<212> TYPE: DNA
<213> ORGANISM: Artificial Sequence
<220> FEATURE:
<223> OTHER INFORMATION: primer

<400> SEQUENCE: 23
ccgcaaagat gttggttcac gaactgagcg aatgctggga tagcta    46

<210> SEQ ID NO 24
<211> LENGTH: 46
<212> TYPE: DNA
<213> ORGANISM: Artificial Sequence
<220> FEATURE:
<223> OTHER INFORMATION: primer

<400> SEQUENCE: 24
ccgcaaagat gttggttcac gaactcctga gcgaatgctg ggatag    46

<210> SEQ ID NO 25
<211> LENGTH: 46
<212> TYPE: DNA
<213> ORGANISM: Artificial Sequence
<220> FEATURE:
<223> OTHER INFORMATION: primer

<400> SEQUENCE: 25
ccgcaaagat gttggttcac gaaggtctcc tgagcgaatg ctggga    46

<210> SEQ ID NO 26
<211> LENGTH: 46
<212> TYPE: DNA
<213> ORGANISM: Artificial Sequence
<220> FEATURE:
<223> OTHER INFORMATION: primer

<400> SEQUENCE: 26
ccgcaaagat gttggttcac gaagttggtc tcctgagcga atgctg        46

<210> SEQ ID NO 27
<211> LENGTH: 46
<212> TYPE: DNA
<213> ORGANISM: Artificial Sequence
<220> FEATURE:
<223> OTHER INFORMATION: primer

<400> SEQUENCE: 27
ccgcaaagat gttggttcac gaatgggttg gtctcctgag cgaatg        46

<210> SEQ ID NO 28
<211> LENGTH: 46
<212> TYPE: DNA
<213> ORGANISM: Artificial Sequence
<220> FEATURE:
<223> OTHER INFORMATION: primer

<400> SEQUENCE: 28
ccgcaaagat gttggttcac gaaggttggg ttggtctcct gagcga        46

<210> SEQ ID NO 29
<211> LENGTH: 46
<212> TYPE: DNA
<213> ORGANISM: Artificial Sequence
<220> FEATURE:
<223> OTHER INFORMATION: primer

<400> SEQUENCE: 29
ccgcaaagat gttggttcac gaagaaggtt gggttggtct cctgag        46

<210> SEQ ID NO 30
<211> LENGTH: 46
<212> TYPE: DNA
<213> ORGANISM: Artificial Sequence
<220> FEATURE:
<223> OTHER INFORMATION: primer

<400> SEQUENCE: 30
ccgcaaagat gttggttcac gaagttgaag gttgggttgg tctcct        46

<210> SEQ ID NO 31
<211> LENGTH: 46
<212> TYPE: DNA
<213> ORGANISM: Artificial Sequence
<220> FEATURE:
<223> OTHER INFORMATION: primer

<400> SEQUENCE: 31
ccgcaaagat gttggttcac gaagatgttg aaggttgggt tggtct        46

<210> SEQ ID NO 32
<211> LENGTH: 46
<212> TYPE: DNA
<213> ORGANISM: Artificial Sequence
<220> FEATURE:
<223> OTHER INFORMATION: primer

<400> SEQUENCE: 32
ccgcaaagat gttggttcac gaagttgatg ttgaaggttg ggttgg        46

<210> SEQ ID NO 33
<211> LENGTH: 46

```
<212> TYPE: DNA
<213> ORGANISM: Artificial Sequence
<220> FEATURE:
<223> OTHER INFORMATION: primer

<400> SEQUENCE: 33
ccgcaaagat gttggttcac gaagttgttg atgttgaagg ttgggt          46

<210> SEQ ID NO 34
<211> LENGTH: 46
<212> TYPE: DNA
<213> ORGANISM: Artificial Sequence
<220> FEATURE:
<223> OTHER INFORMATION: primer

<400> SEQUENCE: 34
ccgcaaagat gttggttcac gaagccgttg ttgatgttga aggttg          46

<210> SEQ ID NO 35
<211> LENGTH: 46
<212> TYPE: DNA
<213> ORGANISM: Artificial Sequence
<220> FEATURE:
<223> OTHER INFORMATION: primer

<400> SEQUENCE: 35
ccgcaaagat gttggttcac gaagaagccg ttgttgatgt tgaagg          46

<210> SEQ ID NO 36
<211> LENGTH: 46
<212> TYPE: DNA
<213> ORGANISM: Artificial Sequence
<220> FEATURE:
<223> OTHER INFORMATION: primer

<400> SEQUENCE: 36
ccgcaaagat gttggttcac gaagttgaag ccgttgttga tgttga          46

<210> SEQ ID NO 37
<211> LENGTH: 46
<212> TYPE: DNA
<213> ORGANISM: Artificial Sequence
<220> FEATURE:
<223> OTHER INFORMATION: primer

<400> SEQUENCE: 37
ccgcaaagat gttggttcac gaaatcgttg aagccgttgt tgatgt          46

<210> SEQ ID NO 38
<211> LENGTH: 46
<212> TYPE: DNA
<213> ORGANISM: Artificial Sequence
<220> FEATURE:
<223> OTHER INFORMATION: primer

<400> SEQUENCE: 38
ccgcaaagat gttggttcac gaaatcagca tcgttgaagc cgttgt          46

<210> SEQ ID NO 39
<211> LENGTH: 46
<212> TYPE: DNA
<213> ORGANISM: Artificial Sequence
<220> FEATURE:
<223> OTHER INFORMATION: primer

<400> SEQUENCE: 39
```
ccgcaaagat gttggttcac gaaggtggat ccatcagcat cgttga    46

<210> SEQ ID NO 40
<211> LENGTH: 46
<212> TYPE: DNA
<213> ORGANISM: Artificial Sequence
<220> FEATURE:
<223> OTHER INFORMATION: primer

<400> SEQUENCE: 40
ccgcaaagat gttggttcac gaagtactgg aactcttcca ggtaag    46

<210> SEQ ID NO 41
<211> LENGTH: 46
<212> TYPE: DNA
<213> ORGANISM: Artificial Sequence
<220> FEATURE:
<223> OTHER INFORMATION: primer

<400> SEQUENCE: 41
ccgcaaagat gttggttcac gaaagtgatg gtctcagcgg aagccg    46

<210> SEQ ID NO 42
<211> LENGTH: 46
<212> TYPE: DNA
<213> ORGANISM: Artificial Sequence
<220> FEATURE:
<223> OTHER INFORMATION: primer

<400> SEQUENCE: 42
ccgcaaagat gttggttcac gaactctgca aagtcagtct tgttct    46

<210> SEQ ID NO 43
<211> LENGTH: 46
<212> TYPE: DNA
<213> ORGANISM: Artificial Sequence
<220> FEATURE:
<223> OTHER INFORMATION: primer

<400> SEQUENCE: 43
ccgcaaagat gttggttcac gaattcattg ttatcaattg cgaact    46

<210> SEQ ID NO 44
<211> LENGTH: 46
<212> TYPE: DNA
<213> ORGANISM: Artificial Sequence
<220> FEATURE:
<223> OTHER INFORMATION: primer

<400> SEQUENCE: 44
ccgcaaagat gttggttcac gaagagctgg ggaaccagaa cgtcag    46

<210> SEQ ID NO 45
<211> LENGTH: 46
<212> TYPE: DNA
<213> ORGANISM: Artificial Sequence
<220> FEATURE:
<223> OTHER INFORMATION: primer

<400> SEQUENCE: 45
ccgcaaagat gttggttcac gaagatcagg gaagagtagt gctggc    46

<210> SEQ ID NO 46
<211> LENGTH: 46
<212> TYPE: DNA
<213> ORGANISM: Artificial Sequence -continued
<220> FEATURE:
<223> OTHER INFORMATION: primer

<400> SEQUENCE: 46
ccgcaaagat gttggttcac gaagatagcg aagtcgagct tagcct          46

<210> SEQ ID NO 47
<211> LENGTH: 46
<212> TYPE: DNA
<213> ORGANISM: Artificial Sequence
<220> FEATURE:
<223> OTHER INFORMATION: primer

<400> SEQUENCE: 47
ccgcaaagat gttggttcac gaagcggagc tgctcagcgc ggtatg          46

<210> SEQ ID NO 48
<211> LENGTH: 46
<212> TYPE: DNA
<213> ORGANISM: Artificial Sequence
<220> FEATURE:
<223> OTHER INFORMATION: primer

<400> SEQUENCE: 48
ccgcaaagat gttggttcac gaagatgtcg gaagaaccgg ttccct          46

<210> SEQ ID NO 49
<211> LENGTH: 34
<212> TYPE: DNA
<213> ORGANISM: Artificial Sequence
<220> FEATURE:
<223> OTHER INFORMATION: primer

<400> SEQUENCE: 49
gccggtacct cagttgcagt agttctcaag ttgg          34

<210> SEQ ID NO 50
<211> LENGTH: 46
<212> TYPE: DNA
<213> ORGANISM: Artificial Sequence
<220> FEATURE:
<223> OTHER INFORMATION: primer

<400> SEQUENCE: 50
tggttcacga agcggccctc gatatcagca tcgttgaagc cgttgt          46

<210> SEQ ID NO 51
<211> LENGTH: 46
<212> TYPE: DNA
<213> ORGANISM: Artificial Sequence
<220> FEATURE:
<223> OTHER INFORMATION: primer

<400> SEQUENCE: 51
tggttcacga agcggccctc gatgtactgg aactcttcca ggtaag          46

<210> SEQ ID NO 52
<211> LENGTH: 35
<212> TYPE: DNA
<213> ORGANISM: Artificial Sequence
<220> FEATURE:
<223> OTHER INFORMATION: primer

<400> SEQUENCE: 52
atcgagggcc gcttcgtgaa ccaacatctt tgcgg          35

<210> SEQ ID NO 53
<211> LENGTH: 41
<212> TYPE: DNA
<213> ORGANISM: Artificial Sequence
<220> FEATURE:
<223> OTHER INFORMATION: primer

<400> SEQUENCE: 53
gaaaacctgt acttccagtt cgtgaaccaa catctttgcg g                     41

<210> SEQ ID NO 54
<211> LENGTH: 46
<212> TYPE: DNA
<213> ORGANISM: Artificial Sequence
<220> FEATURE:
<223> OTHER INFORMATION: primer

<400> SEQUENCE: 54
tggttcacga agcggccctc gatggttggg ttggtctcct gagcga                46

<210> SEQ ID NO 55
<211> LENGTH: 46
<212> TYPE: DNA
<213> ORGANISM: Artificial Sequence
<220> FEATURE:
<223> OTHER INFORMATION: primer

<400> SEQUENCE: 55
acgaactgga agtacaggtt ttcggttggg ttggtctcct gagcga                46

<210> SEQ ID NO 56
<211> LENGTH: 60
<212> TYPE: DNA
<213> ORGANISM: Artificial Sequence
<220> FEATURE:
<223> OTHER INFORMATION: hGH

<400> SEQUENCE: 56
tttccaacaa tcccgctgag ccgcctcttc gataacgctt cgctccgcgc tcaccgcctg    60

<210> SEQ ID NO 57
<211> LENGTH: 60
<212> TYPE: DNA
<213> ORGANISM: Artificial Sequence
<220> FEATURE:
<223> OTHER INFORMATION: hGH

<400> SEQUENCE: 57
gtaccaggaa ttcgaggaag cgtatattcc caaggaacag aaatactcgt ttctccaaaa    60

<210> SEQ ID NO 58
<211> LENGTH: 60
<212> TYPE: DNA
<213> ORGANISM: Artificial Sequence
<220> FEATURE:
<223> OTHER INFORMATION: hGH

<400> SEQUENCE: 58
tttccgagtc gattcctacc ccctccaatc gtgaggaaac ccagcaaaaa agcaacctcg    60

<210> SEQ ID NO 59
<211> LENGTH: 60
<212> TYPE: DNA
<213> ORGANISM: Artificial Sequence
<220> FEATURE:
<223> OTHER INFORMATION: hGH

<400> SEQUENCE: 59
cttcttatcc agtcctggct ggagcccgtg cagttttttgc gcagcgtctt tgctaactct        60

<210> SEQ ID NO 60
<211> LENGTH: 60
<212> TYPE: DNA
<213> ORGANISM: Artificial Sequence
<220> FEATURE:
<223> OTHER INFORMATION: hGH

<400> SEQUENCE: 60
ttccaacgtg tacgatcttt tgaaggatct cgaagagggt attcagactc tgatgggccg        60

<210> SEQ ID NO 61
<211> LENGTH: 60
<212> TYPE: DNA
<213> ORGANISM: Artificial Sequence
<220> FEATURE:
<223> OTHER INFORMATION: hGH

<400> SEQUENCE: 61
gcacgggcca aattttcaag caaacctaca gcaaatttga tactaactcc cacaatgacg        60

<210> SEQ ID NO 62
<211> LENGTH: 60
<212> TYPE: DNA
<213> ORGANISM: Artificial Sequence
<220> FEATURE:
<223> OTHER INFORMATION: hGH

<400> SEQUENCE: 62
ggtctgctct actgcttctt caaggatatg gataaggtcg aaaccttcct ccgtatcgtg        60

<210> SEQ ID NO 63
<211> LENGTH: 60
<212> TYPE: DNA
<213> ORGANISM: Artificial Sequence
<220> FEATURE:
<223> OTHER INFORMATION: hGH

<400> SEQUENCE: 63
cttcctcgaa ttcctggtac gtgtcgaacg cgagttggtg caggcggtga gcgcggagcg        60

<210> SEQ ID NO 64
<211> LENGTH: 60
<212> TYPE: DNA
<213> ORGANISM: Artificial Sequence
<220> FEATURE:
<223> OTHER INFORMATION: hGH

<400> SEQUENCE: 64
ggtaggaatc gactcggaaa agcagaggct ggtttggggg ttttggagaa acgagtattt        60

<210> SEQ ID NO 65
<211> LENGTH: 60
<212> TYPE: DNA
<213> ORGANISM: Artificial Sequence
<220> FEATURE:
<223> OTHER INFORMATION: hGH

<400> SEQUENCE: 65
agccaggact ggataagaag cagtgagata cgcagcaact cgaggttgct tttttgctgg       60

<210> SEQ ID NO 66

```
<211> LENGTH: 60
<212> TYPE: DNA
<213> ORGANISM: Artificial Sequence
<220> FEATURE:
<223> OTHER INFORMATION: hGH

<400> SEQUENCE: 66
aaagatcgta cacgttggaa tccgacgctc catacacaag agagttagca aagacgctgc    60

<210> SEQ ID NO 67
<211> LENGTH: 60
<212> TYPE: DNA
<213> ORGANISM: Artificial Sequence
<220> FEATURE:
<223> OTHER INFORMATION: hGH

<400> SEQUENCE: 67
cttgaaaatt tggcccgtgc gaggcgatcc gtcttcgagg cggcccatca gagtctgaat    60

<210> SEQ ID NO 68
<211> LENGTH: 60
<212> TYPE: DNA
<213> ORGANISM: Artificial Sequence
<220> FEATURE:
<223> OTHER INFORMATION: hGH

<400> SEQUENCE: 68
aagaagcagt agagcagacc gtaattttc aacaaagcat cgtcattgtg ggagttagta    60

<210> SEQ ID NO 69
<211> LENGTH: 56
<212> TYPE: DNA
<213> ORGANISM: Artificial Sequence
<220> FEATURE:
<223> OTHER INFORMATION: hGH

<400> SEQUENCE: 69
tcagaaaccg cacgagccct ccactgagcg gcactgcacg atacggagga aggttt       56

<210> SEQ ID NO 70
<211> LENGTH: 23
<212> TYPE: DNA
<213> ORGANISM: Artificial Sequence
<220> FEATURE:
<223> OTHER INFORMATION: primer

<400> SEQUENCE: 70
tttccaacaa tcccgctgag ccg                                           23

<210> SEQ ID NO 71
<211> LENGTH: 31
<212> TYPE: DNA
<213> ORGANISM: Artificial Sequence
<220> FEATURE:
<223> OTHER INFORMATION: primer

<400> SEQUENCE: 71
gccggtacct cagaaaccgc acgagccctc c                                  31

<210> SEQ ID NO 72
<211> LENGTH: 585
<212> TYPE: DNA
<213> ORGANISM: Artificial Sequence
<220> FEATURE:
<223> OTHER INFORMATION: hGH

<400> SEQUENCE: 72
```

```
tttccaacaa tcccgctgag ccgcctcttc gataacgctt cgctccgcgc tcaccgcctg      60
caccaactcg cgttcgacac gtaccaggaa ttcgaggaag cgtatattcc caaggaacag     120
aaatactcgt ttctccaaaa cccccaaacc agcctctgct tttccgagtc gattcctacc     180
ccctccaatc gtgaggaaac ccagcaaaaa agcaacctcg agttgctgcg tatctcactg     240
cttcttatcc agtcctggct ggagcccgtg cagtttttgc gcagcgtctt tgctaactct     300
cttgtgtatg gagcgtcgga ttccaacgtg tacgatcttt tgaaggatct cgaagagggt     360
attcagactc tgatgggccg cctcgaagac ggatcgcctc gcacgggcca aattttcaag     420
caaacctaca gcaaatttga tactaactcc cacaatgacg atgctttgtt gaaaaattac     480
ggtctgctct actgcttctt caaggatatg gataaggtcg aaaccttcct ccgtatcgtg     540
cagtgccgct cagtggaggg ctcgtgcggt ttctgaggta ccggc                    585
```

<210> SEQ ID NO 73
<211> LENGTH: 46
<212> TYPE: DNA
<213> ORGANISM: Artificial Sequence
<220> FEATURE:
<223> OTHER INFORMATION: primer

<400> SEQUENCE: 73

```
cggctcagcg ggattgttgg aaatgccgtt gccacaggtg cggcca                    46
```

<210> SEQ ID NO 74
<211> LENGTH: 46
<212> TYPE: DNA
<213> ORGANISM: Artificial Sequence
<220> FEATURE:
<223> OTHER INFORMATION: primer

<400> SEQUENCE: 74

```
cggctcagcg ggattgttgg aaagcgaatg ctgggatagc aacgcc                    46
```

<210> SEQ ID NO 75
<211> LENGTH: 46
<212> TYPE: DNA
<213> ORGANISM: Artificial Sequence
<220> FEATURE:
<223> OTHER INFORMATION: primer

<400> SEQUENCE: 75

```
cggctcagcg ggattgttgg aaagcggccc tcgatggttg ggttgg                    46
```

<210> SEQ ID NO 76
<211> LENGTH: 46
<212> TYPE: DNA
<213> ORGANISM: Artificial Sequence
<220> FEATURE:
<223> OTHER INFORMATION: primer

<400> SEQUENCE: 76

```
cggctcagcg ggattgttgg aaagcggccc tcgatatcag catcgt                    46
```

<210> SEQ ID NO 77
<211> LENGTH: 46
<212> TYPE: DNA
<213> ORGANISM: Artificial Sequence
<220> FEATURE:
<223> OTHER INFORMATION: primer

<400> SEQUENCE: 77
cggctcagcg ggattgttgg aaagcggccc tcgatgtact ggaact        46

<210> SEQ ID NO 78
<211> LENGTH: 60
<212> TYPE: DNA
<213> ORGANISM: Artificial Sequence
<220> FEATURE:
<223> OTHER INFORMATION: Teriparatide

<400> SEQUENCE: 78
agcgtctccg agattcagct tatgcacaac ctgggcaagc acttgaactc catggagcga        60

<210> SEQ ID NO 79
<211> LENGTH: 62
<212> TYPE: DNA
<213> ORGANISM: Artificial Sequence
<220> FEATURE:
<223> OTHER INFORMATION: Teriparatide

<400> SEQUENCE: 79
gaagttgtgg acatcttgca gtttctttcg cagccattcg actcgctcca tggagttcaa        60
gt        62

<210> SEQ ID NO 80
<211> LENGTH: 25
<212> TYPE: DNA
<213> ORGANISM: Artificial Sequence
<220> FEATURE:
<223> OTHER INFORMATION: primer

<400> SEQUENCE: 80
agcgtctccg agattcagct tatgc        25

<210> SEQ ID NO 81
<211> LENGTH: 33
<212> TYPE: DNA
<213> ORGANISM: Artificial Sequence
<220> FEATURE:
<223> OTHER INFORMATION: primer

<400> SEQUENCE: 81
gccggtacct cagaagttgt ggacatcttg cag        33

<210> SEQ ID NO 82
<211> LENGTH: 114
<212> TYPE: DNA
<213> ORGANISM: Artificial Sequence
<220> FEATURE:
<223> OTHER INFORMATION: Teriparatide

<400> SEQUENCE: 82
agcgtctccg agattcagct tatgcacaac ctgggcaagc acttgaactc catggagcga        60
gtcgaatggc tgcgaaagaa actgcaagat gtccacaact tctgaggtac cggc        114

<210> SEQ ID NO 83
<211> LENGTH: 48
<212> TYPE: DNA
<213> ORGANISM: Artificial Sequence
<220> FEATURE:
<223> OTHER INFORMATION: primer

<400> SEQUENCE: 83
gcataagctg aatctcggag acgcttgccg ttgccacagg tgcggcca        48

```
<210> SEQ ID NO 84
<211> LENGTH: 48
<212> TYPE: DNA
<213> ORGANISM: Artificial Sequence
<220> FEATURE:
<223> OTHER INFORMATION: primer

<400> SEQUENCE: 84
gcataagctg aatctcggag acgctagcga atgctgggat agctacgc          48

<210> SEQ ID NO 85
<211> LENGTH: 46
<212> TYPE: DNA
<213> ORGANISM: Artificial Sequence
<220> FEATURE:
<223> OTHER INFORMATION: primer

<400> SEQUENCE: 85
ccaacccaac catcgagggc cgcagcgtct ccgagattca gcttat            46

<210> SEQ ID NO 86
<211> LENGTH: 25
<212> TYPE: DNA
<213> ORGANISM: Artificial Sequence
<220> FEATURE:
<223> OTHER INFORMATION: primer

<400> SEQUENCE: 86
gcggccctcg atggttgggt tggtc                                    25

<210> SEQ ID NO 87
<211> LENGTH: 25
<212> TYPE: DNA
<213> ORGANISM: Artificial
<220> FEATURE:
<223> OTHER INFORMATION: primer

<400> SEQUENCE: 87
gtactggaac tcttccaggt aagcg                                    25

<210> SEQ ID NO 88
<211> LENGTH: 46
<212> TYPE: DNA
<213> ORGANISM: Artificial
<220> FEATURE:
<223> OTHER INFORMATION: primer

<400> SEQUENCE: 88
agtacgaaaa cctgtacttc cagagcgtct ccgagattca gcttat            46

<210> SEQ ID NO 89
<211> LENGTH: 36
<212> TYPE: DNA
<213> ORGANISM: Artificial
<220> FEATURE:
<223> OTHER INFORMATION: primer

<400> SEQUENCE: 89
gccggtacct catcagaagt tgtggacatc ttgcag                        36

<210> SEQ ID NO 90
<211> LENGTH: 54
<212> TYPE: DNA
<213> ORGANISM: Artificial
<220> FEATURE:
<223> OTHER INFORMATION: Biva18
```

```
<400> SEQUENCE: 90
cgcccgggtg gaggtggcaa cggagatttc gaggagatcc cggaagagta cctg         54

<210> SEQ ID NO 91
<211> LENGTH: 51
<212> TYPE: DNA
<213> ORGANISM: Artificial
<220> FEATURE:
<223> OTHER INFORMATION: primer

<400> SEQUENCE: 91
ccgttgccac ctccacccgg gcgcttgtac tggaactctt ccaggtaagc g            51

<210> SEQ ID NO 92
<211> LENGTH: 37
<212> TYPE: DNA
<213> ORGANISM: Artificial
<220> FEATURE:
<223> OTHER INFORMATION: primer

<400> SEQUENCE: 92
gccggtacct catcacaggt actcttccgg gatctcc                            37

<210> SEQ ID NO 93
<211> LENGTH: 18
<212> TYPE: PRT
<213> ORGANISM: Artificial
<220> FEATURE:
<223> OTHER INFORMATION: Biva18

<400> SEQUENCE: 93

Arg Pro Gly Gly Gly Gly Asn Gly Asp Phe Glu Glu Ile Pro Glu Glu
1               5                   10                  15
Tyr Leu
```